US008338179B2

(12) United States Patent
Enenkel et al.

(10) Patent No.: US 8,338,179 B2
(45) Date of Patent: *Dec. 25, 2012

(54) NEOMYCIN-PHOSPHOTRANSFERASE-GENES AND METHODS FOR THE SELECTION OF RECOMBINANT CELLS PRODUCING HIGH LEVELS OF A DESIRED GENE PRODUCT

(75) Inventors: Barbara Enenkel, Warthausen (DE); Juergen Fieder, Unterstadion (DE); Ralf Otto, Oggelshausen (DE); Kerstin Sautter, Biberach (DE); Klaus Bergemann, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 654 days.

This patent is subject to a terminal disclaimer.

(21) Appl. No.: 11/969,644

(22) Filed: Jan. 4, 2008

(65) Prior Publication Data
US 2008/0131969 A1    Jun. 5, 2008

Related U.S. Application Data

(63) Continuation of application No. 10/724,301, filed on Nov. 26, 2003, now Pat. No. 7,344,886.

(60) Provisional application No. 60/431,535, filed on Dec. 6, 2002, provisional application No. 60/487,902, filed on Jul. 17, 2003.

(30) Foreign Application Priority Data

Nov. 29, 2002  (DE) .................................. 102 56 081
Jul. 8, 2003   (DE) .................................. 103 30 686

(51) Int. Cl.
C12N 9/12     (2006.01)
C12N 15/63    (2006.01)
C12N 5/00     (2006.01)
C07H 21/04    (2006.01)

(52) U.S. Cl. ............. 435/455; 435/194; 435/320.1; 435/325; 536/23.2

(58) Field of Classification Search .............. 435/194, 435/15, 252.3, 320.1, 455; 536/23.2
See application file for complete search history.

(56) References Cited

U.S. PATENT DOCUMENTS

| 5,179,017 | A   | 1/1993  | Axel et al.  |         |
|-----------|-----|---------|--------------|---------|
| 6,060,273 | A   | 5/2000  | Dirks et al. |         |
| 6,063,598 | A   | 5/2000  | Enenkel et al. |       |
| 6,096,505 | A   | 8/2000  | Selby et al. |         |
| 7,344,886 | B2* | 3/2008  | Enenkel et al. | 435/455 |
| 7,732,181 | B2* | 6/2010  | Enenkel et al. | 435/194 |

FOREIGN PATENT DOCUMENTS

| EP | 0393438 A2 | 10/1990 |
| JP | 4179485    | 6/1992  |
| WO | 9208796 A1 | 5/1992  |
| WO | 9405785 A1 | 3/1994  |
| WO | 9428143 A1 | 12/1994 |
| WO | 9715664 A1 | 3/1997  |
| WO | 9953046 A1 | 10/1999 |
| WO | 0034318 A1 | 6/2000  |
| WO | 0034326 A1 | 6/2000  |
| WO | 0034526 A1 | 6/2000  |
| WO | 0104306 A1 | 1/2001  |
| WO | 0127150 A2 | 4/2001  |

OTHER PUBLICATIONS

Clontech, catalogue, Takara BIO Inc. Product review (Clontechniques, 2002, p. 21, Introduction of a new product of Clontech, IRES Bicistronic Expression Vectors).

Stephen F. Altschul et al; Gapped Blast and PSI-Blast: A New Generation of Protein Database Search Programs; Nucleic Acids Research (1997) vol. 25 No. 17 pp. 3389-3402; Oxford University Press.

Stephen F. Altschul et al; Basic Local Alignment Search Tool; Journal of Molecular Biology (1990) vol. 215 No. 3 pp. 403-410; Academic Press Limited.

Warren Gish et al; Identification of Protein Coding Regions by Database Similarity Search; Nature Genetics (1993) vol. 3 pp. 266-272; Nature Publishing Group.

Manfred Gossen et al; Inducible Gene Expression Systems for Higher Eukaryotic Cells; Current Opinion in Biotechnology (1994) vol. 5 pp. 516-520; Current Biology Ltd.

Mogens Duch et al; Determination of Transient or Stable Neo Expression Levels in Mammalian Cells; Gene (1990) vol. 95 pp. 285-288; Elsevier Science Publishers B.V.

Shi-Zhen Hu et al; Minibody: A Novel Engineered Anti-Carcinoembryonic Antigen Antibody Fragment (Single-Chain Fv-CH3) which Exhibits Rapid, High-Level Targeting of Xenografts; Cancer Research (1996) vol. 56 pp. 3055-3061.

James S. Huston et al; Protein Engineering of Antibody Binding Sites: Recovery of Specific Activity in an Anti-Digoxin Single-Chain Fv Analogue Produced in *Excherichia coli*; Proceedings of the National Academy of Sciences of the United States of America (1988) vol. 85 pp. 5879-5883.

Alexander A. Kortt et al; Single-Chain Fv Fragments of Anti-Neuraminidase Antibody NC10 Containing Five-and Ten-Residue Linkers Form Dimers and with Zero-Residue Linker a Trimer; Protein Engineering (1997) vol. 10 No. 4 pp. 423-433.

(Continued)

*Primary Examiner* — Tekchand Saidha
(74) *Attorney, Agent, or Firm* — Michael P. Morris; Edouard G. Lebel

(57) ABSTRACT

The invention relates to modified neomycin phosphotransferase genes and their use in a selection method for high-producing recombinant cells. The invention further relates to expression vectors which contain a modified neomycin phosphotransferase gene and a gene of interest functionally linked to a heterologous promoter and a method of preparing heterologous gene products using these expression vectors.

31 Claims, 16 Drawing Sheets

OTHER PUBLICATIONS

Brett Lovejoy et al; crystal structure of a Synthetic Triple-Stranded Helical Bundle; Research Article (1993) vol. 259 pp. 1288-1293.

Thomas L. Madden et al; Applications of Network Blast Server; Methods in Enzymology (1996) vol. 266 pp. 131-141.

Yasumi Ohshima et al; Signals for the Selection of a Splice in Pre-mRNA Computer Analysis of Splice Junction Sequences and Like Sequences; Journal Molecular Biology (1987) vol. 195 pp. 247-259.

Peter Pack et al; Tetravalent Miniantibodies with High Avidity Assembling in Escherichia coli; Journal Molecular Biology (1995) vol. 246 pp. 28-34; Academic Press Limited.

Olga Perisic et al; Crystal Structure of a Diabody, a Bivalent Antibody Fragment; Structure (1994) vol. 2 pp. 1217-1226; Current Biology Ltd.

Steven G. Platt et al; Dot Assay for Neomycin Phosphotransferase Activity in Crude Cell Extracts; Analytical Biochemistry (1987) vol. 162 pp. 529-535; Academic Press, Inc.

Christian C. Simonsen et al; Isolation and Expression of an Altered Mouse Dihydrofolate Reductase cDNA; Proceedings of the National Academy of Sciences of the United States of America (1983) vol. 80 pp. 2495-2499.

Teizo Yoshimura et al; Human Monocyte Chemoattractan Protein-1 (MCP-1): Full-Length cDNA Cloning, Expression in Mitogen-Stimulated Blood Mononuclear Leukocytes, and sequence Similarity to Mouse Competence Gene JE; Febs Letters (1989) vol. 244 No. 2 pp. 487-493; Elsevier Science Publishers B.V.

M. Wigler et al; Transformation of Mammalian Cells with an Amplifiable Dominant-Acting Gene; Proceedings of the National Academy of Sciences of the United States of America (1980) vol. 77 No. 6 pp. 3567-3570.

Steffen Faisst et al; Compilation of Vertebrate-Encoded Transcription Factors; Nucleic Acids Research (1992) vol. 20 No. 1 pp. 3-26; Oxford University Press.

Peter Pack et al; Improved Bivalent Miniantibodies, with identical Avidity as whole Antibodies, Produced by High Cell Density Fermentation of Escherichia coli; Bio/Technology (1993) vol. 11 pp. 1271-1277; Nature Publishing Group.

Jinghui Zhang et al; PowerBLAST: A New Network Blast Application for Interactive or Automated Sequence Analysis and Annotation; Genome Research (1997) vol. 7 pp. 649-656; Cold Spring Harbor Laboratory Press.

Daniel A Haber et al; Chromosome-Mediated Transfer and Amplification of an Altered Mouse Dihydrofolate Reductase Gene; Somatic Cell Genetics (1982) vol. 8 No. 4 pp. 499-508; Plenum Publishing Corporation.

International Search Report for PCT/EP03/13203, (2003).

J. Blazquez et al; Mutations in the aphA-2 gene of transposon Tn5 mapping within the regions highly conserved in aminoglycoside-phosphotransferases strongly reduce aminoglycoside resistance; Molecular Microbiology 1991 vol. 5 No. 6 pp. 1511-1518.

J. Blazquez et al; Mutations in the aphA-2 gene of transposon Tn5 mapping within the regions highly conserved in aminoglycoside-phosphotransferases strongly reduce aminoglycoside resistance; Molecular Microbiology (1991) vol. 5 No. 6 pp. 1511-1518.

Paul R. Thompson et al; The COOH Terminus of Aminoglycoside Phosphotransferase (3')-IIIa Is Critical for Antibiotic Recognition and Resistance; The Journal of Biological Chemistry vol. 274 No. 43 pp. 30697-30706 (1999); American Soc. for Biochemistry and Molecular Biology, Inc.

Marianne Z. Metz et al; Construction and Characterization of Single-Transcript Tricistronic Retroviral Vectors Using Two Internal Ribosome Entry Sites; Somatic Cell and Moecular Genetics (1998) vol. 24 No. 1 pp. 53-69; Plenum Publishing Corp.

Hitoshi Niwa et al; Efficient selection for high-expression transfectants with a novel eukaryotic vector; Gene (1991) vol. 108 pp. 193-200; Elsevier Science Publishers B.V.

Richard L. Yenofsky et al; A mutant neomycin phosphotransferase II gene reduces the resistance of transformants to antibiotic selection pressure; Biochemistry (May 1990) vol. 87 pp. 3435-3439; Proc. Natl Acad Science.

Wai-Ching Hon et al; Structure of an Enzyme Required for Aminoglycoside Antibiotic Resistance Reveals Homology to Eukaryotic Protein Kinases; Cell (Jun. 13, 1997) vol. 89 pp. 887-895; Cell Press.

Cord Hemann et al; High Copy Expression Vector Based on Amplification-Promoting Sequences; DNA and Cell Biology (1994) vol. 13 No. 4 pp. 437-445; Mary Ann Leibert Inc Publishers.

Rolf G. Werner et al; Appropriate Mammalian Expression Systems for Biopharmaceuticals; Drug Research (1998) vol. 48(11) No. 8 pp. 870-880; Sonderdruck/ Reprint.

Gail Urlaub et al; Deletion of the Diploid Dihydrofolate Reductase Locus from Cultured Mammalian Cells; Cell (1983) vol. 33 pp. 405-412; Department of Biological Sciences, Columbia University.

Yoshikazu Sugimoto et al; Efficient Expression of Drug-selectable Genes in Retroviral Vectors under Control of an Internal Ribosome Entry Site; Bio/Technology (Jul. 1994) vol. 12 pp. 694-698; National Cancer Institute.

K.J. Shaw et al; Molecular Genetics of Aminoglycoside Resistance Genes and Familial Relationships of the Aminoglycoside-Modifying Enzymes; Microbiological Reviews (Mar. 1993) vol. 57 No. 1 pp. 138-163; American Society for Microbiology.

N. Ramesh et al; High-titer bicistronic retroviral vectors employing foot-and-mouth disease virus internal ribosome entry site; Nucleic Acids Research (1996) vol. 24 No. 14 pp. 2697-2700; Oxford University Press.

Jerry Pelletier et al; Internal initiation of translation of eukaryotic mRNA directed by a sequence derived from poliovirus RNA; Nature (Jul. 1998) vol. 334 pp. 320-325; McGill Cancer Center, McGill University, Montreal Canada.

D.D. Mosser et al; Use of a Dicistronic Expression Cassette Encoding the Green Fluorescent Protein for the Screening and selection of Cells Expressing Inducible Gene Products; Biotechniques (Jan. 1997) vol. 22 pp. 150-161; National Research Council, Montreal Canada.

Richard A. Morgan et al; Retroviral vectors containing putative internal ribosome entry sites: development of a polycistronic gene transfer system and applications to human gene therapy; Nucleic Acids Research (1992) vol. 20 No. 6 pp. 1293-1299; Molecular Hematology Branch.

Lucia Monaco et al; Expression of recombinant human granulocyte colony-stimulating factor in CHO dhfr-cells: new insights into the in vitro amplification expression system; Gene (1996) vol. 180 pp. 145-150; Elsevier Science B.V.

Randal J. Kaufman; Selection and Coamplification of Heterologous Genes in Mammalian Cells; Methods in Enzymology (1990) vol. 185 pp. 537-566; Academic Press.

Sung K. Jang et al; Initiation of Protein Synthesis by Internal Entry of Ribosomes into the 5' Nontranslated Region of Encephalomyocarditis Virus RNA in Vivo; Journal of Virology (Apr. 1989) vol. 63 No. 4 pp. 1651-1660; American Society for Microbiology.

Keith D. Hanson et al; Analysis of Biological Selections for High-Efficiency Gene Targeting; Molecular and Cellular Biology (Jan. 1995) vol. 15 No. 1 pp. 45-51; American Society for Microbiology.

Martin Chalfie et al; Green Fluorescent Protein as a Marker for Gene Expression; Science (Feb. 11, 1994) vol. 263 pp. 802-805.

Monique V. Davies et al; The Sequence Context of the Initiation Codon in the Encephalomyocarditis Virus Leader Modulates Efficiency of Internal Translation Initiation; Journal of Virology Apr. 1992 vol. 66 No. 4 pp. 1924-1932; American Society for Microbiology.

D.L. Burk et al; Structural Analyses of Nucleotide Binding to an Aminoglycoside Phosphotransferase; Biochemistry 2001 vol. 40 pp. 8756-8764; American Chemical Society.

Robert P. Bennett et al; Fusion of Green Flourescent Protein with the Zeocin TM-Resistance Marker Allows Visual Screening and Drug Selection of Transfected Eukaryotic Cells; Biotechniques Mar. 1998 vol. 24 No. 3 pp. 478-482; Invitrogen Corporation Carlsbad, Ca.

Mohammaed A Adam et al; Internal Initiation of Translation in Retroviral Vectors Carrying Picornavirus 5' Nontranslated Regions; Journal of Virology Sep. 1991 vol. 65 No. 9 pp. 4985-4990; American Society for Microbiology.

Wai-Ching Hon et al; Structure of an Enzyme Required for Aminoglycoside Antibiotic Resistance Reveals Homology to Eukaryotic Protein Kinases; Cell Jun. 13, 1997 vol. 89 pp. 887-895; Cell Press.

Richard L. Yenofsky et al; A Mutant neomycin phosphotransferase II gene reduces the resistance of transformants to antibiotic selection pressure; Pro. Natl Acad. Science May 1990 vol. 87 pp. 3435-3439; Phytogen Pasadena, CA.

Semra Kocabiyik et al; Site-Specific Mutations of Conserved C-Terminal Residues in Aminoglycoside 3'-Phosphotransferase II: Phenotypic and Structural Analysis of Mutant Enzymes; Biochemical and Biophysical Research Comm. Jun. 1992 vol. 185 No. 3 pp. 925-931; Academic Press.

Perlin, Michael H. "Developing a Snapshot of the ATP Binding Domain(s) of Aminoglycoside Phosphotransferases" Frontiers in Bioscience V 4, pp. 63-71, (1999).

Branden et al. "Introduction to Protein Structure" Garland Publishing Inc., p. 247 (1991).

Edwin H. Horwitz, et al. "Isolated allogeneic bone marrow-derived mesenchymal cells engraft and stimulate growth in children with osteogenesis imperfecta: Implications for cell therapy of bone" PNAS, Jun. 25, 2002 vol. 99, No. 13, pp. 8932-8937.

Kazuo Harada, et al. "Screening in vivo for RNA-binding peptides from combinatorial libraries" Nucleic Acids Symposium Series No. 44, 2000 pp. 269-270.

Ming Cheng et al., "Genetic Transformation of Wheat Mediated by Agrobacterium tumefaciens" Plant Physiol. (1997) 115: pp. 971-980.

* cited by examiner

Figure 4

```
  1  MIEQDGLHAG  SPAAWVERLF  GYDWAQQTIG  CSDAAVFRLS  AQGRPVLFVK

91
                                                    ★
 51  TDLSGALNEL  QDEAAARLSWL  ATTGVPCAAV  LDVVTEAGRD  WLLIGEVPGQ

101  DLLSSHLAPA  EKVSIMADAM  RRLHTLDPAT  CPEDHQAKHR  IERARTRMEA 182         190             198
                                    ★           ★               ★
151  GLVDQDDLDE  EHQGLAPAEL  FARLKASMPD  GEDLVVTHGD  ACLPNIMVEN
                                                    Motif 1

227                     240
                            ★                       ★
201  GRFSGFIDCG  RLGVADRYQD  IALATRDIAE  ELGGEWADRF  LVLYGTAAPD
     Motif 2     261
                 ★
251  SQRIAFYRLL  DEFF
     Motif 3
```

Figure 9B

| NPT-Variant | % Enzyme activity (WT-NPT = 100%) |
|---|---|
| NPT-Wildtype | 100.0 |
| Trp91Ala | 53.2 |
| Glu182Gly | 25.8 |
| Glu182Asp | 22.0 |
| Val198Gly | 61.9 |
| Asp227Ala | 26.9 |
| Asp227Val | 16.4 |
| Asp227Gly | 30.0 |
| Phe240Ile | 23.4 |
| Asp261Gly | 3.1 |
| Asp261Asn | 1.5 |

ND METHODS FOR THE SELECTION OF
RECOMBINANT CELLS PRODUCING HIGH
LEVELS OF A DESIRED GENE PRODUCT

SEQUENCE LISTING

<160> NUMBER OF SEQ ID NOS: 55

<210> SEQ ID NO 1
<211> LENGTH: 795
<212> TYPE: DNA
<213> ORGANISM: Escherichia coli

<400> SEQUENCE: 1

```
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caagacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgag catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tctga                                                      795
```

<210> SEQ ID NO 2
<211> LENGTH: 264
<212> TYPE: PRT
<213> ORGANISM: Escherichia coli

<400> SEQUENCE: 2

Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
             20                  25                  30

Asp Ala Ala Val Phe Arg Leu Ser Ala Gln Gly Arg Pro Val Leu Phe
         35                  40                  45

Val Lys Thr Asp Leu Ser Gly Ala Leu Asn Glu Leu Gln Asp Glu Ala
     50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                 85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala

```
                130                 135                 140
Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
                195                 200                 205

Cys Gly Arg Leu Gly Val Ala Asp Arg Tyr Gln Asp Ile Ala Leu Ala
                210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
                260

<210> SEQ ID NO 3
<211> LENGTH: 795
<212> TYPE: DNA
<213> ORGANISM: Artificial sequence
<220> FEATURE:
<223> OTHER INFORMATION: Neomycin mutant E182G

<400> SEQUENCE: 3
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcagggcc gcccggttct ttttgtcaag accgacctgt ccggtgccct gaatgaactg     180
caagacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgag catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tctga                                                      795

<210> SEQ ID NO 4
<211> LENGTH: 264
<212> TYPE: PRT
<213> ORGANISM: Artificial sequence
<220> FEATURE:
<223> OTHER INFORMATION: Neomycin mutant E182G

<400> SEQUENCE: 4

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30
```

```
Asp Ala Ala Val Phe Arg Leu Ser Ala Gln Gly Arg Pro Val Leu Phe
            35                  40                  45
Val Lys Thr Asp Leu Ser Gly Ala Leu Asn Glu Leu Gln Asp Glu Ala
 50                  55                  60
Ala Arg Leu Ser Trp Leu Ala Thr Thr Gly Val Pro Cys Ala Ala Val
 65                  70                  75                  80
Leu Asp Val Val Thr Glu Ala Gly Arg Asp Trp Leu Leu Leu Gly Glu
                 85                  90                  95
Val Pro Gly Gln Asp Leu Leu Ser Ser His Leu Ala Pro Ala Glu Lys
                100                 105                 110
Val Ser Ile Met Ala Asp Ala Met Arg Arg Leu His Thr Leu Asp Pro
            115                 120                 125
Ala Thr Cys Pro Phe Asp His Gln Ala Lys His Arg Ile Glu Arg Ala
130                 135                 140
Arg Thr Arg Met Glu Ala Gly Leu Val Asp Gln Asp Leu Asp Glu
145                 150                 155                 160
Glu His Gln Gly Leu Ala Pro Ala Glu Leu Phe Ala Arg Leu Lys Ala
                165                 170                 175
Ser Met Pro Asp Gly Gly Asp Leu Val Val Thr His Gly Asp Ala Cys
            180                 185                 190
Leu Pro Asn Ile Met Val Glu Asn Gly Arg Phe Ser Gly Phe Ile Asp
            195                 200                 205
Cys Gly Arg Leu Gly Val Ala Asp Arg Tyr Gln Asp Ile Ala Leu Ala
210                 215                 220
Thr Arg Asp Ile Ala Glu Leu Gly Gly Glu Trp Ala Asp Arg Phe
225                 230                 235                 240
Leu Val Leu Tyr Gly Ile Ala Ala Pro Asp Ser Gln Arg Ile Ala Phe
                245                 250                 255
Tyr Arg Leu Leu Asp Glu Phe Phe
                260

<210> SEQ ID NO 5
<211> LENGTH: 795
<212> TYPE: DNA
<213> ORGANISM: Artificial sequence
<220> FEATURE:
<223> OTHER INFORMATION: Neomycin mutant W91A

<400> SEQUENCE: 5
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caagacgagg cagcgcggct atcgtggctg gccacgacgg gcgttccttg cgcagctgtg     240
ctcgacgttg tcactgaagc gggaagggac gcgctgctat gggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgag catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
```

```
gacgagttct tctga                                                      795
```

<210> SEQ ID NO 6
<211> LENGTH: 264
<212> TYPE: PRT
<213> ORGANISM: Artificial sequence
<220> FEATURE:
<223> OTHER INFORMATION: Neomycin mutant W91A

<400> SEQUENCE: 6

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Ala Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 7
<211> LENGTH: 795
<212> TYPE: DNA
<213> ORGANISM: Artificial sequence
<220> FEATURE:
<223> OTHER INFORMATION: Neomycin mutant V198G

<400> SEQUENCE: 7

```
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
```

```
caagacgagg cagcgcggct atcgtggctg ccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgag catgcccgac    540
ggcgaggatc tcgtcgtgac ccatggcgat gcctgcttgc cgaatatcat ggggaaaat    600 ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795
```

<210> SEQ ID NO 8
<211> LENGTH: 264
<212> TYPE: PRT
<213> ORGANISM: Artificial sequence
<220> FEATURE:
<223> OTHER INFORMATION: Neomycin mutant V198G

<400> SEQUENCE: 8

```
Met Ile Glu Gln Asp Gly Leu His Ala Gly Ser Pro Ala Ala Trp Val
 1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Gly Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Pro Asp Ser Gln Arg Ile Ala Phe
                245                 250                 255
```

Tyr Arg Leu Leu Asp Glu Phe Phe
            260

<210> SEQ ID NO 9
<211> LENGTH: 795
<212> TYPE: DNA
<213> ORGANISM: Artificial sequence
<220> FEATURE:
<223> OTHER INFORMATION: Neomycin mutant D227A

<400> SEQUENCE: 9

| | | | | | |
|---|---|---|---|---|---|
| atgattgaac | aagatggatt | gcacgcaggt | tctccggccg | cttgggtgga | gaggctattc | 60 |
| ggctatgact | gggcacaaca | gacaatcggc | tgctctgatg | ccgccgtgtt | ccggctgtca | 120 |
| gcgcaggggc | gcccggttct | ttttgtcaag | accgacctgt | ccggtgccct | gaatgaactg | 180 |
| caagacgagg | cagcgcggct | atcgtggctg | gccacgacgg | gcgttccttg | cgcagctgtg | 240 |
| ctcgacgttg | tcactgaagc | gggaagggac | tggctgctat | gggcgaagt | gccggggcag | 300 |
| gatctcctgt | catctcacct | tgctcctgcc | gagaaagtat | ccatcatggc | tgatgcaatg | 360 |
| cggcggctgc | atacgcttga | tccggctacc | tgcccattcg | accaccaagc | gaaacatcgc | 420 |
| atcgagcgag | cacgtactcg | gatggaagcc | ggtcttgtcg | atcaggatga | tctggacgaa | 480 |
| gagcatcagg | ggctcgcgcc | agccgaactg | ttcgccaggc | tcaaggcgag | catgcccgac | 540 |
| ggcgaggatc | tcgtcgtgac | ccatggcgat | gcctgcttgc | cgaatatcat | ggtggaaaat | 600 |
| ggccgctttt | ctggattcat | cgactgtggc | cggctgggtg | tggcggaccg | ctatcaggac | 660 |
| atagcgttgg | ctacccgtgc | tattgctgaa | gagcttggcg | gcgaatgggc | tgaccgcttc | 720 |
| ctcgtgcttt | acggtatcgc | cgctcccgat | tcgcagcgca | tcgccttcta | tcgccttctt | 780 |
| gacgagttct | tctga | | | | | 795 |

<210> SEQ ID NO 10
<211> LENGTH: 264
<212> TYPE: PRT
<213> ORGANISM: Artificial sequence
<220> FEATURE:
<223> OTHER INFORMATION: Neomycin mutant D227A

<400> SEQUENCE: 10

Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

```
Glu His Gln Gly Leu Ala Pro Ala Leu Phe Ala Arg Leu Lys Ala
            165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
            210                 215                 220

Thr Arg Ala Ile Ala Glu Glu Leu Gly Gly Glu Trp Ala Asp Arg Phe
225             230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 11
<211> LENGTH: 795
<212> TYPE: DNA
<213> ORGANISM: Artificial sequence
<220> FEATURE:
<223> OTHER INFORMATION: Neomycin mutant D227V

<400> SEQUENCE: 11

```
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcagggc gcccggttct ttttgtcaag accgacctgt ccggtgccct gaatgaactg     180
caagacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgag catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtgt tattgctgaa gagcttggcg gcgaatgggc tgaccgcttc     720
ctcgtgcttt acggtatcgc cgctcccgat tcgcagcgca tcgccttcta tcgccttctt     780
gacgagttct tctga                                                      795
```

<210> SEQ ID NO 12
<211> LENGTH: 264
<212> TYPE: PRT
<213> ORGANISM: Artificial sequence
<220> FEATURE:
<223> OTHER INFORMATION: Neomycin mutant D227V

<400> SEQUENCE: 12

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
```

```
                50                  55                  60
Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                 85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Val Ile Ala Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 13
<211> LENGTH: 795
<212> TYPE: DNA
<213> ORGANISM: Artificial sequence
<220> FEATURE:
<223> OTHER INFORMATION: Neomycin mutant D261G

<400> SEQUENCE: 13

```
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcaggggc gcccggttct ttttgtcaag accgacctgt ccggtgccct gaatgaactg   180
caagacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgag catgcccgac   540
ggcgaggatc tcgtcgtgac ccatggcgat gcctgcttgc cgaatatcat ggtggaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
ggcgagttct tctga                                                    795
```

```
<210> SEQ ID NO 14
<211> LENGTH: 264
<212> TYPE: PRT
<213> ORGANISM: Artificial sequence
<220> FEATURE:
<223> OTHER INFORMATION: Neomycin mutant D261G

<400> SEQUENCE: 14

Met Ile Glu Gln Asp Gly Leu His Ala Gly Ser Pro Ala Ala Trp Val
  1               5                  10                  15

Glu Arg Leu Phe Gly Tyr Asp Trp Ala Gln Gln Thr Ile Gly Cys Ser
                 20                  25                  30

Asp Ala Ala Val Phe Arg Leu Ser Ala Gln Gly Arg Pro Val Leu Phe
             35                  40                  45

Val Lys Thr Asp Leu Ser Gly Ala Leu Asn Glu Leu Gln Asp Glu Ala
         50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                 85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Gly Glu Phe Phe
            260

<210> SEQ ID NO 15
<211> LENGTH: 795
<212> TYPE: DNA
<213> ORGANISM: Artificial sequence
<220> FEATURE:
<223> OTHER INFORMATION: Neomycin mutant D261N

<400> SEQUENCE: 15
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caagacgagg cagcgcggct atcgtggctg gccacgacgg gcgttccttg cgcagctgtg     240
ctcgacgttg tcactgaagc gggaagggac tggctgctat tgggcgaagt gccggggcag     300
```

```
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgag catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta cgccttcttt    780
aacgagttct tctga                                                     795
```

<210> SEQ ID NO 16
<211> LENGTH: 264
<212> TYPE: PRT
<213> ORGANISM: Artificial sequence
<220> FEATURE:
<223> OTHER INFORMATION: Neomycin mutant D261N
<400> SEQUENCE: 16

```
Met Ile Glu Gln Asp Gly Leu His Ala Gly Ser Pro Ala Ala Trp Val
  1               5                  10                  15

Glu Arg Leu Phe Gly Tyr Asp Trp Ala Gln Gln Thr Ile Gly Cys Ser
             20                  25                  30

Asp Ala Ala Val Phe Arg Leu Ser Ala Gln Gly Arg Pro Val Leu Phe
         35                  40                  45

Val Lys Thr Asp Leu Ser Gly Ala Leu Asn Glu Leu Gln Asp Glu Ala
     50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                 85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asn Glu Phe Phe
            260
```

<210> SEQ ID NO 17
<211> LENGTH: 795
<212> TYPE: DNA
<213> ORGANISM: Artificial sequence
<220> FEATURE:
<223> OTHER INFORMATION: Neomycin mutant F240I

<400> SEQUENCE: 17

```
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcaggggc gcccggttct ttttgtcaag accgacctgt ccggtgccct gaatgaactg   180
caagacgagg cagcgcggct atcgtggctg gccacgacgg gcgttccttg cgcagctgtg   240
ctcgacgttg tcactgaagc gggaagggac tggctgctat gggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgag catgcccgac   540
ggcgaggatc tcgtcgtgac ccatggcgat gcctgcttgc cgaatatcat ggtggaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcatc   720
ctcgtgcttt acggtatcgc cgctcccgat tcgcagcgca tcgccttcta tcgccttctt   780
gacgagttct tctga                                                   795
```

<210> SEQ ID NO 18
<211> LENGTH: 264
<212> TYPE: PRT
<213> ORGANISM: Artificial sequence
<220> FEATURE:
<223> OTHER INFORMATION: Neomycin mutant F240I

<400> SEQUENCE: 18

```
Met Ile Glu Gln Asp Gly Leu His Ala Gly Ser Pro Ala Ala Trp Val
  1               5                  10                  15

Glu Arg Leu Phe Gly Tyr Asp Trp Ala Gln Gln Thr Ile Gly Cys Ser
                 20                  25                  30

Asp Ala Ala Val Phe Arg Leu Ser Ala Gln Gly Arg Pro Val Leu Phe
             35                  40                  45

Val Lys Thr Asp Leu Ser Gly Ala Leu Asn Glu Leu Gln Asp Glu Ala
         50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                 85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175
```

-continued

```
Ser Met Pro Asp Gly Glu Asp Leu Val Val Thr His Gly Asp Ala Cys
            180                 185                 190
Leu Pro Asn Ile Met Val Glu Asn Gly Arg Phe Ser Gly Phe Ile Asp
            195                 200                 205
Cys Gly Arg Leu Gly Val Ala Asp Arg Tyr Gln Asp Ile Ala Leu Ala
            210                 215                 220
Thr Arg Asp Ile Ala Glu Glu Leu Gly Gly Trp Ala Asp Arg Ile
225                 230                 235                 240
Leu Val Leu Tyr Gly Ile Ala Ala Pro Asp Ser Gln Arg Ile Ala Phe
            245                 250                 255
Tyr Arg Leu Leu Asp Glu Phe Phe
            260
```

<210> SEQ ID NO 19
<211> LENGTH: 795
<212> TYPE: DNA
<213> ORGANISM: Artificial sequence
<220> FEATURE:
<223> OTHER INFORMATION: Neomycin mutant E182D

<400> SEQUENCE: 19

```
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcagggc gcccggttct ttttgtcaag accgacctgt ccggtgccct gaatgaactg     180
caagacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgag catgcccgac     540
ggcgatgatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tgccttcttc     780
gacgagttct tctga                                                       795
```

<210> SEQ ID NO 20
<211> LENGTH: 264
<212> TYPE: PRT
<213> ORGANISM: Artificial sequence
<220> FEATURE:
<223> OTHER INFORMATION: Neomycin mutant E182D

<400> SEQUENCE: 20

```
Met Ile Glu Gln Asp Gly Leu His Ala Gly Ser Pro Ala Ala Trp Val
1               5                   10                  15
Glu Arg Leu Phe Gly Tyr Asp Trp Ala Gln Gln Thr Ile Gly Cys Ser
            20                  25                  30
Asp Ala Ala Val Phe Arg Leu Ser Ala Gln Gly Arg Pro Val Leu Phe
            35                  40                  45
Val Lys Thr Asp Leu Ser Gly Ala Leu Asn Glu Leu Gln Asp Glu Ala
        50                  55                  60
Ala Arg Leu Ser Trp Leu Ala Thr Thr Gly Val Pro Cys Ala Ala Val
65                  70                  75                  80
```

Leu Asp Val Val Thr Glu Ala Gly Arg Asp Trp Leu Leu Gly Glu
             85                  90                  95

Val Pro Gly Gln Asp Leu Leu Ser Ser His Leu Ala Pro Ala Glu Lys
        100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Asp Leu Val Val Thr His Gly Asp Ala Cys
        180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
210                 215                 220

Thr Arg Asp Ile Ala Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 21
<211> LENGTH: 795
<212> TYPE: DNA
<213> ORGANISM: Artificial sequence
<220> FEATURE:
<223> OTHER INFORMATION: Neomycin mutant D227G

<400> SEQUENCE: 21
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caagacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgag catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtgg tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795

<210> SEQ ID NO 22
<211> LENGTH: 264
<212> TYPE: PRT
<213> ORGANISM: Artificial sequence
<220> FEATURE:
<223> OTHER INFORMATION: Neomycin mutant D227G

<400> SEQUENCE: 22

| | | | | | | | | | | | | | | |
|---|---|---|---|---|---|---|---|---|---|---|---|---|---|---|
| Met | Ile | Glu | Gln | Asp | Gly | Leu | His | Ala | Gly | Ser | Pro | Ala | Ala | Trp | Val |
| 1 | | | | 5 | | | | | 10 | | | | | 15 | |
| Glu | Arg | Leu | Phe | Gly | Tyr | Asp | Trp | Ala | Gln | Gln | Thr | Ile | Gly | Cys | Ser |
| | | | 20 | | | | | 25 | | | | | 30 | | |
| Asp | Ala | Ala | Val | Phe | Arg | Leu | Ser | Ala | Gln | Gly | Arg | Pro | Val | Leu | Phe |
| | | 35 | | | | | 40 | | | | | 45 | | | |
| Val | Lys | Thr | Asp | Leu | Ser | Gly | Ala | Leu | Asn | Glu | Leu | Gln | Asp | Glu | Ala |
| | 50 | | | | | 55 | | | | | 60 | | | | |
| Ala | Arg | Leu | Ser | Trp | Leu | Ala | Thr | Thr | Gly | Val | Pro | Cys | Ala | Ala | Val |
| 65 | | | | | 70 | | | | | 75 | | | | | 80 |
| Leu | Asp | Val | Val | Thr | Glu | Ala | Gly | Arg | Asp | Trp | Leu | Leu | Leu | Gly | Glu |
| | | | | 85 | | | | | 90 | | | | | 95 | |
| Val | Pro | Gly | Gln | Asp | Leu | Leu | Ser | Ser | His | Leu | Ala | Pro | Ala | Glu | Lys |
| | | | 100 | | | | | 105 | | | | | 110 | | |
| Val | Ser | Ile | Met | Ala | Asp | Ala | Met | Arg | Arg | Leu | His | Thr | Leu | Asp | Pro |
| | | 115 | | | | | 120 | | | | | 125 | | | |
| Ala | Thr | Cys | Pro | Phe | Asp | His | Gln | Ala | Lys | His | Arg | Ile | Glu | Arg | Ala |
| | 130 | | | | | 135 | | | | | 140 | | | | |
| Arg | Thr | Arg | Met | Glu | Ala | Gly | Leu | Val | Asp | Gln | Asp | Asp | Leu | Asp | Glu |
| 145 | | | | | 150 | | | | | 155 | | | | | 160 |
| Glu | His | Gln | Gly | Leu | Ala | Pro | Ala | Glu | Leu | Phe | Ala | Arg | Leu | Lys | Ala |
| | | | | 165 | | | | | 170 | | | | | 175 | |
| Ser | Met | Pro | Asp | Gly | Glu | Asp | Leu | Val | Val | Thr | His | Gly | Asp | Ala | Cys |
| | | | 180 | | | | | 185 | | | | | 190 | | |
| Leu | Pro | Asn | Ile | Met | Val | Glu | Asn | Gly | Arg | Phe | Ser | Gly | Phe | Ile | Asp |
| | | 195 | | | | | 200 | | | | | 205 | | | |
| Cys | Gly | Arg | Leu | Gly | Val | Ala | Asp | Arg | Tyr | Gln | Asp | Ile | Ala | Leu | Ala |
| | 210 | | | | | 215 | | | | | 220 | | | | |
| Thr | Arg | Gly | Ile | Ala | Glu | Glu | Leu | Gly | Gly | Glu | Trp | Ala | Asp | Arg | Phe |
| 225 | | | | | 230 | | | | | 235 | | | | | 240 |
| Leu | Val | Leu | Tyr | Gly | Ile | Ala | Ala | Pro | Asp | Ser | Gln | Arg | Ile | Ala | Phe |
| | | | | 245 | | | | | 250 | | | | | 255 | |
| Tyr | Arg | Leu | Leu | Asp | Glu | Phe | Phe | | | | | | | | |
| | | | 260 | | | | | | | | | | | | |

<210> SEQ ID NO 23
<211> LENGTH: 795
<212> TYPE: DNA
<213> ORGANISM: Artificial sequence
<220> FEATURE:
<223> OTHER INFORMATION: Neomycin mutant D190G

<400> SEQUENCE: 23

```
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcagggcc gcccggttct ttttgtcaag accgacctgt ccggtgccct gaatgaactg     180
caagacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
```

```
atcgagcgag cacgtactcg gatggaagcc ggtcttgtcg atcaggatga tctggacgaa    480
gagcatcagg ggctcgcgcc agccgaactg ttcgccaggc tcaaggcgag catgcccgac    540
ggcgaggatc tcgtcgtgac ccatggcggt gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795
```

<210> SEQ ID NO 24
<211> LENGTH: 264
<212> TYPE: PRT
<213> ORGANISM: Artificial sequence
<220> FEATURE:
<223> OTHER INFORMATION: Neomycin mutant D190G

<400> SEQUENCE: 24

```
Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
             20                  25                  30

Asp Ala Ala Val Phe Arg Leu Ser Ala Gln Gly Arg Pro Val Leu Phe
         35                  40                  45

Val Lys Thr Asp Leu Ser Gly Ala Leu Asn Glu Leu Gln Asp Glu Ala
     50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                 85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Gly Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 25
<211> LENGTH: 795
<212> TYPE: DNA
<213> ORGANISM: Artificial sequence

```
-continued

<220> FEATURE:
<223> OTHER INFORMATION: Neomycin mutant D208G

<400> SEQUENCE: 25
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcaggggc gcccggttct ttttgtcaag accgacctgt ccggtgccct gaatgaactg   180
caagacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgag catgcccgac   540
ggcgaggatc tcgtcgtgac ccatggcgat gcctgcttgc cgaatatcat ggtggaaaat   600
ggccgctttt ctggattcat cggctgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
gacgagttct tctga                                                    795

<210> SEQ ID NO 26
<211> LENGTH: 264
<212> TYPE: PRT
<213> ORGANISM: Artificial sequence
<220> FEATURE:
<223> OTHER INFORMATION: Neomycin mutant D208G

<400> SEQUENCE: 26

Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
    65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
               100                 105                 110

Val Ser Ile Met Ala Asp Ala Met Arg Arg Leu His Thr Leu Asp Pro
           115                 120                 125

Ala Thr Cys Pro Phe Asp His Gln Ala Lys His Arg Ile Glu Arg Ala
       130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
               165                 170                 175

Ser Met Pro Asp Gly Glu Asp Leu Val Val Thr His Gly Asp Ala Cys
           180                 185                 190

Leu Pro Asn Ile Met Val Glu Asn Gly Arg Phe Ser Gly Phe Ile Gly
```

```
                    195                 200                 205
Cys Gly Arg Leu Gly Val Ala Asp Arg Tyr Gln Asp Ile Ala Leu Ala
            210                 215                 220
Thr Arg Asp Ile Ala Glu Glu Leu Gly Gly Glu Trp Ala Asp Arg Phe
225                 230                 235                 240
Leu Val Leu Tyr Gly Ile Ala Ala Pro Asp Ser Gln Arg Ile Ala Phe
                245                 250                 255
Tyr Arg Leu Leu Asp Glu Phe Phe
            260

<210> SEQ ID NO 27
<211> LENGTH: 21
<212> TYPE: DNA
<213> ORGANISM: Artificial sequence
<220> FEATURE:
<223> OTHER INFORMATION: Oligonucleotide Neofor5

<400> SEQUENCE: 27
ttccagaagt agtgaggagg c                                          21

<210> SEQ ID NO 28
<211> LENGTH: 19
<212> TYPE: DNA
<213> ORGANISM: Artificial sequence
<220> FEATURE:
<223> OTHER INFORMATION: Oligonucleotide Neorev5

<400> SEQUENCE: 28
atggcaggtt gggcgtcgc                                             19

<210> SEQ ID NO 29
<211> LENGTH: 21
<212> TYPE: DNA
<213> ORGANISM: Artificial sequence
<220> FEATURE:
<223> OTHER INFORMATION: Oligonucleotide Neofor2

<400> SEQUENCE: 29
gaactgttcg ccaggctcaa g                                          21

<210> SEQ ID NO 30
<211> LENGTH: 22
<212> TYPE: DNA
<213> ORGANISM: Artificial sequence
<220> FEATURE:
<223> OTHER INFORMATION: Oligonucleotide IC49

<400> SEQUENCE: 30
cggcaaaatc ccttataaat ca                                         22

<210> SEQ ID NO 31
<211> LENGTH: 20
<212> TYPE: DNA
<213> ORGANISM: Artificial sequence
<220> FEATURE:
<223> OTHER INFORMATION: Oligonucleotide E182Gfor

<400> SEQUENCE: 31
gacggcgggg atctcgtcgt                                            20

<210> SEQ ID NO 32
<211> LENGTH: 20
<212> TYPE: DNA
<213> ORGANISM: Artificial sequence
<220> FEATURE:
```

<223> OTHER INFORMATION: Oligonucleotide E182Grev

<400> SEQUENCE: 32
acgacgagat ccccgccgtc                                             20

<210> SEQ ID NO 33
<211> LENGTH: 23
<212> TYPE: DNA
<213> ORGANISM: Artificial sequence
<220> FEATURE:
<223> OTHER INFORMATION: Oligonucleotide W91Afor

<400> SEQUENCE: 33
gggaagggac gcgctgctat tgg                                         23

<210> SEQ ID NO 34
<211> LENGTH: 23
<212> TYPE: DNA
<213> ORGANISM: Artificial sequence
<220> FEATURE:
<223> OTHER INFORMATION: Oligonucleotide W91Arev

<400> SEQUENCE: 34
ccaatagcag cgcgtccctt ccc                                         23

<210> SEQ ID NO 35
<211> LENGTH: 24
<212> TYPE: DNA
<213> ORGANISM: Artificial sequence
<220> FEATURE:
<223> OTHER INFORMATION: Oligonucleotide V198Gfor

<400> SEQUENCE: 35
ccgaatatca tggggaaaa tggc                                         24

<210> SEQ ID NO 36
<211> LENGTH: 24
<212> TYPE: DNA
<213> ORGANISM: Artificial sequence
<220> FEATURE:
<223> OTHER INFORMATION: Oligonucleotide V198Grev

<400> SEQUENCE: 36
gccattttcc cccatgatat tcgg                                        24

<210> SEQ ID NO 37
<211> LENGTH: 21
<212> TYPE: DNA
<213> ORGANISM: Artificial sequence
<220> FEATURE:
<223> OTHER INFORMATION: Oligonucleotide D227Afor

<400> SEQUENCE: 37
ctacccgtgc tattgctgaa g                                           21

<210> SEQ ID NO 38
<211> LENGTH: 21
<212> TYPE: DNA
<213> ORGANISM: Artificial sequence
<220> FEATURE:
<223> OTHER INFORMATION: Oligonucleotide D227Arev

<400> SEQUENCE: 38
cttcagcaat agcacgggta g                                           21

<210> SEQ ID NO 39

```
<211> LENGTH: 21
<212> TYPE: DNA
<213> ORGANISM: Artificial sequence
<220> FEATURE:
<223> OTHER INFORMATION: Oligonucleotide D227Vfor

<400> SEQUENCE: 39
ctacccgtgt tattgctgaa g                                              21

<210> SEQ ID NO 40
<211> LENGTH: 21
<212> TYPE: DNA
<213> ORGANISM: Artificial sequence
<220> FEATURE:
<223> OTHER INFORMATION: Oligonucleotide D227Vrev

<400> SEQUENCE: 40
cttcagcaat aacacgggta g                                              21

<210> SEQ ID NO 41
<211> LENGTH: 24
<212> TYPE: DNA
<213> ORGANISM: Artificial sequence
<220> FEATURE:
<223> OTHER INFORMATION: Oligonucleotide D261Gfor

<400> SEQUENCE: 41
gccttcttgg cgagttcttc tgag                                           24

<210> SEQ ID NO 42
<211> LENGTH: 24
<212> TYPE: DNA
<213> ORGANISM: Artificial sequence
<220> FEATURE:
<223> OTHER INFORMATION: Oligonucleotide D261Grev

<400> SEQUENCE: 42
ctcagaagaa ctcgccaaga aggc                                           24

<210> SEQ ID NO 43
<211> LENGTH: 24
<212> TYPE: DNA
<213> ORGANISM: Artificial sequence
<220> FEATURE:
<223> OTHER INFORMATION: Oligonucleotide D261Nfor

<400> SEQUENCE: 43
gccttcttaa cgagttcttc tgag                                           24

<210> SEQ ID NO 44
<211> LENGTH: 24
<212> TYPE: DNA
<213> ORGANISM: Artificial sequence
<220> FEATURE:
<223> OTHER INFORMATION: Oligonucleotide D261Nrev

<400> SEQUENCE: 44
ctcagaagaa ctcgttaaga aggc                                           24

<210> SEQ ID NO 45
<211> LENGTH: 22
<212> TYPE: DNA
<213> ORGANISM: Artificial sequence
<220> FEATURE:
<223> OTHER INFORMATION: Oligonucleotide F240Ifor

<400> SEQUENCE: 45
```

```
ggctgaccgc atcctcgtgc tt                                              22
```

<210> SEQ ID NO 46
<211> LENGTH: 22
<212> TYPE: DNA
<213> ORGANISM: Artificial sequence
<220> FEATURE:
<223> OTHER INFORMATION: Oligonucleotide F240Irev

<400> SEQUENCE: 46

```
aagcacgagg atgcggtcag cc                                              22
```

<210> SEQ ID NO 47
<211> LENGTH: 20
<212> TYPE: DNA
<213> ORGANISM: Artificial sequence
<220> FEATURE:
<223> OTHER INFORMATION: Oligonucleotid E182Dfor

<400> SEQUENCE: 47

```
gacggcgatg atctcgtcgt                                                 20
```

<210> SEQ ID NO 48
<211> LENGTH: 20
<212> TYPE: DNA
<213> ORGANISM: Artificial sequence
<220> FEATURE:
<223> OTHER INFORMATION: Oligonucleotide E182Drev

<400> SEQUENCE: 48

```
acgacgagat catcgccgtc                                                 20
```

<210> SEQ ID NO 49
<211> LENGTH: 19
<212> TYPE: DNA
<213> ORGANISM: Artificial sequence
<220> FEATURE:
<223> OTHER INFORMATION: Oligonucleotide D190Gfor

<400> SEQUENCE: 49

```
catggcggtg cctgcttgc                                                  19
```

<210> SEQ ID NO 50
<211> LENGTH: 19
<212> TYPE: DNA
<213> ORGANISM: Artificial sequence
<220> FEATURE:
<223> OTHER INFORMATION: Oligonucleotide D190Grev

<400> SEQUENCE: 50

```
gcaagcaggc accgccatg                                                  19
```

<210> SEQ ID NO 51
<211> LENGTH: 19
<212> TYPE: DNA
<213> ORGANISM: Artificial sequence
<220> FEATURE:
<223> OTHER INFORMATION: Oligonucleotide D208Gfor

<400> SEQUENCE: 51

```
gattcatcgg ctgtggccg                                                  19
```

<210> SEQ ID NO 52
<211> LENGTH: 19
<212> TYPE: DNA
<213> ORGANISM: Artificial sequence
<220> FEATURE:

-continued

<223> OTHER INFORMATION: Oligonucleotide D208Grev

<400> SEQUENCE: 52
cggccacagc cgatgaatc                                               19

<210> SEQ ID NO 53
<211> LENGTH: 21
<212> TYPE: DNA
<213> ORGANISM: Artificial sequence
<220> FEATURE:
<223> OTHER INFORMATION: Oligonucleotide D227Gfor

<400> SEQUENCE: 53
ctacccgtgg tattgctgaa g                                            21

<210> SEQ ID NO 54
<211> LENGTH: 21
<212> TYPE: DNA
<213> ORGANISM: Artificial sequence
<220> FEATURE:
<223> OTHER INFORMATION: Oligonucleotide D227Grev

<400> SEQUENCE: 54
cttcagcaat accacgggta g                                            21

<210> SEQ ID NO 55
<211> LENGTH: 2406
<212> TYPE: DNA
<213> ORGANISM: Cricetulus griseus
<300> PUBLICATION INFORMATION:
<310> PATENT DOCUMENT NUMBER: PCT/EP/96/04631
<311> PATENT FILING DATE: 1996-10-24
<312> PUBLICATION DATE: 1997-05-01

<400> SEQUENCE: 55
gatctccagg acagccatgg ctattacaca gagaaaccct gtctggaaaa acaaaaaatt    60
agtgtccatg tgtaaatgtg tggagtatgc ttgtcatgcc acatacagag gtagagggca   120
gtttatggga gtcagttcct attcttcctt tatgggggac ctgggactg aactcaggtc    180 atcaggcttg gcagaaagtg cattagctca cggagcctta tcattggcga aagctctctc   240
aagtagaaaa tcaatgtgtt tgctcatagt gcaatcatta tgtttcgaga ggggaagggt   300
acaatcgttg gggcatgtgt ggtcacatct gaatagcagt agctccctag agaattcca    360 agttctttgg tggtgtatca atgcccttaa aggggtcaac aacttttttt ccctctgaca   420
aaactatctt cttatgtcct tgtccctcat atttgaagta ttttattctt tgcagtgttg   480
aatatcaatt ctagcacctc agacatgtta ggtaagtacc ctacaactca ggttaactaa   540
tttaatttaa ctaatttaac cccaacactt tttctttgtt tatccacatt tgtgagtgt    600 gtgtgtgtgt gtgtgtgt gtgtgtgt gtgtgtgt gtgtgtgt gtgtgtgc             660 gcgcgcgcgc gcgctcggat cattctacct tttgtttaaa aaatgttagt ccaggggtgg   720
ggtgcactgt gaaagtctga gggtaacttg ctggggtcag ttctttccac tataggacag   780
aactccaggt gtcaactctt tactgacaga accatccaaa tagccctatc taattttagt   840
ttttatttta tttatttttt gttttcgag acagggtttc tctgtggctt tggaggctgt   900
cctggaacta gctcttgtag accaggctgg tctcgaactc agatccac ctgcctctgc     960 ctcctgagtg ctgggattaa aggcatgcgc caccaacgct tggctctacc taattttaaa  1020
agagattgtg tgtcacaagg gtgtcatgtc gccctgcaac cacccccccc ccaaaaaaaa  1080
aaaaaaaaaa acttcactga agctgaagca cgatgatttg gttactctgg ctggccaatg  1140

-continued

```
agctctaggg agtctcctgt caaacagaat ctcaacaggc gcagcagtct ttttaaagt    1200 ggggttacaa cacaggtttt tgcatatcag gcattttatc taagctattt cccagccaaa    1260
aatgtgtatt ttggaggcag cagagctaat agattaaaat gagggaagag cccacacagg    1320
ttattaggaa gataagcatc ttctttatat aaaacaaaac caaaccaaac tggaggaggt    1380
ctacctttag ggatggaaga aaagacattt agagggtgca atagaaaggg cactgagttt    1440
gtgaggtgga ggactgggag agggcgcaac cgctttaact gtcctgtttt gcctattttt    1500
tggggacagc acatgttcct atttttccca ggatgggcaa tctccacgtc caaacttgcg    1560
gtcgaggact acagtcattt tgcaggtttc cttactgtat ggcttttaaa acgtgcaaag    1620
gtgaccatta accgtttcac gctgggaggg cacgtgcggc tcagatgctt cctctgactg    1680
agggccagga gggggctaca cggaagaggc cacacccgca cttgggaaga ctcgatttgg    1740
gcttcagctg gctgagacgc cccagcaggc tcctcggcta caccttcagc cccgaatgcc    1800
ttccggccca taaccettcc cttctaggca tttccggcga ggacccaccc tcgcgccaaa    1860
cattcggccc catccccgg tcctcacctg aatctctaac tctgactcca gagtttagag    1920
actataacca gatagcccgg atgtgtggaa ctgcatcttg ggacgagtag ttttagcaaa    1980
aagaaagcga cgaaaaacta caattcccag acagacttgt gttacctctc ttctcatgct    2040
aaacaagccc cctttaaagg aaagcccctc ttagtcgcat cgactgtgta agaaaggcgt    2100
ttgaaacatt ttaatgttgg gcacaccgtt tcgaggaccg aaatgagaaa gagcatagg    2160 aaacggagcg cccgagctag tctggcactg cgttagacag ccgcggtcgt tgcagcgggc    2220
aggcacttgc gtggacgcct aagggggcggg tctttcggcc gggaagcccc gttggtccgc    2280
gcggctcttc ctttccgatc cgccatccgt ggtgagtgtg tgctgcgggc tgccgctccg    2340 gcttgggget tcccgcgtcg ctctcaccct ggtcggcggc tctaatccgt ctcttttcga    2400
atgtag                                                              2406
```

NEOMYCIN-PHOSPHOTRANSFERASE-GENES AND METHODS FOR THE SELECTION OF RECOMBINANT CELLS PRODUCING HIGH LEVELS OF A DESIRED GENE PRODUCT

RELATED APPLICATIONS

This application is a Continuation of U.S. application Ser. No. 10/724,301 filed Nov. 26, 2003, which claims priority benefits of DE 102 56 081, filed Nov. 29, 2002; DE 103 30 686, filed July 8, 2003; U.S. Non-Provisional Application No. 10/724,301, filed Nov. 26, 2003, U.S. Provisional Application Nos. 60/431,535 and 60/487,902, filed Dec. 6, 2002 and Jul. 17, 2003, respectively, all of which are incorporated by reference herein.

BACKGROUND OF THE INVENTION

The invention relates to new modified neomycin-phosphotransferase genes and their use in selection methods for high-producing recombinant cells. Accordingly, the present invention also relates to new expression vectors which contain a modified neomycin-phosphotransferase gene, preferably combined with a gene of interest functionally linked to a heterologous promoter. The invention further relates to methods of preparing heterologous gene products using the corresponding high-producing recombinant cells.

Mammalian cells are the preferred host cells for the production of complex biopharmaceutical proteins as the modifications carried out post-translationally are compatible with humans both functionally and pharmacokinetically. The main relevant cell types are hybridoma, myeloma CHO (Chinese Hamster Ovary) cells and BHK (Baby Hamster Kidney) cells. The cultivation of the host cells is increasingly carried out under serum- and protein-free production conditions. The reasons for these are the concomitant cost reduction, the reduced interference in the purification of the recombinant protein and the reduction in the potential for the introduction of pathogens (e.g. prions and viruses). The use of CHO cells as host cells is becoming more widespread as these cells adapt to suspension growth in serum- and protein-free medium and are also regarded and accepted as safe production cells by the regulatory authorities.

In order to produce a stable mammalian cell line which expresses a heterologous gene of interest (GOI), the heterologous gene is generally inserted in the desired cell line together with a selectable marker gene such as e.g. neomycin phosphotransferase (NPT) by transfection. The heterologous gene and the selectable marker gene can be expressed in a host cell starting from one individual or separate co-transfected vectors. Two to three days after transfection the transfected cells are transferred into medium containing a selective agent, e.g. G418 when using neomycin phosphotransferase-gene (NPT gene), and cultivated for some weeks under these selective conditions. The emerging resistance cells which have integrated the exogenous DNA can be isolated and investigated for expression of the desired gene product (of the GOI).

A major problem in establishing cell lines with a high expression of the desired proteins arises from the random and undirected integration of the recombinant vector into transcriptionally-active or transcriptionally-inactive loci in the host cell genome. As a result a population of cells is obtained which have completely different expression rates of the heterologous gene, the productivity of the cells generally following normal distribution. In order to identify cell clones which have a very high expression of the heterologous gene of interest it is therefore necessary to examine and test a large number of clones, which is time consuming, labour intensive and expensive. Improvements to the vector system used for transfection therefore set out to increase the proportion of high producers in the transfected cell population by suitable selection strategies and thereby reduce the expenditure and work involved in clone identification. The development of such an expression system is the subject of the present invention.

The amino glycoside-3'-phosphotransferase II enzyme (neomycin-phosphotransferase) (EC27195) the gene of which is transposon 5-associated in *Escherichia coli* is used as a selectable marker in a number of organisms (e.g. bacteria, yeasts, plants and mammalian cells). This enzyme confers resistance to various aminoglycoside antibiotics such as neomycin, kanamycin and G418, by inactivating the antibiotics by transferring the terminal phosphate from ATP to the 3' hydroxyl group of the aminohexose ring I. In addition to the wild-type neomycin phosphotransferase some mutants are known which have reduced phosphotransferase activity and hence reduced resistance to aminoglycoside antibiotics in bacteria (Blázques, J. et al., *Molecular Microbiology* 1991, 5(6), 1511-1518; Kocabiyik, S. et al., *Biochem Biophys Res Commun* 1992, 185(3), 925-931; Yenofsky, R. L. et al., *Proc Natl Acad Sci USA* 1990, 87, 3435-3439) and in slices of leaf from tobacco (Yenofsky, R. L. et al., *Proc Nat/Acad Sci USA* 1990, 87, 3435-3439).

One of these mutants (Glu182Asp) was used as a marker for selecting embryonic stem cells, the neomycin phosphotransferase gene being integrated into the c-myc gene by targeted homologous recombination (gene targeting) (Hanson, K. D. et al., *Mol Cell Biol* 1995, 15(1), 45-51). The authors restrict themselves to the use of the modified enzyme for gene targeting.

Patent application WO 99/53046 describes the expression of a modified neomycin phosphotransferase gene (Asp261Asn) in production-relevant mammalian cells. The authors describe a non-cloning method for expression of a gene of interest in mammalian cells. By cotransfection of the cells with three individual DNA fragments which code for a promoter element, a gene of interest and a selectable marker coupled with an IRES ("Internal ribosomal entry site") element, it is possible to deliberately grow cells, under selection pressure, in which all three DNA fragments are combined as a functional bicistronic transcription unit (promoter gene of interest-IRES-neomycin-phosphotransferase gene). The arrangement of the elements only occurs in the transfected cell, so that only a few cells show the correct arrangement of the elements. Moreover, after gene amplification, using an amplifiable selectable marker, no high producing clones can be generated. After repeated selection and gene amplification the cells generated exhibited at most 6 pg of protein per cell per day (6 pg/cell/day).

None of the publications discloses modified neomycin phosphotransferase genes with particular suitability for the preparation of a high expression vector system for mammalian cells which makes it possible to develop high producing cells in order to prepare recombinant biopharmaceutical proteins which contain one or more complete functional transcription units both for one or more genes of interest and also for a modified neomycin phosphotransferase gene with reduced antibiotic resistance. The DNA construct described in WO 99/53046 contains only a promoter-less neomycin gene functionally linked to the gene for dihydrofolate reductase (DHFR).

There is therefore a need to make suitable modified neomycin phosphotransferase genes available, particularly for the development of corresponding high expression vector systems for biopharmaceutical processes. The problem of the present invention was therefore to provide corresponding new modified neomycin phosphotransferase genes, expression vectors which contain a modified neomycin phosphotransferase gene and a gene of interest functionally linked to a heterologous promoter, a method of selection for high producing recombinant cells, preferably for mammalian cells, and a process for producing heterologous gene products.

Surprisingly, within the scope of the present invention, it has been possible to produce and identify new modified highly selective neomycin phosphotransferase genes which are characterised by their particular suitability for the selection of high producing cells.

SUMMARY OF THE INVENTION

The present invention provides new modified neomycin phosphotransferase genes. Surprisingly, it has been found that an enrichment of transfected mammalian cells with high expression rates of the co-integrated gene of interest could be achieved by using the modified neomycin phosphotransferase genes described hereinafter as selectable markers. Compared with the use of the wild-type neomycin phosphotransferase as selectable marker, after transfection with one of the new neomycin phosphotransferase genes according to the invention the cells exhibited a productivity of a protein (an antibody) which was increased by a factor 1.4 to 14.6.

The modified neomycin phosphotransferase genes according to the invention are preferably mutants which code for a different amino acid from the wild-type gene at amino acid position 91, 182, 198, 227, 240 or 261. In a preferred embodiment the neomycin phosphotransferase gene according to the invention is the mutant Glu182Gly, Glu182Asp, Trp91Ala, Val198Gly, Asp227Ala, Asp227Val, Asp227Gly, Asp261Asn, Asp261Gly or Phe240Ile. For selecting high producing mammalian cells it has proved particularly suitable to use the mutants Trp91Ala, Asp227Val, Asp261Asn, Asp261Gly and Phe240Ile, while the mutants Asp227Val and Asp261Gly in turn gave cell clones with the highest productivity and are therefore particularly preferred.

The high-producing cells were obtained by the use of a eukaryotic expression vector which contains a heterologous gene of interest functionally linked to a heterologous promoter and a modified neomycin phosphotransferase gene according to the invention. The expression vector preferably contains other regulatory elements, e.g. one or more enhancers functionally linked to the promoter or promoters. Expression vectors are also preferred which additionally contain a gene for a fluorescent protein which is functionally linked to the gene of interest and the heterologous promoter, preferably via an internal ribosomal entry site (IRES), which enables bicistronic expression of the gene which codes for a fluorescent protein and of the gene which codes for a protein/product of interest, under the control of the heterologous promoter. Particularly suitable are expression vectors in which the heterologous gene of interest is under the control of the ubiquitin/S27a promoter.

The invention also relates to expression vectors which instead of the gene of interest contain a multiple cloning site for incorporating such a gene, i.e. a sequence section with multiple recognition sequences for restriction endonucleases.

In another aspect the invention relates to recombinant mammalian cells which contain one of the above-mentioned modified neomycin phosphotransferase genes according to the invention. In addition the present invention relates to recombinant mammalian cells which have been transfected with one of the expression vectors according to the invention.

These are preferably recombinant rodent cells, of which recombinant hamster cells such as e.g. CHO cells or BHK cells are particularly preferred. In another preferred embodiment the said recombinant cells are additionally transfected with the gene for an amplifiable selectable marker, e.g. with the gene of dihydrofolate reductase (DHFR).

The invention also relates to a process for enriching recombinant mammalian cells which express a modified neomycin phosphotransferase gene, characterised in that (i) a pool of mammalian cells is transfected with a gene for a modified neomycin phosphotransferase, which has only 1 to 80%, preferably only 1 to 60%, more preferably only 1.5 to 30%, most preferably only 1.5 to 26% of the activity and/or one of the modifications described above; (ii) the mammalian cells are cultivated under conditions which allow expression of the modified neomycin phosphotransferase gene; and (iii) the mammalian cells are cultivated in the presence of at least one selecting agent which acts selectively on the growth of mammalian cells, and gives preference to the growth of those cells which express the neomycin phosphotransferase gene.

The invention also relates to a process for the expression of at least one gene of interest in recombinant mammalian cells, characterised in that (i) a pool of mammalian cells is transfected with at least one gene of interest and one gene for a modified neomycin phosphotransferase which exhibits only 1 to 80%, preferably only 1 to 60%, more preferably only 1.5 to 30%, most preferably only 1.5 to 26% of the activity and/or one of the modifications described above; (ii) the cells are cultivated under conditions which allow expression of the gene or genes of interest and the modified neomycin phosphotransferase gene; (iii) the mammalian cells are cultivated in the presence of at least one selecting agent which acts selectively on the growth of mammalian cells and gives preference to the growth of those cells which express the neomycin phosphotransferase gene; and (iv) the protein or proteins of interest is or are obtained from the mammalian cells or from the culture supernatant.

The present invention further relates to a process for obtaining and selecting recombinant mammalian cells which express at least one heterologous gene of interest, which is characterised in that (i) recombinant mammalian cells are transfected with an expression vector according to the invention which in addition to the gene of interest and the modified neomycin phosphotransferase gene codes for a fluorescent protein; (ii) the mammalian cells are cultivated under conditions which allow expression of the gene or genes of interest, the gene which codes for a fluorescent protein and the modified neomycin phosphotransferase gene; (iii) the mammalian cells are cultivated in the presence of at least one selecting agent which acts selectively on the growth of mammalian cells and gives preference to the growth of those cells which express the neomycin phosphotransferase gene; and (iv) the mammalian cells are sorted by flow-cytometric analysis.

If the mammalian cells have additionally been transfected with a gene for an amplifiable selectable marker gene, e.g. the DHFR gene, it is possible to cultivate the mammalian cells under conditions in which the amplifiable selectable marker gene is also expressed, and to add to the culture medium a selecting agent which results in amplification of the amplifiable selectable marker gene.

Preferably, the processes according to the invention are carried out with mammalian cells which are adapted to growth in suspension, i.e. with mammalian cells which are cultivated in a suspension culture. Other embodiments relate to processes in which the mammalian cells, preferably those which are adapted to growth in suspension, are cultivated under serum-free conditions.

DESCRIPTION OF THE FIGURES

FIG. 4 shows conserved domains and the position of the inserted NPT mutations within the NPT amino acid sequence (SEQ ID NO:2). On the basis of sequence homologies between different aminoglycoside-modified enzymes, different conserved domains were identified within the NPT protein sequence (shown in grey) The three motifs in the C-terminal region of the enzyme obviously have special functions. Motifs 1 and 2 are presumably involved in the catalytic transfer of the terminal phosphate in the ATP catalysis or the nucleotide binding, whereas motif 3 is thought to have a function in the ATP hydrolysis and/or the change in conformation in the enzyme-aminoglycoside complex. Amino acids which occur in at least 70% of the aminoglycoside-modifying enzymes are emphasised in bold type. The singly underlined amino acids are assigned to the same group on the basis of their similarity and occur in at least 70% of the aminoglycoside-modifying enzymes Amino acids marked with an asterisk indicate the position of the mutation sites.

Genomic DNA (10 μg, 5 μg, 2.5 μg, 1.25 μg, 0.63 μg and 0.32 μg) was hybridised with an FITC-dUTP-labelled PCR product which included the coding region of the NPT gene. Untransfected CHO-DG44 cells were used as the negative control. The plasmid pBIN-LC was used as the standard (320 pg, 160 pg, 80 pg, 40 pg, 20 pg, 10 pg, 5 pg, 2.5 pg). The copy number of the npt genes in the cell pools was calculated using the standard series which had been determined from the signal intensities measured for the titrated plasmid-DNA.

Figure 11:
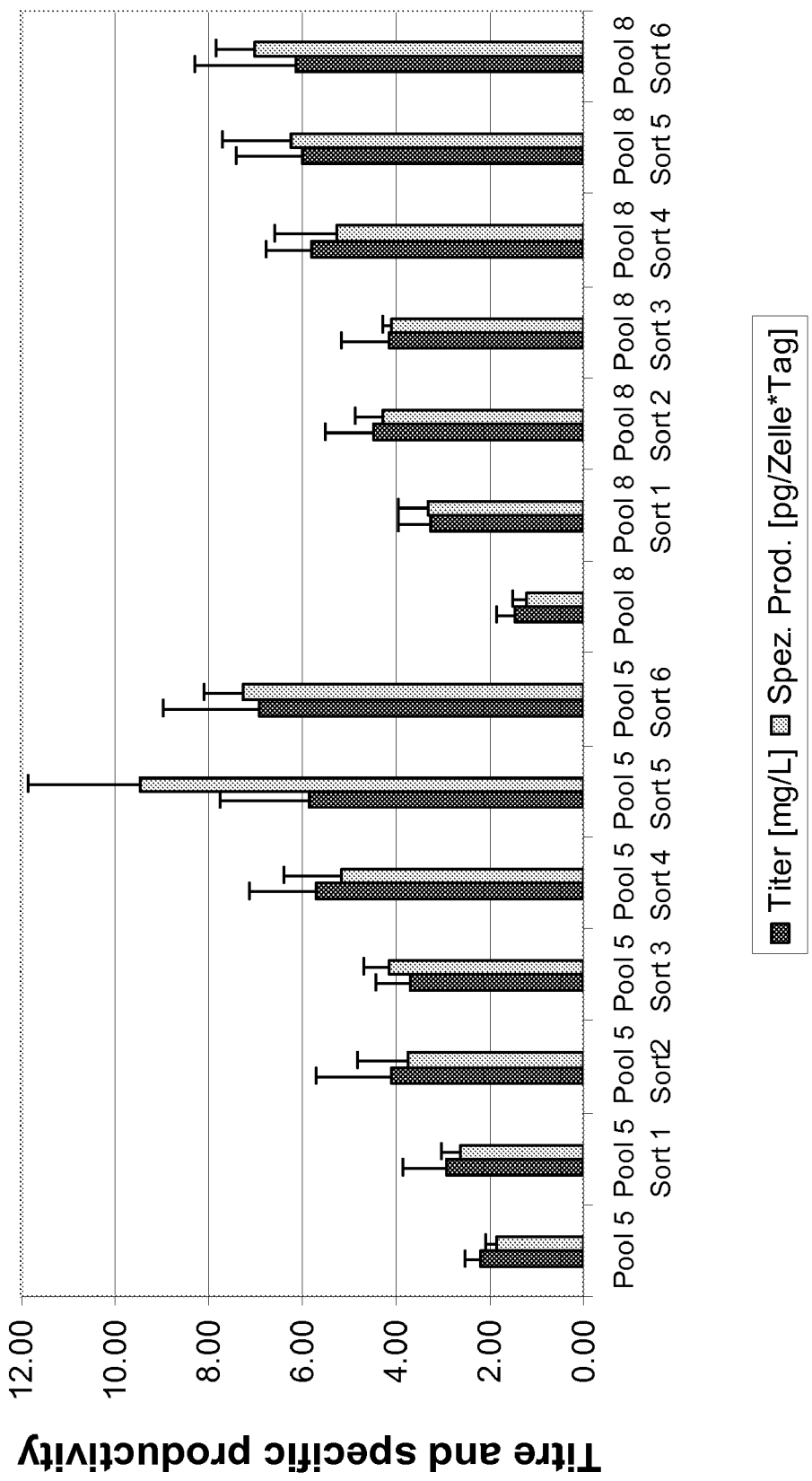

FIG. 11 shows the isolation of high-expressing mAb cell pools by a GFP-based selection using FACS taking as the example two cell pools (cell pool 5 and 8). These cell pools, obtained from the co-transfection with the vectors pBID-HC and pBING-LC, were subjected to sequential GFP-based FACS sorting. The concentration of the IgG2 antibody in the cell culture supernatant of the pools was determined by ELISA after each sorting step and the specific productivity per cell and per day (pg/cell/day) was calculated. In all 6 sorts were done, and in each case the 5% of cells with the highest GFP fluorescence were sorted out. Each data point represents the average of at least six cultivation runs in 75 cm² flasks.

Figure 12:
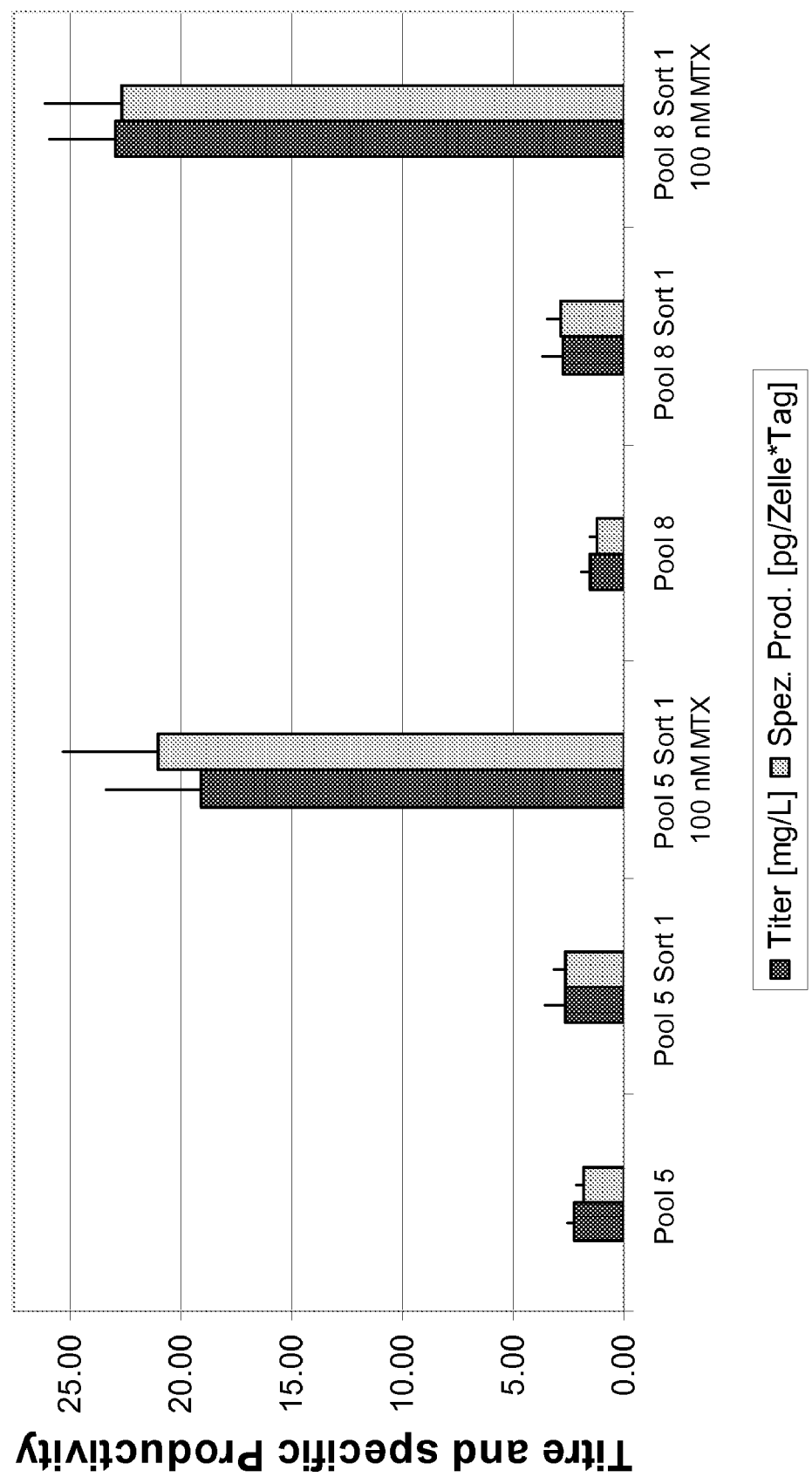

FIG. 12 shows the increases in mAb productivity achieved by combining a GFP-based selection with an MTX amplification step taking as the example cell pools 5 and 8 (cf. FIG. 11). Two weeks after the co-transfection of CHO-DG44 with the vectors pBID-HC and pBING-LC the 5% of cells with the highest GFP fluorescence were sorted out from pools 5 and 8. Then dhfr-mediated gene amplification was carried out by adding 100 nM of methotrexate (MTX) to the culture medium. The concentration of the mAb in the cell culture supernatant of the pools was determined by ELISA and the specific productivity per cell and per day (pg/cell/day) was calculated. Each data point represents the average of at least six cultivation runs in 75 cm² flasks.

Figure 13:
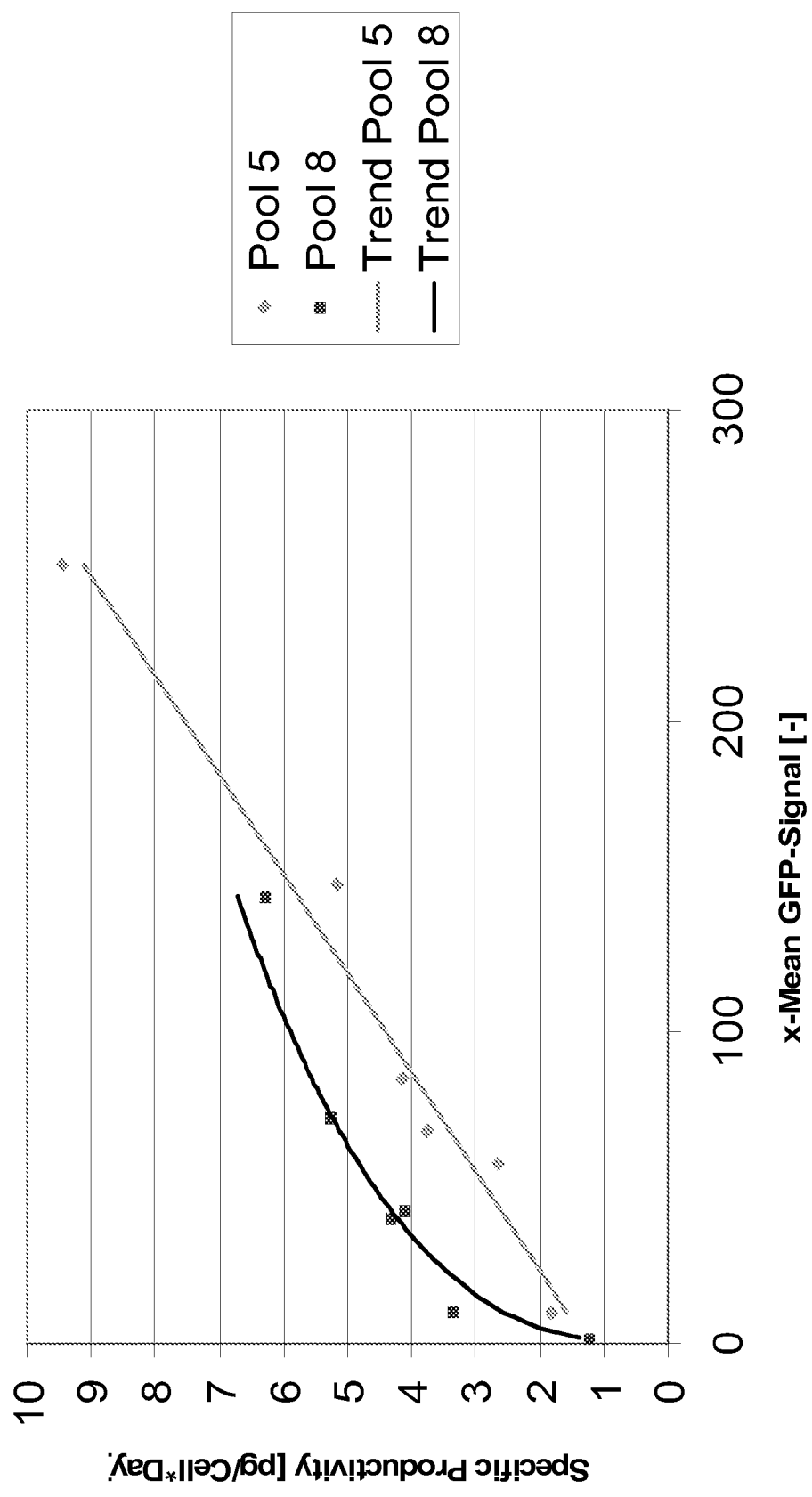

FIG. 13 shows the correlation between the antibody productivity and the GFP fluorescence taking as the example cell pools 5 and 8 (cf. FIG. 11). These cell pools were obtained by transfecting CHO-DG44 with the vector combination pBID-HC and pBING-LC. They were subjected to sequential GFP-based FACS sorting, and the 5% of cells with the highest GFP fluorescence were sorted out. The concentration of the IgG2 antibody in the cell culture supernatant of the pools was determined by ELISA after each sorting step and the specific productivity per cell and per day (pg/cell/day) was calculated. Each data point represents the average of at least six cultivation runs in 75 cm² flasks.

DETAILED DESCRIPTION OF THE INVENTION

The following information on the amino acid positions relates in each case to the position of the amino acid as coded by the wild-type neomycin phosphotransferase gene with SEQ ID NO:1. As used herein, "a", "an", and "the" refer to one or more entities, e.g., "a mammalian cell" refers to one or more mammalian cells. By a "modified neomycin phosphotransferase gene" is meant a nucleic acid which codes for a polypeptide with neomycin phosphotransferase activity, the polypeptide having a different amino acid from the wild-type protein at least one of the amino acid positions described more fully in the specification which are homologous to the wild-type protein with SEQ ID NO:2. In this context the term "homologous" means that the sequence region carrying the mutation can be brought into correspondence with a reference sequence, in this case the sequence of the wild-type neomycin phosphotransferase according to SEQ ID NO:2, using so-called standard "alignment" algorithms, such as for example "BLAST" (Altschul, S. F., Gish, W., Miller, W., Myers, E. W. and Lipman, D. J. (1990) "Basic local alignment search tool." J. Mol. Biol. 215:403-410; Gish, W. and States, D. J. (1993) "Identification of protein coding regions by database similarity search." Nature Genes. 3:266-272; Madden, T. L., Tatusov, R. L. and Zhang, J. (1996) "Applications of network BLAST server" Meth. Enzymol. 266:131-141; Zhang, J. and Madden, T. L. (1997) "PowerBLAST: A new network BLAST application for interactive or automated sequence analysis and annotation." Genome Res. 7:649-656; Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402). Sequences are in correspondence when they correspond in their sequence order and can be identified using the standard "alignment" algorithms.

The present invention provides new modified neomycin phosphotransferase genes and methods of preparing and selecting mammalian cell lines which allow a high expression of heterologous gene products, preferably biopharmaceutically relevant polypeptides or proteins. The processes according to the invention are based primarily on the selection of cells which in addition to the gene of interest express a neomycin phosphotransferase gene according to the invention which gives the transfected cells a selective advantage over non-transfected cells. Surprisingly, it has been found that the use of the modified neomycin phosphotransferase genes (mNPT genes) according to the invention described herein has a substantial selective advantage over the wild-type neomycin phosphotransferase gene (wtNPT gene). This particularly relates to the use of mutants which have a lower enzyme activity compared with wtNPT.

Modified Neomycin Phosphotransferase Genes According to the Invention

It has proved particularly suitable to use modified NPT genes which code for an NPT having only 1 to 80%, preferably only 1 to 60% of the enzyme activity of wtNPT. Preferred NPT mutants are those which have only 1 to 30% of the enzyme activity of wtNPT, while those which have only 1.5 to 26% of the enzyme activity of wtNPT are particularly preferred. The enzyme activity of an NPT can be determined for example in a dot assay as described in Example 4 and given as Method 5.

The term wild-type neomycin phosphotransferase refers to a neomycin phosphotransferase gene which codes for the aminoglycoside-3'-phosphotransferase II enzyme (EC 2.7.1.95) the gene of which is naturally transposon 5-associated in *Escherichia coli*, and contains for example the amino acid sequence given in SEQ ID NO:2 or is coded by the nucleotide sequence given in SEQ ID NO:1. This enzyme gives resistance to various aminoglycoside antibiotics such as neomycin, kanamycin and G418, by inactivating the antibiotics by the transfer of the terminal phosphate of ATP to the 3' hydroxyl group of the amino hexose ring 1. The term wtNPT also refers to all NPTs which have a comparable enzyme activity to the NPT coded by SEQ ID NO:1. This includes in particular those NPTs in which the enzymatically active centre which catalyses the transfer of a terminal phosphate from ATP to a substrate is present in an identical or nearly identical conformation (Shaw, K. J. et al., Microbiological Reviews 1993, 57(1), 138-163; Hon, W. et al., Cell 1997, 89, 887-895; Burk, D. L. et al., Biochemistry 2001, 40 (30), 8756-8764) and thus has a comparable enzyme activity to an enzyme which contains the amino acid sequence of SEQ ID NO:2. A wtNPT has a comparable enzyme activity if it exhibits about 81 to 150%, preferably 90 to 120% of the enzyme activity displayed by an NPT defined by SEQ ID NO:2, while the activity can be determined in the dot assay described in Example 4 and referred to as Method 5.

Fundamentally preferred are mutants wherein the reduction in the enzyme activity compared with wtNPT is based on a modification of the amino acid sequence, e.g. on the substitution, insertion or deletion of at least one or more amino acids. Deletion, insertion and substitution mutants can be produced by "site-specific mutagenesis" and/or "PCR-based mutagenesis techniques". Suitable methods are described for example by Lottspeich and Zorbas (Lottspeich and Zorbas eds. Bioanalytic, Spektrum Akad. Verl., 1998, Chapter 36.1 with other references).

Surprisingly, it has been found that if neomycin phosphotransferase mutants are used as selectable markers in which at least the amino acid tryptophan at amino acid position 91, the amino acid glutamic acid at amino acid position 182, the amino acid valine at amino acid position 198, the amino acid aspartic acid at amino acid position 227, the amino acid aspartic acid at amino acid position 261 or the amino acid phenylalanine at amino acid position 240 has been altered compared with wtNPT, it is possible to achieve particularly effective enrichment of transfected mammalian cells with a high expression rate for the co-integrated gene of interest. Accordingly, mutants which affect the amino acids at positions 91, 182, 198, 227 and/or 240 are preferred. Particularly advantageous are substitution mutants, i.e. mutants in which the amino acid occurring at this location in the wild-type has been replaced by another amino acid. Even more preferred are corresponding substitution mutants in which a change in the corresponding amino acid leads to a reduction in the enzyme activity compared with wt-NPT to 1 to 80%, preferably to 1 to 60%, more preferably to 1.5 to 30%, most preferably to 1.5% to 26%. Particularly preferred are modified NPT genes in which the amino acid 91, 227, 261 and/or 240 has been modified accordingly so that the enzyme activity compared with the wt-NPT is only 1 to 80%, preferably only 1 to 60%, more preferably only 1.5 to 30%, most preferably only 1.5% to 26%. Most preferred is a substitution mutant in which the amino acid at amino acid position 227 has been modified in the form such that the enzyme activity of the modified NPT is less than 26%, preferably between 1 and 20%, more preferably between 1 and 16% compared with the wt-NPT.

According to another embodiment of the present invention, advantageous mutants are those which, by comparison with wtNPT, code for glycine, alanine, valine, leucine, isoleucine, phenylalanine or tyrosine at amino acid positions 91, 182 or 227. Moreover, the glutamic acid at amino acid position 182 may also be replaced by aspartic acid, asparagine, glutamine or any other preferably negatively charged amino acid. Also preferred are modified NPT genes which, by comparison with wtNPT, code for glycine, alanine, leucine, isoleucine, phenylalanine, tyrosine or tryptophan at amino acid position 198. Also preferred are modified NPT genes which, by comparison with wtNPT, code for glycine, alanine, leucine, isoleucine, phenylalanine, tyrosine, tryptophan, asparagine, glutamine or aspartic acid at amino acid position 261. In particular, it has been found that with the mutants Glu182Gly, Glu182Asp, Trp91Ala, Val198Gly, Asp227Ala, Asp227Val, Asp227Gly, Asp261Gly, Asp261Asn and Phe240Ile as selectable markers it was possible to achieve an enrichment of transfected mammalian cells with high expression rates of the co-integrated gene of interest, with the result that these mutants are particularly preferred. Still more preferred are the mutants Asp227Val, Asp227Gly, Asp261Gly, Asp261Asn, Phe240Ile and Trp91Ala, as the best enrichment rates are achieved using them. The mutant Asp227Val is particularly preferred.

By contrast, the Asp190Gly and Asp208Gly mutants proved to be unsuitable markers for the selection of transfected CHO-DG44 cells under serum-free culture conditions. As a result of the presumably greatly reduced enzyme function of these mutants (Asp190Gly, Asp208Gly), only a few cells were obtained after the selection phase, which were moreover severely impaired in their growth and vitality.

The amino acids at positions 182 and 227 based on the wild-type are non-conserved amino acids which are located outside the three conserved motifs in the C-terminal region of the aminoglycoside-3'-phosphotransferases. The amino acid at position 91 also belongs to the non-conserved amino acids and is located outside one of the conserved motifs in the N-terminal region of the aminoglycoside-3'-phosphotransferases. By contrast the amino acids at positions 198 and 240 are conserved amino acids in the C-terminal region of the NPT, but are nevertheless outside the conserved motifs. By contrast, the amino acid at position 261 is a conserved amino acid in the third conserved motif of the C-terminal region (Shaw, K. J. et al., Microbiological Reviews 1993, 57(1), 138-163; Hon, W. et al., *Cell* 1997, 89, 887-895; Burk, D. L. et al., *Biochemistry* 2001, 40 (30), 8756-8764).

Compared with the use of wtNPT as selectable marker the cells in the case of the Glu182Gly, Glu182Asp and Val198Gly mutant showed a productivity increased by a factor of 1.4-2.4, in the case of the Asp227Gly mutant productivity was increased by a factor of 1.6-4.1, in the case of the Asp227Ala or Trp91Ala mutant productivity was increased by a factor of 2.2 or 4, in the case of the Phe240Ile or Asp261Asn mutant productivity was increased by a factor of 5.7 or 7.3 and in the case of the Asp261Gly or Asp227Val mutant it was even increased by a factor of 9.3 or 14.6. To express the multi-chained protein (an antibody), co-transfection was carried out. The two protein chains were each expressed by their own vector, one vector additionally coding for the NPT gene while the other vector coded for the amplifiable selectable dihydrofolate reductase gene.

The present invention thus relates to a process for enriching for recombinant mammalian cells which express a modified neomycin phosphotransferase gene, characterised in that (i) a pool of mammalian cells is transfected with a gene for a modified neomycin phosphotransferase which has only 1 to 80%, preferably 1 to 60%, more preferably 1.5 to 30%, most preferably 1.5 to 26% of the activity of wild-type neomycin phosphotransferase and/or one of the modifications described herein; (ii) the mammalian cells are cultivated under conditions which allow expression of the modified neomycin phosphotransferase gene; and (iii) the mammalian cells are cultivated in the presence of at least one selecting agent which acts selectively on the growth of mammalian cells, and gives preference to the growth of those cells which express the neomycin phosphotransferase gene.

Particularly preferred is a corresponding process which uses a modified NPT gene described in more detail in this application, particularly if the modified NPT gene used codes for a modified NPT which, by comparison with the wild-type gene, codes for alanine at amino acid position 91, for glycine or aspartic acid at amino acid position 182, for glycine at amino acid position 198, for alanine, glycine or valine at amino acid position 227, for glycine or asparagine at amino acid position 261 or for isoleucine at amino acid position 240. Still more preferred are NPT genes which, by comparison with the wild-type gene, code for valine at amino acid position 227 and/or for glycine and/or asparagine at amino acid position 261. Particularly preferred are those NPT genes which, by comparison with the wild-type gene, code at amino acid position 240 for an isoleucine or at amino acid position 227 for a valine, while an NPT gene which codes for valine at amino acid position 227 compared with the wild-type gene is particularly preferred. Naturally, the present invention also includes modified NPT genes and the use of modified NPT genes according to the invention which comprise a combination of the corresponding amino acid exchanges.

The present invention further relates to eukaryotic expression vectors which contain (i) a heterologous gene of interest functionally linked to a heterologous promoter and (ii) a modified neomycin phosphotransferase gene according to the invention which codes for a neomycin phosphotransferase which has low enzyme activity compared with wild-type neomycin phosphotransferase. By a "low" or "lower" enzyme activity for the purposes of the invention is meant an enzyme activity which corresponds to at most 80%, preferably 1 to 80%, more preferably only 1 to 60% of the enzyme activity of wtNPT. According to one embodiment of the present invention "lower enzyme activity" denotes an enzyme activity of 1 to 30%, preferably 1.5 to 26% compared with wild-type neomycin phosphotransferase.

A preferred expression vector contains a modified NPT gene which codes for a modified NPT which has only 1 to 80%, preferably only 1 to 60% of the enzyme activity of wtNPT. Also preferred are expression vectors with modified NPT genes which code for mutants having only 1 to 30% of the enzyme activity of wtNPT. Particularly preferred are those expression vectors which contain a modified NPT gene which code for mutants having only 1.5 to 26% of the enzyme activity of wtNPT, the activity being determined in the dot assay described in Example 4 and referred to as method 5.

In another embodiment of the invention the expression vectors contain genes of modified NPT which have been modified, compared with wtNPT, at amino acid position Trp91, Glu182, Val 98, Asp227, Phe240 or at position Asp261. In this context, NPT mutants are preferred which are modified at position Trp91, Glu182, Val198, Asp227, Phe240 or Asp261 and have only 1 to 80%, preferably only 1 to 60%, more preferably only 1.5 to 30%, and most preferably only 1.5 to 26% of the enzyme activity of wtNPT. Preferably the amino acids Tryp91, Glu182 or Asp227 may each be replaced by glycine, alanine, valine, leucine, isoleucine, phenylalanine or tyrosine at the corresponding position. Preferably the glutamic acid at position 182 may also be replaced by aspartic acid, asparagine, glutamine or another preferably negatively charged amino acid. Also preferred are modified NPT genes which code for glycine, alanine, leucine, isoleucine, phenylalanine, tyrosine or tryptophan at amino acid position 198 compared with wtNPT. In addition, modified NPT genes are preferred which code for glycine, alanine, valine, isoleucine, tyrosine or tryptophan at amino acid position 240 compared with wtNPT. Also preferred are modified NPT genes which code for glycine, alanine, leucine, isoleucine, phenylalanine, tyrosine, tryptophan, asparagine, glutamine or aspartic acid at amino acid 261 compared with wtNPT. It is particularly preferred to use a mutant wherein the aspartic acid at position 227 is replaced by glycine, alanine, valine, leucine or isoleucine, the aspartic acid at position 261 is replaced by an alanine, valine, leucine, isoleucine or glutamine, particularly by glycine or asparagine.

Particularly preferred are expression vectors which contain modified NPT genes which code for a Glu182Gly, Glu182Asp, Trp91 Ala, Val198Gly, Asp227Ala, Asp227Val, Asp227Gly, Asp261Gly, Asp261Asn or Phe240Ile mutant, which in the case of the Glu182Gly mutant contains the amino acid sequence of SEQ ID NO:4, in the case of the Glu182Asp mutant contains the amino acid sequence of SEQ ID NO:20, in the case of the Trp91Ala mutant contains the amino acid sequence of SEQ ID NO:6, in the case of the Val198Gly mutant contains the amino acid sequence of SEQ ID NO:8, in the case of the Asp227Ala mutant contains the amino acid sequence of SEQ ID NO:10, in the case of the Asp227Val mutant contains the amino acid sequence of SEQ ID NO:12, in the case of the Asp227Gly mutant contains the amino acid sequence of SEQ ID NO:22, in the case of the Asp261 Gly mutant contains the amino acid sequence of SEQ ID NO:14, in the case of the Asp261Asn mutant contains the amino acid sequence of SEQ ID NO:16 and in the case of the Phe240Ile mutant contains the amino acid sequence of SEQ ID NO:18. Most preferred is an expression vector using an Asp227Val, Asp227Gly, Asp261Gly, Asp261Asn, Phe240Ile or Trp91Ala mutant, particularly if it contains the amino acid sequence given in SEQ ID NO:12, SEQ ID NO:22, SEQ ID NO:14, SEQ ID NO:16, SEQ ID NO:18 or SEQ ID NO:6 or also if it is coded by the nucleic acid sequence given in SEQ ID NO:11, SEQ ID NO:21, SEQ ID NO:13, SEQ ID NO:15, SEQ ID NO:17 or SEQ ID NO:5 or contains it.

In addition the present invention provides for the first time modified neomycin phosphotransferase genes and the gene products thereof which compared with wtNPT code for a different amino acid than the wt amino acid at amino acid position Trp91, Val198 or Phe240. The present invention particularly provides for the first time Trp91, Val198 or Phe240 mutants which have a reduced enzyme activity compared with wtNPT. The modified NPTs described here and made available within the scope of the invention preferably code for alanine at amino acid position 91, for glycine at position 198 and for isoleucine at position 240. Furthermore, the present invention provides for the first time NPT mutants which, compared with wtNPT, code for glycine at position 182, for alanine or valine at position 227 and for glycine at position 261. Both the genes and the gene products (enzymes) are provided for the first time within the scope of the invention. In this context the present invention provides for the first time modified NPT with the amino acid sequences according to SEQ ID NO:4, SEQ ID NO:6, SEQ ID NO:8, SEQ ID NO:10, SEQ ID NO:12, SEQ ID NO:14 and SEQ ID NO:18. Moreover, the present invention provides modified NPT genes with the DNA sequences according to SEQ ID NO:3, SEQ ID NO:5, SEQ ID NO:7, SEQ ID NO:9, SEQ ID NO:11, SEQ ID NO:13, and SEQ ID NO:17.

Gene of Interest

The gene of interest contained in the expression vector according to the invention comprises a nucleotide sequence of any length which codes for a product of interest. The gene product or "product of interest" is generally a protein, polypeptide, peptide or fragment or derivative thereof. However, it may also be RNA or antisense RNA. The gene of interest may be present in its full length, in shortened form, as a fusion gene or as a labelled gene. It may be genomic DNA or preferably cDNA or corresponding fragments of fusions. The gene of interest may be the native gene sequence, or it may be mutated or otherwise modified. Such modifications include codon optimisations for adapting to a particular host cell and humanisation. The gene of interest may, for example, code for a secreted, cytoplasmic, nuclear-located, membrane-bound or cell surface-bound polypeptide.

The term "nucleotide sequence" or "nucleic acid sequence" indicates an oligonucleotide, nucleotides, polynucleotides and fragments thereof as well as DNA or RNA of genomic or synthetic origin which occur as single or double strands and can represent the coding or non-coding strand of a gene. Nucleic acid sequences may be modified using standard techniques such as site-specific mutagenesis or PCR-mediated mutagenesis (e.g. described in Sambrook, J. et al., Molecular Cloning: A Laboratory Manual Cold Spring Harbor Laboratory, Cold Spring Harbor, N.Y., 1989; Ausubel, F. M. et al., Current Protocols in molecular biology. New York: Greene Publishing Associates and Wiley-Interscience. 1994).

By "coding" is meant the property or capacity of a specific sequence of nucleotides in a nucleic acid, for example a gene in a chromosome or an mRNA, to act as a matrix for the synthesis of other polymers and macromolecules such as for example rRNA, tRNA, mRNA, other RNA molecules, cDNA or polypeptides in a biological process. Accordingly, a gene codes for a protein if the desired protein is produced in a cell or another biological system by transcription and subsequent translation of the mRNA. Both the coding strand whose nucleotide sequence is identical to the mRNA sequence and is normally also given in sequence databanks, e.g. EMBL or GenBank, and also the non-coding strand of a gene or cDNA which acts as the matrix for transcription may be referred to as coding for a product or protein. A nucleic acid which codes for a protein also includes nucleic acids which have a different order of nucleotide sequence on the basis of the degenerate genetic code but result in the same amino acid sequence of the protein. Nucleic acid sequences which code for proteins may also contain introns.

The term cDNA denotes deoxyribonucleic acids which are prepared by reverse transcription and synthesis of the second DNA strand from a mRNA or other RNA produced from a gene. If the cDNA is present as a double stranded DNA molecule it contains both a coding and a non-coding strand.

The term intron denotes non-coding nucleotide sequences of any length. They occur naturally in numerous eukaryotic genes and are eliminated from a previously transcribed mRNA precursor by a process known as splicing. This requires precise excision of the intron at the 5' and 3' ends and correct joining of the resulting mRNA ends so as to produce a mature processed mRNA with the correct reading frame for successful protein synthesis. Many of the splice donor and splice acceptor sites involved in this splicing process, i.e. the sequences located directly at the exon-intron or intron-exon interfaces, have been characterised by now. For an overview see Ohshima et al., 1987.

Protein/Product of Interest

Proteins/polypeptides with a biopharmaceutical significance include for example antibodies, enzymes, cytokines, lymphokines, adhesion molecules, receptors and the derivatives or fragments thereof, but are not restricted thereto. Generally, all polypeptides which act as agonists or antagonists and/or have therapeutic or diagnostic applications are of value.

The term "polypeptides" is used for amino acid sequences or proteins and refers to polymers of amino acids of any length. This term also includes proteins which have been modified post-translationally by reactions such as glycosylation, phosphorylation, acetylation or protein processing. The structure of the polypeptide may be modified, for example, by substitutions, deletions or insertions of amino acids and fusion with other proteins while retaining its biological activity. The term "polypeptides" thus also includes, for example, fusion proteins consisting of an immunoglobulin component, e.g. the Fc component, and a growth factor, e.g. an interleukin.

Examples of therapeutic proteins are insulin, insulin-like growth factor, human growth hormone (hGH) and other growth factors, tissue plasminogen activator (tPA), erythropoietin (EPO), cytokines, e.g. interleukins (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18 interferon (IFN)-alpha, -beta, -gamma, -omega or -tau, tumour necrosis factor (TNF) such as TNF-alpha, beta or gamma, TRAIL, G-CSF, GM-CSF, M-CSF, MCP-1 and VEGF. Other examples are monoclonal, polyclonal, multispecific and single chain antibodies and fragments thereof such as for example Fab, Fab', F(ab')$_2$, Fc and Fc' fragments, light (L) and heavy (H) immunoglobulin chains and the constant, variable or hypervariable regions thereof as well as Fv and Fd fragments (Chamov, S. M. et al., Antibody Fusion Proteins, Wiley-Liss Inc., 1999). The antibodies may be of human or non-human origin. Humanised and chimeric antibodies are also possible.

Fab fragments (fragment antigen binding=Fab) consist of the variable regions of both chains which are held together by the adjacent constant regions. They may be produced for example from conventional antibodies by treating with a protease such as papain or by DNA cloning. Other antibody fragments are F(ab')$_2$ fragments which can be produced by proteolytic digestion with pepsin.

By gene cloning it is also possible to prepare shortened antibody fragments which consist only of the variable regions of the heavy (VH) and light chain (VL). These are known as Fv fragments (fragment variable=fragment of the variable part). As covalent binding via the cystein groups of the constant chains is not possible in these Fv fragments, they are often stabilised by some other method. For this purpose the variable region of the heavy and light chains are often joined together by means of a short peptide fragment of about 10 to 30 amino acids, preferably 15 amino acids. This produces a single polypeptide chain in which VH and VL are joined together by a peptide linker. Such antibody fragments are also referred to as single chain Fv fragments (scFv). Examples of scFv antibodies are known and described, cf. for example Huston et al., 1988.

In past years various strategies have been developed for producing multimeric scFv derivatives. The intention is to produce recombinant antibodies with improved pharmacokinetic properties and increased binding avidity. In order to achieve the multimerisation of the scFv fragments they are produced as fusion proteins with multimerisation domains. The multimerisation domains may be, for example, the CH3 region of an IgG or helix structures ("coiled coil structures") such as the Leucine Zipper domains. In other strategies the interactions between the VH and VL regions of the scFv fragment are used for multimerisation (e.g. dia, tri- and pentabodies). The term diabody is used in the art to denote a bivalent homodimeric scFv derivative. Shortening the peptide linker in the scFv molecule to 5 to 10 amino acids results in the formation of homodimers by superimposing VH/VL chains. The diabodies may additionally be stabilised by inserted disulphide bridges. Examples of diabodies can be found in the literature, e.g. in Perisic et al., 1994.

The term minibody is used in the art to denote a bivalent homodimeric scFv derivative. It consists of a fusion protein which contains the CH3 region of an immunoglobulin, preferably IgG, most preferably IgG1, as dimerisation region. This connects the scFv fragments by means of a hinge region, also of IgG, and a linker region. Examples of such minibodies are described by Hu et al., 1996.

The term triabody is used in the art to denote a trivalent homotrimeric scFv derivative (Kortt, A. A. et al., *Protein Engineering* 1997, 10 (4), 423-433). The direct fusion of VH VL without the use of a linker sequence leads to the formation of trimers.

The fragments known in the art as mini antibodies which have a b-i, tri- or tetravalent structure are also derivatives of scFv fragments. The multimerisation is achieved by means of di, tri- or tetrameric coiled coil structures (Pack, P. et al., *Biotechnology* 1993, 11, 1271-1277; Pack, P. et al., *J. Mol. Biol.* 1995, 246(11):28-34; Lovejoy, B. et al., *Science* 1993, 259, 1288-1293).

Gene which Codes for a Fluorescent Protein

In another embodiment the expression vector according to the invention contains a gene coding for a fluorescent protein, preferably functionally linked to the gene of interest. Preferably, both genes are transcribed under the control of a single heterologous promoter so that the protein/product of interest and the fluorescent protein are coded by a bicistronic mRNA. This makes it possible to identify cells which produce the protein/product of interest in large amounts, by means of the expression rate of the fluorescent protein.

The fluorescent protein may be, for example, a green, bluish-green, blue, yellow or other coloured fluorescent protein. One particular example is green fluorescent protein (GFP) obtained from *Aequorea victoria* or *Renilla reniformis* and mutants developed from them; cf. for example Bennet et al., 1998; Chalfie et al., 1994; WO 01/04306 and the literature cited therein.

Other fluorescent proteins and genes coding for them are described in WO 00/34318, WO 00/34326, WO 00/34526 and WO 01/27150 which are incorporated herein by reference. These fluorescent proteins are fluorophores of non-bioluminescent organisms of the species *Anthozoa*, for example *Anemonia majano, Clavularia* sp., *Zoanthus* sp. I, *Zoanthus* sp. II, *Discosoma striata, Discosoma* sp. "red", *Discosoma* sp. "green", *Discosoma* sp. "Magenta", *Anemonia sulcata*.

The fluorescent proteins used according to the invention contain in addition to the wild-type proteins natural or genetically engineered mutants and variants, fragments, derivatives or variants thereof which have for example been fused with other proteins or peptides. The mutations used may for example alter the excitation or emission spectrum, the formation of chromophores, the extinction coefficient or the stability of the protein. Moreover, the expression in mammalian cells or other species can be improved by codon optimisation. According to the invention the fluorescent protein may also be used in fusion with a selectable marker, preferably an amplifiable selectable marker such as dihydrofolate reductase (DHFR).

The fluorescence emitted by the fluorescent proteins makes it possible to detect the proteins, e.g. by throughflow cytometry with a fluorescence-activated cell sorter (FACS) or by fluorescence microscopy.

Other Regulatory Elements

The expression vector contains at least one heterologous promoter which allows expression of the gene of interest and preferably also of the fluorescent protein.

The term promoter denotes a polynucleotide sequence which allows and controls the transcription of the genes or sequences functionally connected therewith. A promoter contains recognition sequences for binding RNA polymerase and the initiation site for transcription (transcription initiation site). In order to express a desired sequence in a certain cell type or a host cell a suitable functional promoter must be chosen. The skilled artisan will be familiar with a variety of promoters from various sources, including constitutive, inducible and repressible promoters. They are deposited in databanks such as GenBank, for example, and may be obtained as separate elements or elements cloned within polynucleotide sequences from commercial or individual sources. In inducible promoters the activity of the promoter may be reduced or increased in response to a signal. One example of an inducible promoter is the tetracycline (tet) promoter. This contains tetracycline operator sequences (tetO) which can be induced by a tetracycline-regulated transactivator protein (tTA). In the presence of tetracycline the binding of tTA to tetO is inhibited. Examples of other inducible promoters are the jun, fos, metallothionein and heat shock promoter (see also Sambrook, J. et al., Molecular Cloning: A Laboratory Manual Cold Spring Harbor Laboratory, Cold Spring Harbor, N.Y., 1989; Gossen, M. et al., *Curr Opinion Biotech* 1994, 5, 516-520).

Of the promoters which are particularly suitable for high expression in eukaryotes, there are for example the ubiquitin/S27a promoter of the hamster (WO 97/15664), SV 40 early promoter, adenovirus major late promoter, mouse metallothionein-I promoter, the long terminal repeat region of Rous Sarcoma Virus, the early promoter of human Cytomegalovirus. Examples of other heterologous mammalian promoters are the actin, immunoglobulin or heat shock promoter(s).

A corresponding heterologous promoter can be functionally connected to other regulatory sequences in order to increase/regulate the transcription activity in an expression cassette.

For example, the promoter may be functionally linked to enhancer sequences in order to increase the transcriptional activity. For this, one or more enhancers and/or several copies of an enhancer sequence may be used, e.g. a CMV or SV40 enhancer. Accordingly, an expression vector according to the invention, in another embodiment, contains one or more enhancers/enhancer sequences, preferably a CMV or SV40 enhancer. The term enhancer denotes a polynucleotide sequence which in the cis location acts on the activity of a promoter and thus stimulates the transcription of a gene functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

Another possible modification is, for example, the introduction of multiple Sp1 binding sites. The promoter sequences may also be combined with regulatory sequences which allow control/regulation of the transcription activity. Thus, the promoter can be made repressible/inducible. This can be done for example by linking to sequences which are binding sites for up- or down-regulating transcription factors. The above-mentioned transcription factor Sp1, for example, has a positive effect on the transcription activity. Another example is the binding site for the activator protein AP1, which may act both positively and negatively on transcription. The activity of AP1 can be controlled by all kinds of factors such as, for example, growth factors, cytokines and serum (Faisst, S. et al., *Nucleic Acids Research* 1992, 20, 3-26 and references therein). The transcription efficiency can also be increased by changing the promoter sequence by the mutation (substitution, insertion or deletion) of one, two, three or more bases and then determining, in a reporter gene assay, whether this has increased the promoter activity.

Basically, the additional regulatory elements include heterologous promoters, enhancers, termination and polyadenylation signals and other expression control elements. Both inducible and constitutively regulatory sequences are known for the various cell types.

"Transcription-regulatory elements" generally comprise a promoter upstream of the gene sequence to be expressed, transcription initiation and termination sites and a polyadenylation signal.

The term "transcription initiation site" refers to a nucleic acid in the construct which corresponds to the first nucleic acid which is incorporated in the primary transcript, i.e. the mRNA precursor. The transcription initiation site may overlap with the promoter sequences.

The term "transcription termination site" refers to a nucleotide sequence which is normally at the 3' end of the gene of interest or of the gene section which is to be transcribed, and which brings about the termination of transcription by RNA polymerase.

The "polyadenylation signal" is a signal sequence which causes cleavage at a specific site at the 3' end of the eukaryotic mRNA and post-transcriptional incorporation of a sequence of about 100-200 adenine nucleotides (polyA tail) at the cleaved 3' end. The polyadenylation signal comprises the sequence AATAAA about 10-30 nucleotides upstream of the cleavage site and a sequence located downstream. Various polyadenylation elements are known such as tk polyA, SV40 late and early polyA or BGH polyA (described for example in U.S. Pat. No. 5,122,458).

In a preferred embodiment of the present invention each transcription unit has a promoter or a promoter/enhancer element, a gene of interest and/or a marker gene as well as a transcription termination element. In another preferred embodiment the transcription unit contains two further translation regulatory units.

"Translation regulatory elements" comprise a translation initiation site (AUG), a stop codon and a polyA signal for each polypeptide to be expressed. For optimum expression it may be advisable to remove, add or change 5'- and/or 3'-untranslated regions of the nucleic acid sequence which is to be expressed, in order to eliminate any potentially unsuitable additional translation initiation codons or other sequences which might affect expression at the transcription or expression level. In order to promote expression, ribosomal consensus binding sites may alternatively be inserted immediately upstream of the start codon. In order to produce a secreted polypeptide the gene of interest usually contains a signal sequence which codes for a signal precursor peptide which transports the synthesised polypeptide to and through the ER membrane. The signal sequence is often but not always located at the amino terminus of the secreted protein and is cleaved by signal peptidases after the protein has been filtered through the ER membrane. The gene sequence will usually but not necessarily contain its own signal sequence. If the native signal sequence is not present a heterologous signal sequence may be introduced in known manner. Numerous signal sequences of this kind are known to the skilled artisan and deposited in sequence databanks such as GenBank and EMBL.

One important regulatory element according to the invention is the internal ribosomal entry site (IRES). The IRES element comprises a sequence which functionally activates the translation initiation independently of a 5'-terminal methylguanosinium cap (CAP structure) and the upstream gene and in an animal cell allows the translation of two cistrons (open reading frames) from a single transcript. The IRES element provides an independent ribosomal entry site for the translation of the open reading frame located immediately downstream. In contrast to bacterial mRNA which may be multicistronic, i.e. it may code for numerous different polypeptides or products which are translated one after the other by the mRNA, the majority of mRNAs from animal cells are monocistronic and code for only one protein or product. In the case of a multicistronic transcript in a eukaryotic cell the translation would be initiated from the translation initiation site which was closest upstream and would be stopped by the first stop codon, after which the transcript would be released from the ribosome. Thus, only the first polypeptide or product coded by the mRNA would be produced during translation. By contrast, a multicistronic transcript with an IRES element which is functionally linked to the second or subsequent open reading frame in the transcript allows subsequent translation of the open reading frame located downstream thereof, so that two or more polypeptides or products coded by the same transcript are produced in the eukaryotic cell.

The IRES element may be of various lengths and various origins and may originate, for example, from the encephalomyocarditis virus (EMCV) or other Picorna viruses. Various IRES sequences and their use in the construction of vectors are described in the literature, cf. for example Pelletier et al., 1988; Jang et al., 1989; Davies et al., 1992; Adam et al., 1991; Morgan et al., 1992; Sugimoto et al., 1994; Ramesh et al., 1996; Mosser et al., 1997.

The gene sequence located downstream is functionally linked to the 3' end of the IRES element, i.e. the spacing is selected so that the expression of the gene is unaffected or only marginally affected or has sufficient expression for the intended purpose. The optimum permissible distance between the IRES element and the start codon of the gene located downstream thereof for sufficient expression can be determined by simple experiments by varying the spacing and determining the expression rate as a function of the spacing using reporter gene assays.

By the measures described it is possible to obtain an optimum expression cassette which is of great value for the expression of heterologous gene products. An expression cassette obtained by means of one or more such measures is therefore a further subject of the invention.

Hamster-Ubiquitin/S27a Promoter

In another embodiment the expression vector according to the invention contains the ubiquitin/S27a promoter of the hamster, preferably functionally linked to the gene of interest and even more preferably functionally linked to the gene of interest and the gene which codes for a fluorescent protein.

The ubiquitin/S27a promoter of the hamster is a powerful homologous promoter which is described in WO 97/15664. Such a promoter preferably has at least one of the following features: GC-rich sequence area, Sp1 binding site, polypyrimidine element, absence of a TATA box. Particularly preferred is a promoter which has an Sp1 binding site but no TATA box. Also preferred is a promoter which is constitutively activated and in particular is equally active under serum-containing, low-serum and serum-free cell culture conditions. In another embodiment it is an inducible promoter, particularly a promoter which is activated by the removal of serum.

Figure 5:
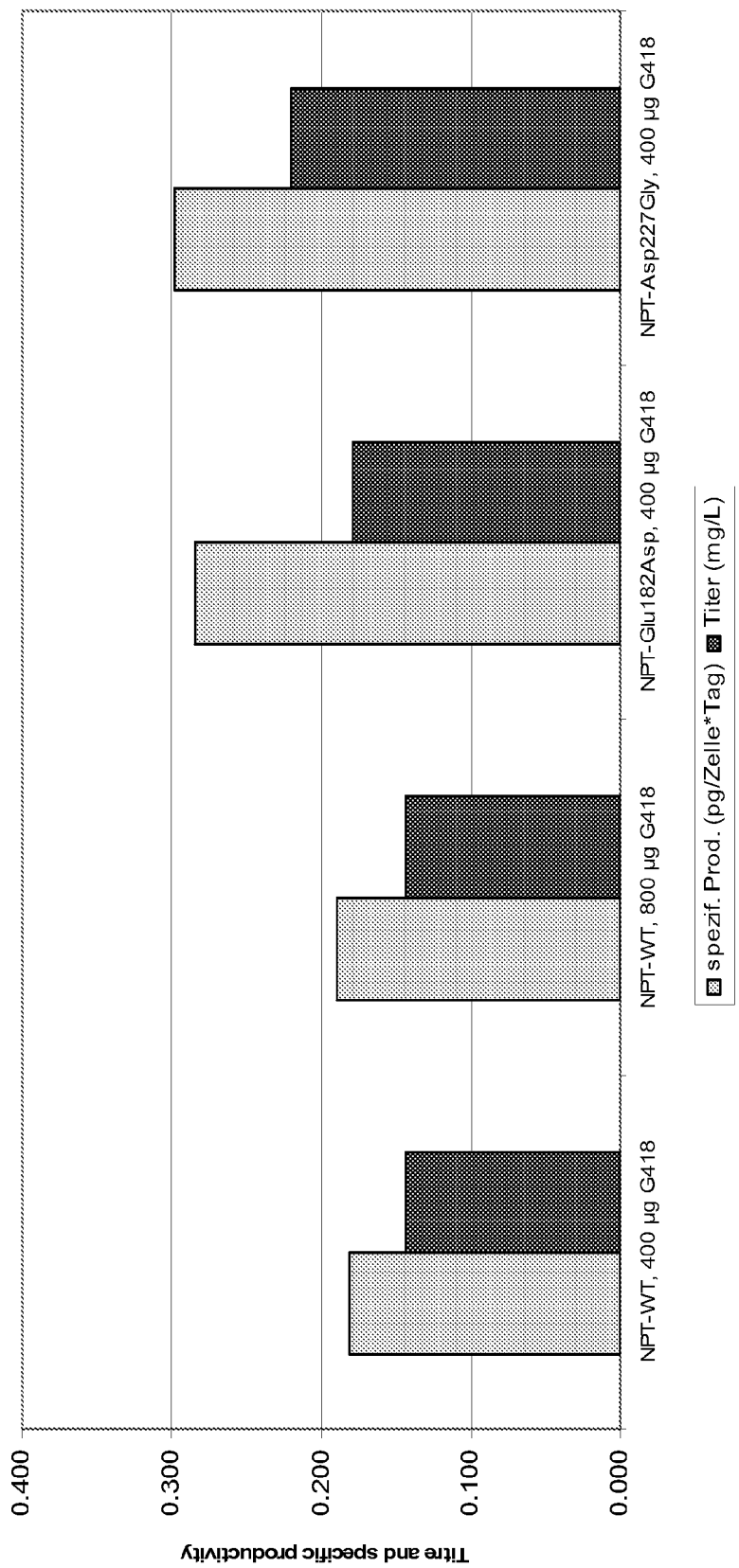
FIG. 5 shows the influence of the NPT mutations on the selection of stably transfected MCP-1-expressing cells. For this, CHO-DG44 cells were transfected with the vectors pBIN-MCP1, pKS-N-5-MCP1 and pKS-N-8-MCP1 (FIG. 2A), which contained as selectable marker either the NPT wild-type (WT) or the NPT mutants Glu182Asp and Asp227Gly. For selecting stably transfected cells, 400 μg/mL or 800 μg/mL of G418 was added to the medium as a selective agent. The concentration in the cell culture supernatant of the recombinant protein MCP-1 produced was determined by ELISA and the specific productivity per cell and per day was calculated. The bars represent the averages of the specific productivity or of the titre of 18 pools from 6 cultivation in 6-well dishes.

A particularly advantageous embodiment is a promoter with a nucleotide sequence as contained in FIG. 5 of WO 97/15664. Particularly preferred are promoter sequences which contain the sequence from position −161 to −45 of FIG. 5.

The promoters used in the examples of the present patent specification each contain a DNA molecule with the sequence from position 1923 to 2406 of SEQ ID NO:55 of the attached sequence listing. This sequence corresponds to the fragment −372 to +111 from FIG. 5 of WO 97/15664 and represents the preferred promoter, i.e a preferred promoter should incorporate this sequence region. Another suitable promoter fragment contains the sequence from position 2134 to 2406 (corresponding to −161 to +111 in FIG. 5 of WO 97/15664). A promoter which contains only the sequence from position 2251 to 2406 is no longer functional (corresponds to position −45 to +111 in FIG. 5 of WO 9/15664). It is possible to extend the promoter sequence in the 5' direction starting from position 2134.

It is also possible to use functional subfragments of the complete hamster ubiquitin/S27a promoter sequence as well as functional mutants/variants of the complete sequence of subfragments thereof which have been modified, for example, by substitution, insertion or deletion. Corresponding subfragments, mutants or variants are hereinafter also referred to as "modified promoters".

A modified promoter, optionally combined with other regulatory elements, preferably has a transcription activity which corresponds to that of the promoter fragment from position 1923 to 2406 of the nucleotide sequence given in SEQ ID NO:55 (−372 to +111 from FIG. 5 of WO 97/15664). A modified promoter proves to be useful for the purposes of the invention if it has a transcription activity which has at least 50%, preferably at least 80%, more preferably at least 90% and most preferably at least 100% of the activity of the 1923 to 2406 fragment (−372 to +111 fragment) in a comparative reporter gene assay. Particularly preferred are modified promoters which have a minimum sequence homology to the wild-type sequence SEQ ID NO:55 of the hamster ubiquitin/S27a promoter of at least 80%, preferably at least 85%, preferably at least 90%, more preferably at least 95% and most preferably at least 97% and have a corresponding promoter activity in a comparative reporter gene assay.

In a corresponding comparative reporter gene assay the promoter fragments to be tested including the reference sequence are cloned in front of a promoterless reporter gene which codes, for example for luciferase, secreted alkaline phosphotase or green fluorescent protein (GFP). These constructs (promoter sequence+reporter gene) are subsequently introduced into the test cells, e.g. CHO-DG44, by transfection and the induction of the reporter gene expression by the promoter fragment in question is determined by measuring the protein content of the reporter gene. A corresponding test is found for example in Ausubel et al., Current Protocols in Molecular Biology, 1994.

The promoter sequence of the hamster ubiquitin/S27a promoter and the modified promoters, which may also include, for example, the 5' untranslated region or selected fragments thereof, and the coding region as well as the 3'-untranslated region of the ubiquitin/S27a gene or selected fragments thereof, may be obtained by a skilled artisan with a knowledge of the sequence described in WO 97/15664 using various standard methods as described for example in Sambrook et al.; Ausubel et al. (Sambrook, J. et al., Molecular Cloning: A Laboratory Manual Cold Spring Harbor Laboratory, Cold Spring Harbor, N.Y., 1989; Ausubel, F. M. et al., Current Protocols in Molecular Biology. New York: Greene Publishing Assoc. and Wiley-Interscience. 1994). Starting from the sequence described in WO 97/15664 a suitable fragment may be selected, for example, and an oligonucleotide probe containing the sequence of this fraction may be chemically synthesised. A probe of this kind may be used for example to clone the ubiquitin/S27a gene or the 5' untranslated region or other fragments thereof, for example by hybridisation from a library of the hamster genome. Using the reporter gene assay described above the skilled artisan is in a position to identify promoter-active fragments without any great effort and use them for the purposes of the present invention. The 5' untranslated region or special fragments thereof can easily be obtained by PCR amplification with corresponding primers from genomic DNA or a genomic library. Fragments of the 5' untranslated region may also be obtained by limited exonuclease III digestion from larger DNA fragments. Such DNA molecules may also be chemically synthesised or produced from chemically synthesised fragments by ligation.

Deletion, insertion and substitution mutants may be produced by "site-specific mutagenesis" and/or "PCR-based mutagenesis techniques". Corresponding methods are mentioned for example in Lottspeich and Zorbas (Lottspeich and Zorbas eds. Bioanalytic, Spektrum Akad. Verl., 1998, Chapter 36.1 with other references).

By cross-hybridisation with probes from the 5' untranslated region of the hamster ubiquitin/S27a gene or from the S27a part of the hamster ubiquitin S27a gene or the 3'-untranslated region it is also possible to identify and isolate suitable promoter sequences from corresponding homologous genes of other, preferably mammalian species. Suitable techniques are described by way of example in Lottspeich and Zorbas (Lottspeich and Zorbas eds. Bioanalytic, Spektrum Akad. Verl., 1998, Chapter 23). Genes are "homologous" for the purposes of the invention if their nucleotide sequence exhibits at least 70%, preferably at least 80%, preferably at least 90%, more preferably at least 95% and most preferably at least 97% conformity to the nucleotide sequence of the gene with which it is homologous.

Using the measures described above it is possible to obtain an optimised expression cassette which is highly valuable for the expression of heterologous gene products. An expression cassette obtained by one or more such measures is therefore a further object of the invention.

Preparation of Expression Vectors According to the Invention

The expression vector according to the invention may theoretically be prepared by conventional methods known in the art, as described by Sambrook et al., for example (Sambrook, J. et al., Molecular Cloning: A Laboratory Manual Cold Spring Harbor Laboratory, Cold Spring Harbor, N.Y., 1989). Sambrook also describes the functional components of a vector, e.g. suitable promoters (in addition to the hamster ubiquitin/S27a promoter), enhancers, termination and polyadenylation signals, antibiotic resistance genes, selectable markers, replication starting points and splicing signals. Conventional cloning vectors may be used to produce them, e.g. plasmids, bacteriophages, phagemids, cosmids or viral vectors such as baculovirus, retroviruses, adenoviruses, adeno-associated viruses and herpes simplex virus, as well as artificial chromosomes/mini chromosomes. The eukaryotic expression vectors typically also contain prokaryotic sequences such as, for example, replication origin and antibiotic resistance genes which allow replication and selection of the vector in bacteria.

A number of eukaryotic expression vectors which contain multiple cloning sites for the introduction of a polynucleotide sequence are known and some may be obtained commercially from various companies such as Stratagene, La Jolla, Calif., USA; Invitrogen, Carlsbad, Calif., USA; Promega, Madison, Wis., USA or BD Biosciences Clontech, Palo Alto, Calif., USA.

The heterologous promoter, the gene of interest and the modified neomycin phosphotransferase gene and optionally the gene coding for a fluorescent protein, additional regulatory elements such as the internal ribosomal entry site (IRES), enhancers or a polyadenylation signal are introduced into the expression vector in a manner familiar to those skilled in the art. An expression vector according to the invention contains, at the minimum, a heterologous promoter, the gene of interest and a modified neomycin phosphotransferase gene. Preferably, the expression vector also contains a gene coding for a fluorescent protein. It is particularly preferred according to the invention to use a ubiquitin/S27a promoter as heterologous promoter. Particularly preferred is an expression vector in which the heterologous promoter, preferably a ubiquitin/S27a promoter, the gene of interest and the gene which codes for a fluorescent protein are functionally linked together or are functionally linked and the neomycin phosphotransferase gene is located in the same or in a separate transcription unit.

Within the scope of the present description the term "functional linking" or "functionally linked" refers to two or more nucleic acid sequences or partial sequences which are positioned so that they can perform their intended function. For example, a promoter/enhancer is functionally linked to a coding gene sequence if it is able to control or modulate the transcription of the linked gene sequence in the cis position. Generally, but not necessarily, functionally linked DNA sequences are close together and, if two coding gene sequences are linked or in the case of a secretion signal sequence, in the same reading frame. Although a functionally linked promoter is generally located upstream of the coding gene sequence it does not necessarily have to be close to it. Enhancers need not be close by either, provided that they assist the transcription of the gene sequence. For this purpose enhancers may be both upstream and downstream of the gene sequence, possibly at some distance from it. A polyadenylation site is functionally linked to a gene sequence if it is positioned at the 3' end of the gene sequence in such a way that the transcription progresses via the coding sequence to the polyadenylation signal. Linking may take place according to conventional recombinant methods, e.g. by the PCR technique, by ligation at suitable restriction cutting sites or by splicing. If no suitable restriction cutting sites are available synthetic oligonucleotide linkers or adaptors may be used in a manner known per se. According to the invention the functional linking preferably does not take place via intron sequences.

In one of the embodiments described, the heterologous promoter, preferably a ubiquitin/S27a promoter, the gene of interest and the gene coding for a fluorescent protein are functionally linked together. This means for example that both the gene of interest and the gene coding for a fluorescent protein are expressed starting from the same heterologous promoter.

In a particularly preferred embodiment the functional linking takes place via an IRES element, so that a bicistronic mRNA is synthesised from both genes. The expression vector according to the invention may additionally contain enhancer elements which act functionally on one or more promoters. Particularly preferred is an expression vector in which the heterologous promoter, preferably the ubiquitin/S27a promoter or a modified form thereof, is linked to an enhancer element, e.g. an SV40 enhancer or a CMV enhancer element.

Fundamentally, the expression of the genes within an expression vector may take place starting from one or more transcription units. The term transcription unit is defined as a region which contains one or more genes to be transcribed. The genes within a transcription unit are functionally linked to one another in such a way that all the genes within such a unit are under the transcriptional control of the same promoter or promoter/enhancer. As a result of this transcriptional linking of genes, more than one protein or product can be transcribed from a transcription unit and thus expressed. Each transcription unit contains the regulatory elements which are necessary for the transcription and translation of the gene sequences contained therein. Each transcription unit may contain the same or different regulatory elements. IRES elements or introns may be used for the functional linking of the genes within a transcription unit.

The expression vector may contain a single transcription unit for expressing the gene of interest, the modified NPT gene and optionally the gene which codes for the fluorescent protein. Alternatively, these genes may also be arranged in two or more transcription units. Various combinations of the genes within a transcription unit are possible. In another embodiment of the present invention more than one expression vector consisting of one, two or more transcription units may be inserted in a host cell by cotransfection or in successive transfections in any desired order. Any combination of regulatory elements and genes on each vector can be selected provided that adequate expression of the transcription units is ensured. If necessary, other regulatory elements and genes, e.g. additional genes of interest or selectable markers, may be positioned on the expression vectors.

Accordingly, an expression vector according to the invention containing a gene of interest and a gene which codes for a modified neomycin phosphotransferase may contain both genes in one or in two separate transcription units. Each transcription unit can transcribe and express one or more gene products. If both genes are contained in one transcription unit they are under the control of the same promoter or promoter/enhancer, while preferably an IRES element is used to ensure the functional linking of all the components. If the gene which codes for modified neomycin phosphotransferase and the gene of interest are contained in two separate transcription units, they may be under the control of the same or different promoters/enhancers. However, preferably, a weaker heterologous promoter, e.g. SV40 early promoter, is used for the modified NPT gene and preferably no enhancer is used. Expression vectors with two separate transcription units are preferred within the scope of the invention. One (bicistronic) transcription unit contains the gene of interest and optionally a gene coding for a fluorescent protein, while the other transcription unit contains the modified NPT gene. Preferably, each transcription unit is limited at the 3' end by a sequence which codes for a polyA signal, preferably BGH polyA or SV40 polyA.

Also preferred according to the invention are those expression vectors which instead of the gene of interest have only a multiple cloning site which allows the cloning of the gene of interest via recognition sequences for restriction endonucleases. Numerous recognition sequences for all kinds of restriction endonucleases as well as the associated restriction endonucleases are known from the prior art. Preferably, sequences are used which consist of at least six nucleotides as recognition sequence. A list of suitable recognition sequences can be found for example in Sambrook et al. (Sambrook, J. et al., Molecular Cloning: A Laboratory Manual Cold Spring Harbor Laboratory, Cold Spring Harbor, N.Y., 1989).

Host Cells

For transfection with the expression vector according to the invention eukaryotic host cells are used, preferably mammalian cells and more particularly rodent cells such as mouse, rat and hamster cell lines. The successful transfection of the corresponding cells with an expression vector according to the invention results in transformed, genetically modified, recombinant or transgenic cells, which are also the subject of the present invention.

Preferred host cells for the purposes of the invention are hamster cells such as BHK21, BHK TK⁻ CHO, CHO-K1, CHO-DUKX, CHO-DUKX B1 and CHO-DG44 cells or derivatives/descendants of these cell lines. Particularly preferred are CHO-DG44, CHO-DUKX, CHO-K1 and BHK21 cells, particularly CHO-DG44 and CHO-DUKX cells. Also suitable are myeloma cells from the mouse, preferably NS0 and Sp2/0 cells and derivatives/descendants of these cell lines.

Examples of hamster and mouse cells which can be used according to the invention are given in Table 1 that follows. However, derivatives and descendants of these cells, other mammalian cells including but not restricted to cell lines of humans, mice, rats, monkeys, rodents, or eukaryotic cells, including but not restricted to yeast, insect and plant cells, may also be used as host cells for the production of biopharmaceutical proteins.

TABLE 1

Hamster and Mouse Production Cell Lines

| Cell line | Accession Number |
|---|---|
| NS0 | ECASS No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 | ATCC CRL-8544 |
| (BHK-21-derivative) | |
| CHO | ECACC No. 8505302 |
| CHO-K1 | ATCC CCL-61 |
| CHO-DUKX | ATCC CRL-9096 |
| (=CHO duk⁻ CHO/dhfr⁻) | |
| CHO-DUKX B1 | ATCC CRL-9010 |
| CHO-DG44 | Urlaub et al; Cell 32[2], 405-412, 1983 |
| CHO Pro-5 | ATCC CRL-1781 |
| V79 | ATCC CCC-93 |
| B14AF28-G3 | ATCC CCL-14 |
| CHL | ECACC No. 87111906 |

The transfection of the eukaryotic host cells with a polynucleotide or one of the expression vectors according to the invention is carried out by conventional methods (Sambrook, J. et al., Molecular Cloning: A Laboratory Manual Cold Spring Harbor Laboratory, Cold Spring Harbor, N.Y., 1989; Ausubel, F. M. et al., Current Protocols in molecular biology. New York: Greene Publishing Associates and Wiley-Interscience. 1994. Suitable methods of transfection include for example liposome-mediated transfection, calcium phosphate co-precipitation, electroporation, polycation- (e.g. DEAE dextran)-mediated transfection, protoplast fusion, microinjection and viral infections. According to the invention stable transfection is preferably carried out in which the constructs are either integrated into the genome of the host cell or an artificial chromosome/minichromosome, or are episomally contained in stable manner in the host cell. The transfection method which gives the optimum transfection frequency and expression of the heterologous gene in the host cell in question is preferred. By definition, every sequence or every gene inserted in a host cell is referred to as a "heterologous sequence" or "heterologous gene" in relation to the host cell. This applies even if the sequence to be introduced or the gene to be introduced is identical to an endogenous sequence or an endogenous gene of the host cell. For example, a hamster actin gene introduced into a hamster host cell is by definition a heterologous gene.

According to the invention, recombinant mammalian cells, preferably rodent cells, most preferably hamster cells such as CHO or BHK cells which have been transfected with one of the expression vectors according to the invention described herein are preferred.

In the recombinant production of heteromeric proteins such as e.g. monoclonal antibodies (mAb), the transfection of suitable host cells can theoretically be carried out by two different methods. Monoclonal antibodies of this kind are composed of a number of subunits, the heavy and light chains. Genes coding for these subunits may be accommodated in independent or multicistronic transcription units on a single plasmid with which the host cell is then transfected. This is intended to secure the stoichiometric representation of the genes after integration into the genome of the host cell. However, in the case of independent transcriptional units it must hereby be ensured that the mRNAs which encode the different proteins display the same stability and transcriptional and translational efficiency. In the second case, the expression of the genes take place within a multicistronic transcription unit by means of a single promoter and only one transcript is formed. By using IRES elements, a highly efficient internal translation initiation of the genes is obtained in the second and subsequent cistrons. However, the expression rates for these cistrons are lower than that of the first cistron, the translation initiation of which, by means of a so-called "cap"-dependent pre-initiation complex, is substantially more efficient than IRES-dependent translation initiation. In order to achieve a truly equimolar expression of the cistrons, additional intercistronic elements may be introduced, for example, which ensure uniform expression rates in conjunction with the IRES elements (WO 94/05785).

Another possible way of simultaneously producing a number of heterologous proteins, which is preferred according to the invention, is cotransfection, in which the genes are separately integrated in different expression vectors. This has the advantage that certain proportions of genes and gene products with one another can be adjusted, thereby balancing out any differences in the mRNA stability and in the efficiency of transcription and translation. In addition, the expression vectors are more stable because of their small size and are easier to handle both during cloning and during transfection.

In one particular embodiment of the invention, therefore, the host cells are additionally transfected, preferably co-transfected, with one or more vectors having genes which code for one or more other proteins of interest. The other vector or vectors used for the cotransfection code, for example, for the other protein or proteins of interest under the control of the same promoter/enhancer combination and for at least one other selectable marker, e.g. dihydrofolate reductase.

According to the invention the host cells are preferably established, adapted and cultivated under serum-free conditions, optionally in media which are free from animal proteins/peptides. Examples of commercially obtainable media include Ham's F12 (Sigma, Deisenhofen, DE), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif., USA), CHO-S-SFMII (Invitrogen), serum-free CHO-Medium (Sigma) and protein-free CHO-Medium (Sigma). Each of these media may optionally be supplemented with various compounds, e.g. hormones and/or other growth factors (e.g. insulin, transferrin, epidermal growth factor, insulin-like growth factor), salts (e.g. sodium chloride, calcium, magnesium, phosphate), buffers (e.g. HEPES), nucleosides (e.g. adenosine, thymidine), glutamine, glucose or other equivalent nutrients, antibiotics and/or trace elements. Although serum-free media are preferred according to the invention, the host cells may also be cultivated and protein subsequently produced using media which have been mixed with a suitable amount of serum. In order to select genetically modified cells which express one or more selectable marker genes, one or more selecting agents are added to the medium.

The term "selecting agent" refers to a substance which affects the growth or survival of host cells with a deficiency for the selectable marker gene in question. Within the scope of the present invention, geneticin (G418) is preferably used as the medium additive for the selection of heterologous host cells which carry a modified neomycin phosphotransferase gene. Preferably, G418 concentrations of between 100 µg/ml and 800 µg/ml of medium are used, most preferably 300 µg/ml to 400 µg/ml of medium. If the host cells are to be transfected with a number of expression vectors, e.g. if several genes of interest are to be separately introduced into the host cell, they generally have different selectable marker genes.

A selectable marker gene is a gene which allows the specific selection of cells which contain this gene by the addition of a corresponding selecting agent to the cultivation medium. As an illustration, an antibiotic resistance gene may be used as a positive selectable marker. Only cells which have been transformed with this gene are able to grow in the presence of the corresponding antibiotic and are thus selected. Untransformed cells, on the other hand, are unable to grow or survive under these selection conditions. There are positive, negative and bifunctional selectable markers. Positive selectable markers permit the selection and hence enrichment of transformed cells by conferring resistance to the selecting agent or by compensating for a metabolic or catabolic defect in the host cell. By contrast, cells which have received the gene for the selectable marker can be selectively eliminated by negative selectable markers. An example of this is the thymidine kinase gene of the Herpes Simplex virus, the expression of which in cells with the simultaneous addition of acyclovir or gancyclovir leads to the elimination thereof. The selectable markers used in this invention, including the amplifiable selectable markers, include genetically modified mutants and variants, fragments, functional equivalence, derivatives, homologues and fusions with other proteins or peptides, provided that the selectable marker retains its selective qualities. Such derivatives display considerable homology in the amino acid sequence in the regions or domains which are deemed to be selective. The literature describes a large number of selectable marker genes including bifunctional (positive/negative) markers (see for example WO 92/08796 and WO 94/28143). Examples of selectable markers which are usually used in eukaryotic cells include the genes for aminoglycoside phosphotransferase (APH), hygromycine phosphotransferase (HYG), dihydrofolate reductase (DHFR), thymidine kinase (TK), glutamine synthetase, asparagine synthetase and genes which confer resistance to neomycin (G418), puromycin, histidinol D, belomycin, phleomycin and zeocin. It is also possible to select transformed cells by fluorescence-activated cell sorting (FACS). For this, bacterial β-galactosidase, cell surface markers or fluorescent proteins may be used (e.g. green fluorescent protein (GFP) and the variants thereof from Aequorea Victoria and *Renilla reniformis* or other species; red fluorescent proteins and proteins which fluoresce in other colours and their variants from non-bioluminescent organisms such as e.g. *Discosoma* sp., *Anemonia* sp., *Clavularia* sp., *Zoanthus* sp.) for the selection of transformed cells.

Gene Expression and Selection of High-Producing Host Cells

The term gene expression relates to the transcription and/or translation of a heterologous gene sequence in a host cell. The expression rate can be generally determined, either on the basis of the quantity of corresponding mRNA which is present in the host cell or on the basis of the quantity of gene product produced which is encoded by the gene of interest. The quantity of mRNA produced by transcription of a selected nucleotide sequence can be determined for example by northern blot hybridisation, ribonuclease-RNA-protection, in situ hybridisation of cellular RNA or by PCR methods (Sambrook, J. et al., Molecular Cloning: A Laboratory Manual Cold Spring Harbor Laboratory, Cold Spring Harbor, N.Y., 1989; Ausubel, F. M. et al., Current Protocols in molecular biology. New York: Greene Publishing Associates and Wiley-Interscience. 1994. Proteins which are encoded by a selected nucleotide sequence can also be determined by various methods such as, for example, ELISA, western blot, radioimmunoassay, immunoprecipitation, detection of the biological activity of the protein or by immune staining of the protein followed by FACS analysis (Sambrook, J. et al., Molecular Cloning: A Laboratory Manual Cold Spring Harbor Laboratory, Cold Spring Harbor, N.Y., 1989; Ausubel, F. M. et al., Current Protocols in molecular biology. New York: Greene Publishing Associates and Wiley-Interscience. 1994.

The terms "high expression level (or rate), high expression, increased expression or high productivity" refer to the long-lasting and sufficiently high expression or synthesis of a heterologous sequence introduced into a host cell, e.g. of a gene coding for a therapeutic protein. Increased or high expression or a high expression level or rate or a high productivity are present if a cell according to the invention is cultivated by one of the methods according to the invention described here, without gene amplification, and if this cell produces at least more than roughly 0.5 pg of the desired gene product per day (0.5 pg/cell/day). Increased or high expression or a high expression or rate or a high productivity are also present if the cell according to the invention without prior gene amplification produces at least more than roughly 1.0 pg of the desired gene produce per day (1.0 pg/cell/day). Increased or high expression or a high expression level or rate or high productivity are present in particular if the cell according to the invention without prior gene amplification produces at least more than roughly 1.5 pg of the desired gene product per day (1.5 pg/cell/day). Increased or high expression or a high expression level or rate or high productivity are present in particular if the cell according to the invention without prior gene amplification produces at least more than roughly 2.0 pg of the desired gene product per day (2.0 pg/cell/day). Particularly increased or high expression or a particularly high expression level or rate or particularly high productivity are present if the cell according to the invention without prior gene amplification produces at least more than roughly 3.0 pg of the desired gene product per day (3.0 pg/cell/day). By means of a simple gene amplification step, e.g. using the DHFR/MTX amplification system as described hereinafter the productivities can be increased by a factor of at least 2 to 10, so that the terms "high expression", increased expression" or high productivity" are used in relation to a cell which has been subjected to a gene amplification step if this cell produces at least more than roughly 5 pg of the desired gene product per day (5 pg/cell/day), preferably at least more than roughly 10 pg/cell/day, more preferably at least more than roughly 15 pg/cell/day, still more preferably at least more than roughly 20 pg/cell/day or at least more than roughly 30 pg/cell/day.

High or increased expression, high productivity or a high expression level or rate can be achieved both by using one of the expression vectors according to the invention and by the use of one of the processes according to the invention.

For example, by co-expression of the gene of interest and a modified NPT gene it is possible to select and identify cells which express the heterologous gene to a high degree. Compared with wtNPT, modified NPT allows more efficient selection of stably transfected host cells with high expression of the heterologous gene of interest.

The present invention thus also relates to a process for expressing at least one gene of interest in recombinant mammalian cells, characterised in that (i) a pool of mammalian cells is transfected with at least one gene of interest and one gene for a modified neomycin phosphotransferase which compared with the wild-type neomycin phosphotransferase has only 1 to 80% of the activity, preferably only 1 to 60%, more preferably only 1.5 to 30%, most preferably only 1.5 to 26%; (ii) the cells are cultivated under conditions which allow expression of the gene or genes of interest and the modified neomycin phosphotransferase gene; (iii) the mammalian cells are cultivated in the presence of at least one selecting agent, preferably G418, which acts selectively on the growth of the mammalian cells, and gives preference to the growth of those cells which express the modified neomycin phosphotransferase gene; and (iv) the protein or proteins of interest is or are obtained from the mammalian cells or the culture supernatant. Preferably recombinant mammalian cells are used which have been transfected with an expression vector according to the invention.

The invention also relates to a process for selecting recombinant mammalian cells which express at least one gene of interest, wherein (i) a pool of mammalian cells is transfected with at least one gene of interest and a gene for a modified neomycin phosphotransferase which by comparison with wild-type neomycin phosphotransferase has only 1 to 80% of the activity, preferably only 1 to 60%, more preferably only 1.5 to 30%, most preferably only 1.5 to 26%; (ii) the mammalian cells are cultivated under conditions which allow expression of the gene or genes of interest and the modified neomycin phosphotransferase gene; and (iii) the mammalian cells are cultivated in the presence of at least one selecting agent, preferably G418, which acts selectively on the growth of the mammalian cells and gives preference to the growth of those cells which express the modified neomycin phosphotransferase gene.

Particularly preferred are processes for expressing at least one gene of interest and for selecting recombinant cells which express a corresponding gene of interest if a modified NPT gene described in more detail in this application is used, particularly if a modified NPT gene is used which by comparison with the wild-type gene codes for glycine or aspartic acid at amino acid position 182, for alanine at amino acid position 91, for glycine at amino acid position 198, for alanine, glycine or valine at amino acid position 227, for glycine or asparagine at amino acid position 261 or for isoleucine at amino acid position 240. It is particularly preferred to use the Asp227Val, Asp227Gly, Asp261Gly, Asp261Asn, Phe240Ile or Trp91Ala mutant. Generally, all the modified neomycin phosphotransferase genes according to the invention mentioned in this patent specification are suitable for such a process. For the preferred neomycin phosphotransferase genes see the section on modified neomycin phosphotransferase genes.

The selection of the cells which express a gene of interest and a modified NPT gene is carried out for example by adding G418 as selecting agent. However, it is also possible to use other aminoglycoside antibiotics such as neomycin or kanamycin. The cells according to the invention are preferably cultivated and selected in 200 µg/ml to 800 µg/ml of G418 per mL of culture medium. It has proved particularly preferable to add 300 µg/ml to 700 µg/ml of G418 per mL of culture medium. The addition of roughly 400 µg/ml of G418 per mL of culture medium is the most preferred embodiment. Using such a method it is possible to select recombinant cells with a particularly high expression rate. By comparison with the use of wtNPT, after selection with 400 µg G418 per ml of culture medium as selectable marker, the cells exhibited a productivity increased by a factor of 1.4-2.4 in the case of the Glu182Gly, Glu182Asp and Val198Gly mutant, by a factor of 1.6 to 4.1 in the case of the Asp227Gly mutant, by a factor of 2.2 or 4 in the case of the Asp227Ala or Trp91Ala mutant, by a factor of 5.7 or 7.3 in the case of the Phe240Ile or Asp261Asn mutant and even by a factor of 9.3 or 14.6 in the case of the Asp261 Gly or Asp227Val mutant. The specific productivities for the various modified NPT genes are shown in FIG. 6.

The corresponding processes may be combined with a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of (artificial) transcription factors, treatment of the cells with natural or synthetic agents for up-regulating endogenous or heterologous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences (Hemann, C. et al., *DNA Cell Biol* 1994, 13 (4), 437-445) or in vitro amplification systems based on DNA concatemers (Monaco, L. et al., *Gene* 1996, 180, 145-15).

Coupled transcription of the gene of interest and the gene which codes for the fluorescent protein has proved particularly effective in conjunction with the use of a modified NPT gene as selectable marker. The resulting bicistronic mRNA expresses both the protein/product of interest and the fluorescent protein. On the basis of this coupling of the expression of the protein of interest and the fluorescent protein it is easily possible according to the invention to identify and isolate high-producing recombinant host cells by means of the fluorescent protein expressed, e.g. by sorting using fluorescence activated cell sorting equipment (FACS).

The selection of recombinant host cells which exhibit high vitality and an increased expression rate of the desired gene product is a multistage process. The host cells which have been transfected with the expression vector according to the invention or optionally co-transfected with another vector, for example, are cultivated under conditions which permit the selection of cells expressing the modified NPT, e.g. by cultivation in the presence of a selecting agent such as G418 in concentrations of 100 µg/ml, 200 µg/ml, 400 µg/ml, 600 µg/ml, 800 µg/ml or more of G418/mL of culture medium. Then the corresponding cells are investigated at least for the expression of the gene which codes for a fluorescent protein and is coupled to the gene of interest, in order to identify and sort out the cells/cell population which exhibit the highest expression rates of fluorescent protein. Preferably, only the cells which belong to the 10-20% of cells with the highest expression rate of fluorescent protein are sorted out and further cultivated. In practice this means that the brightest 10% of the fluorescent cells are sorted out and further cultivated. Accordingly, the brightest 5%, preferably the brightest 3% or even the brightest 1% of the fluorescent cells of a cell mixture can also be sorted out and replicated. In a particularly preferred embodiment only the brightest 0.5% or the brightest 0.1% of the fluorescent cells are sorted out and replicated.

The selection step may be carried out on cell pools or using pre-sorted cell pools/cell clones. One or more, preferably two or more and especially three or more sorting steps may be carried out, while between the individual sorting steps the cells may be cultivated and replicated for a specific length of time, e.g. roughly two weeks in the case of pools. FIGS. 11 and 12 show specific productivities after FACS-based sorting with and without a gene amplification step for the mutant Asp227Gly, for example.

The present invention thus relates to a process for obtaining and selecting recombinant mammalian cells which express at least one heterologous gene of interest, characterised in that (i) recombinant mammalian cells are transfected with an expression vector according to the invention; (ii) the transfected cells are cultivated under conditions which allow expression of the gene or genes of interest, the gene coding for a fluorescent protein and the modified neomycin phosphotransferase gene; (iii) the mammalian cells are cultivated in the presence of at least one selecting agent which acts selectively on the growth of mammalian cells and gives preference to the growth of those cells which express the modified neomycin phosphotransferase gene; and (iv) the mammalian cells which exhibit a particularly high expression of the fluorescent gene are sorted out by flow-cytometric analysis. If desired steps (ii) to (iv) may be repeated once or several times with the cells obtained in step (iv).

A corresponding process is preferred which is characterised in that the sorted mammalian cells have an average specific productivity, without an additional gene amplification step, of more than 0.5 pg of the desired gene product or products per day and per cell (0.5 pg/cell/day), preferably greater than 1 pg/cell/day, more preferably greater than 2 pg/cell/day, still more preferably greater than 3 pg/cell/day, even more preferably greater than 4 pg/cell/day, for example greater than 5, 6, 7, 8, 9, 10, etc, greater than 15, 20, 25 pg/cell/day, etc. As mentioned above, the productivity of these cells can be increased by a simple gene amplification step, e.g. using the DHFR/MTX system, by a factor of at least 2 to 10. This is shown for example in FIG. 12 for selection using the NTP mutant Asp227Gly. The specific productivities were between 20 and 25 pg/cell/day.

Also preferred according to the invention is a process in which suitably sorted cells are replicated and used to prepare the encoded gene product of interest. For this, the selected high producing cells are preferably cultivated in a serum-free culture medium and preferably in suspension culture under conditions which allow expression of the gene of interest. The protein/product of interest is preferably obtained from the cell culture medium as a secreted gene product. If the protein is expressed without a secretion signal, however, the gene product may also be isolated from cell lysates. In order to obtain a pure homogeneous product which is substantially free from other recombinant proteins and host cell proteins, conventional purification procedures are carried out. First of all, cells and cell debris are removed from the culture medium or lysate. The desired gene product can then be freed from contaminating soluble proteins, polypeptides and nucleic acids, e.g. by fractionation on immunoaffinity and ion exchange columns, ethanol precipitation, reversed phase HPLC or chromatography on Sephadex, silica or cation exchange resins such as DEAE. Methods which result in the purification of a heterologous protein expressed by recombinant host cells are known to the skilled artisan and described in the literature (e.g. Harris et al., Protein Purification: A Practical Approach, Pickwood and Hames, eds., IRL Press 1995; ScopesR., Protein Purification, SpringerVerlag., 1988).

Amplifiable Selectable Marker Gene

In addition, the cells according to the invention may optionally also be subjected to one or more gene amplification steps in which they are cultivated in the presence of a selecting agent which leads to amplification of an amplifiable selectable marker gene. This step may be carried out both with cells which express a fluorescent protein and have preferably been pre-sorted once or several times by FACS (preferably in one of the ways described here) and with cells which have not yet been sorted.

The prerequisite is that the host cells are additionally transfected with a gene which codes for an amplifiable selectable marker. It is conceivable for the gene which codes for an amplifiable selectable marker to be present on one of the expression vectors according to the invention or to be introduced into the host cell by means of another vector.

The amplifiable selectable marker gene usually codes for an enzyme which is needed for the growth of eukaryotic cells under certain cultivation conditions. For example, the amplifiable selectable marker gene may code for dihydrofolate reductase (DHFR). In this case the gene is amplified if a host cell transfected therewith is cultivated in the presence of the selecting agent methotrexate (MTX).

The following Table 2 gives examples of other amplifiable selectable marker genes and the associated selecting agents which may be used according to the invention, which are described in an overview by Kaufman, Methods in Enzymology, 185:537-566 (1990).

TABLE 2

| Amplifiable selectable marker genes | | |
|---|---|---|
| Amplifiable selectable marker gene | Accession number | Selecting agent |
| dihydrofolate reductase | M19869 (hamster) E00236 (mouse) | methotrexate (MTX) |
| metallothionein | D10551 (hamster) M13003 (human) M11794 (rat) | Cadmium |
| CAD (carbamoylphosphate synthetase: aspartate transcarbamylase: dihydroorotase) | M23652 (hamster) D78586 (human) | N-phosphoacetyl-L-aspartate |
| adenosine-deaminase | K02567 (human) M10319 (mouse) | Xyl-A- or adenosine, 2'deoxycoformycin |
| AMP (adenylate)-deaminase | D12775 (human) J02811 (rat) | adenine, azaserin, coformycin |
| UMP-synthase | J03626 (human) | 6-azauridine, pyrazofuran |
| IMP 5'-dehydrogenase | J04209 (hamster) J04208 (human) M33934 (mouse) | mycophenolic acid |
| xanthine-guanin-phosphoribosyltransferase | X00221 (*E. coli*) | mycophenolic acid with limiting xanthine |
| mutant HGPRTase or mutant thymidine-kinase | J00060 (hamster) M13542, K02581 (human) J00423, M68489(mouse) M63983 (rat) M36160 (Herpes virus) | hypoxanthine, aminopterine and thymidine (HAT) |
| thymidylate-synthetase | D00596 (human) M13019 (mouse) L12138 (rat) | 5-fluorodeoxyuridine |
| P-glycoprotein 170 (MDR1) | AF016535 (human) J03398 (mouse) | several drugs, e.g. adriamycin, vincristin, colchicine |
| ribonucleotide reductase | M124223, K02927 (mouse) | aphidicoline |
| glutamine-synthetase | AF150961 (hamster) U09114, M60803 (mouse) M29579 (rat) | methionine sulphoximine (MSX) |
| asparagine-synthetase | M27838 (hamster) M27396 (human) U38940 (mouse) U07202 (rat) | β-aspartylhydroxamate, albizziin, 5'azacytidine |
| argininosuccinate-synthetase | X01630 (human) M31690 (mouse) M26198 (bovine) | canavanin |
| ornithine-decarboxylase | M34158 (human) J03733 (mouse) M16982 (rat) | α-difluoromethylornithine |

TABLE 2-continued

Amplifiable selectable marker genes

| Amplifiable selectable marker gene | Accession number | Selecting agent |
|---|---|---|
| HMG-CoA-reductase | L00183, M12705 (hamster) M11058 (human) | compactin |
| N-acetylglucosaminyl-transferase | M55621 (human) | tunicamycin |
| threonyl-tRNA-synthetase | M63180 (human) | borrelidin |
| $Na^+K^+$-ATPase | J05096 (human) M14511 (rat) | ouabain |

According to the invention the amplifiable selectable marker gene used is preferably a gene which codes for a polypeptide with the function of DHFR, e.g. for DHFR or a fusion protein from the fluorescent protein and DHFR. DHFR is necessary for the biosynthesis of purines. Cells which lack the DHFR genes cannot grow in purine-deficient medium. The DHFR gene is therefore a useful selectable marker for selecting and amplifying genes in cells cultivated in purine-free medium. The selecting medium used in conjunction with the DHFR gene is methotrexate (MTX).

The present invention therefore includes a method of preparing and selecting recombinant mammalian cells which contains the following steps: (i) transfection of the host cells with genes which code at least for a protein/product of interest, a modified neomycin phosphotransferase and DHFR; (ii) cultivation of the cells under conditions which allow expression of the various genes; and (iii) the amplification of the co-integrated genes by cultivating the cells in the presence of a selecting agent which allows the amplification of at least the amplifiable selectable marker gene such as methotrexate. Preferably the transfected cells are cultivated in hypoxanthine/thymidine-free medium in the absence of serum and with the addition of increasing concentrations of MTX. Preferably the concentration of MTX in the first amplification step is at least 5 nM. The concentration of MTX may, however, also be at least 20 nM or 100 nM and be increased step by step to 1 µM. In individual cases concentrations of more than 1 µM may be used, e.g. 2 µM.

If the corresponding cells are additionally transformed with a gene for a fluorescent protein, these cells may be identified and sorted using a fluorescence activated cell sorting device (FACS) and then cultivated in a gene amplification step in the presence of at least 20, preferably in the presence of 50 or 100 nM MTX. In this way it is possible to increase productivities substantially to more than 20 pg of gene product per cell and per day, preferably to more than 21, 22, 23, 24, 25, etc., 30, 35, 40, etc. The host cells may be subjected to one or more gene amplification steps in order to increase the copy number of at least the gene of interest and the amplifiable selectable marker gene. According to the invention the high productivity which can be achieved is linked to effective pre-selection by means of neomycin phosphotransferase-mediated resistance to aminoglycoside antibiotics such as neomycin, kanamycin and G418. It is therefore possible to reduce the number of gene amplification steps required and to carry out only a single gene amplification, for example.

In a further embodiment the present invention thus also relates to processes for obtaining and selecting recombinant mammalian cells which express at least one heterologous gene of interest and are characterised in that (i) recombinant mammalian cells are transfected with an expression vector according to the invention and the gene for an amplifiable selectable marker gene; (ii) the mammalian cells are cultivated under conditions which allow expression of the gene or genes of interest, the modified neomycin phosphotransferase gene and the gene which codes for a fluorescent protein; (iii) the mammalian cells are cultivated in the presence of at least one selecting agent which acts selectively on the growth of mammalian cells and gives preference to the growth of those cells which express the neomycin phosphotransferase gene; (iv) the mammalian cells which exhibit high expression of the fluorescent protein are sorted out by flow-cytometric analysis; (v) the sorted cells are cultivated under conditions under which the amplifiable selectable marker gene is expressed; and (vi) a selecting agent is added to the culture medium which results in the amplification of the amplifiable selectable marker gene.

Particularly preferred is a corresponding process in which the modified neomycin phosphotransferase genes described in this invention are used. Also preferred is a process in which only one amplification step is carried out. Also preferred is a corresponding process which leads to recombinant mammalian cells which exhibit an average specific productivity of more than 20 pg, preferably more than 21, 22, 23, 24, 25, etc., 30, 35, 40, etc. of the desired gene product or products per cell and per day.

Mammalian cells, preferably mouse myeloma and hamster cells, are preferred host cells for the use of DHFR as an amplifiable selectable marker. The cell lines CHO-DUKX (ATCC CRL-9096) and CHO-GD44 (Urlaub, G. et al., *Cell* 1983, 33, 405-412) are particularly preferred as they have no DHFR activity of their own, as a result of mutation. In order to be able to use the DHFR-induced amplification in other cell types as well which have their own endogenous DHFR activity, it is possible to use in the transfection process a mutated DHFR gene which codes for a protein with reduced sensitivity to methotrexate (Simonson, C. C. et al., *Proc Nat/Acad Sci USA* 1983, 80, 2495-2499; Wigler, M. et al., *Proc Nat/Acad Sci USA* 1980, 77, 3567-3570; Haber, D. A. et al., *Somatic Cell Genetics* 1982, 8, 499-508).

The DHFR marker is particularly suitable for the selection and subsequent amplification when using DHFR negative basic cells such as CHO-DG44 or CHO-DUKX, as these cells do not express endogenous DHFR and therefore do not grow in purine-free medium. Consequently, the DHFR gene may be used here as a dominant selectable marker and the transformed cells are selected in hypoxanthine/thymidine-free medium.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and The modifications described herein will become apparent to those skilled in the art from the foregoing description and accompanying drawings. Such modifications are intended to fall within the scope of the appended claims.

EXAMPLES

| Abbreviations | |
|---|---|
| Ala (=A) | alanine |
| AP: | alkaline phosphatase |
| Asn (=N) | asparagine |
| Asp (=D): | aspartic acid |
| bp: | base pair |
| BSA: | bovine serum albumin |
| CHO: | Chinese Hamster Ovary |
| dhfr: | dihydrofolate-reductase |
| DMSO: | dimethylsulphoxide |
| ELISA: | enzyme-linked immunosorbent assay |
| FACS: | fluorescence-activated cell sorter |
| FITC: | fluoresceine-isothiocyanate |
| GFP: | green fluorescent protein |
| Glu (=E): | glutamic acid |
| Gly (=G): | glycine |
| HBSS: | Hanks Balanced Salt Solution |
| HT: | hypoxanthine/thymidine |
| Ile (=I): | isoleucine |
| IRES: | internal ribosomal entry site |
| kb: | kilobase |
| mAb: | monoclonal antibody |
| MCP-1: | monocyte chemoattractant protein-1 |
| MTX: | methotrexate |
| MW: | mean value |
| NPT: | neomycin-phosphotransferase |
| PCR: | polymerase chain reaction |
| PBS: | phosphate buffered saline |
| Phe (=F): | phenylalanine |
| Trp (=W): | tryptophan |
| Val (=V): | valine |
| WT: | wild-type |

Methods

1. Cell Culture and Transfection

The cells CHO-DG44/dhfr$^{-/-}$ (Urlaub, G. et al., *Cell* 1983, 33, 405-412) were permanently cultivated as suspension cells in serum-free CHO-S-SFMII medium supplemented with hypoxanthine and thymidine (Invitrogen GmbH, Karlsruhe, DE) in cell culture flasks at 37° C. in a damp atmosphere and 5% $CO_2$. The cell counts and viability were determined with a CASY1 Cell Counter (Schaerfe System, DE) or by tryptan blue staining and the cells were then seeded in a concentration of $1-3\times10^5$/mL and run every 2-3 days. Lipofectamine Plus Reagent (Invitrogen GmbH) was used for the transfection of CHO-DG44. For each transfection mixture a total of 1 μg of plasmid-DNA, 4 μL of lipofectamine and 6 μL of Plus reagent were mixed together according to the manufacturer's instructions and added in a volume of 200 μL to $6\times10^5$ exponentially growing CHO-DG44 cells in 0.8 mL of HT-supplemented CHO-S-SFMII medium. After three hours' incubation at 37° C. in a cell incubator 2 mL of HT-supplemented CHO-S-SFMII medium was added. For the NPT-based selection the cells were transferred 2 days after transfection into HT-supplemented CHO-S-SFMII medium with G418 (Invitrogen), changing the medium every 3 to 4 days. As a rule, 400 μg/mL of G418 were added for the selection and in some experimental series the concentration was also lowered to 200 μg/mL or raised to 500, 600 or 800 μg/mL. In DHFR- and NPT-based selection in the event of co-transfection, in which one expression vector contained a DHFR and the other expression vector contained a neomycin-phosphotransferase selectable marker, the cells were transferred 2 days after transfection into CHO-S-SFMII medium without the addition of hypoxanthine and thymidine and also G418 (Invitrogen) was added to the medium in a concentration of 400 μg/mL.

A DHFR-based gene amplification of the integrated heterologous genes can be obtained by the addition of the selecting agent MTX (Sigma, Deisenhofen, DE) in a concentration of 5-2000 nM to an HT-free CHO-S-SFMII medium.

2. Expression Vectors

Figure 1:
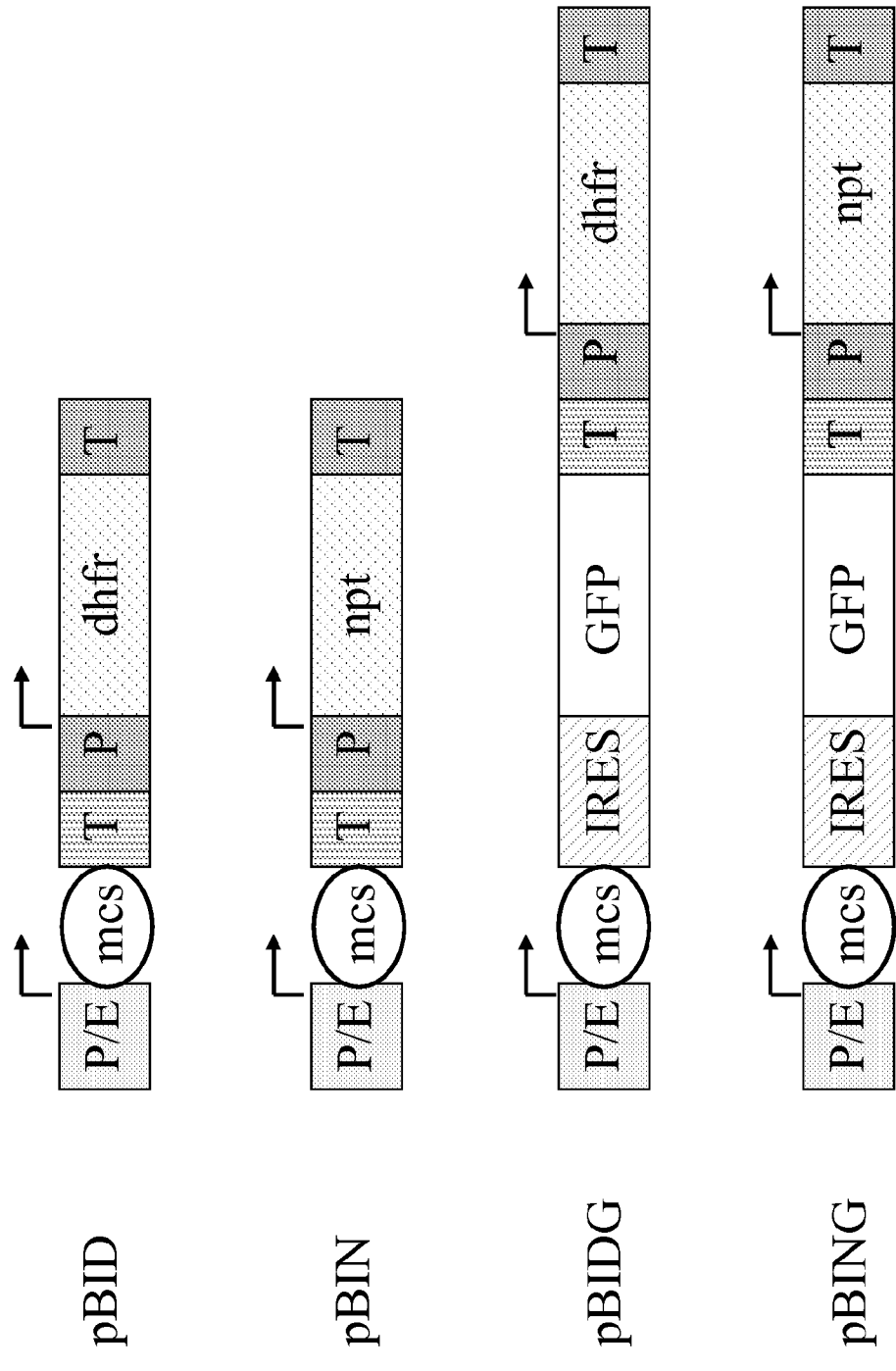
FIG. 1 shows a diagrammatic representation of the base vectors used to express the recombinant proteins in CHO-DG44 cells. "P/E" is a combination of CMV enhancer and hamster-ubiquitin/S27a promoter, "P" on its own indicates a promoter element and "T" is a termination signal for transcription, which is needed for the polyadenylation of the transcribed mRNA. The position and direction of transcription initiation within each transcription unit is indicated by an arrow. For cloning the heterologous genes a sequence region with multiple cutting sites for restriction endonucleases (multiple cloning sites—MCS) is inserted after the promoter element. The amplifiable selectable marker dihydrofolate reductase is abbreviated to "dhfr" and the selectable marker neomycin phosphotransferase is abbreviated to "npt" (npt wild-type or npt mutant). The "IRES" element coming from the encephalomyocarditic virus acts an internal ribosomal entry site within the bicistronic transcription unit and enables translation of the following green fluorescent protein "GFP".

To analyse the expression, eukaryotic expression vectors were used which are based on the pAD-CMV vector (Werner, R. G. et al., *Arzneim.-Forsch./Drug.Res.* 1998, 48, 870-880) and mediate the constitutive expression of a heterologous gene by the combination of CMV enhancer/hamster ubiquitin/S27a promoter (WO 97/15664). While the base vector pBID contains the dhfr-minigene which acts as an amplifiable selectable marker (cf e.g. EP-0-393-438), in the vector pBIN the dhfr-minigene has been replaced by a neomycin-phosphotransferase resistance gene (FIG. 1). For this purpose the selectable marker neomycin-phosphotransferase, including SV40 early promoter and TK-polyadenylation signal, was isolated from the commercial plasmid pBK-CMV (Stratagene, La Jolla, Calif., USA) as a 1640 bp Bsu36I fragment. After a reaction to fill in the ends of the fragment with Klenow-DNA-polymerase the fragment was ligated with the 3750 bp Bsu36I/StuI fragment of the vector pBID, which was also treated with Klenow-DNA-polymerase.

In the bicistronic base vector pBIDG (FIG. 1) the IRES-GFP gene region was isolated from the vector pIRES2-EGFP (Clontech, Palo Alto, Calif., USA) and brought under the control of the CMV enhancer/promoter in the vector pBID so that the multiple cloning site between the promoter region and IRES-element was retained. The following procedure was used. In a PCR mutagenesis in which the plasmid pIRES2-EGFP acted as the template, on the one hand the HindIII cutting site AAGCTT within the IRES sequence was converted into the sequence ATGCTT by the use of mutagenic primers and thus eliminated. On the other hand an XbaI cutting site was inserted by means of a primer with complementarity to the 5' end of the IRES sequence or a SpeI cutting site was introduced by means of a primer with complementarity to the 3' end of the GFP sequence. The resulting PCR fragment, which contained the complete IRES and GFP sequence, was digested with XbaI and SpeI and cloned into the singular XbaI cutting site at the 3' end of the multiple cloning site of the vector pBID. In the same way the IRES-GFP gene region from the vector pIRES2-EGFP was brought under the control of the CMV enhancer/hamster ubiquitin/S27a promoter in the vector pBIN. This produced the bicistronic base vector pBING (FIG. 1).

Figure 2A:
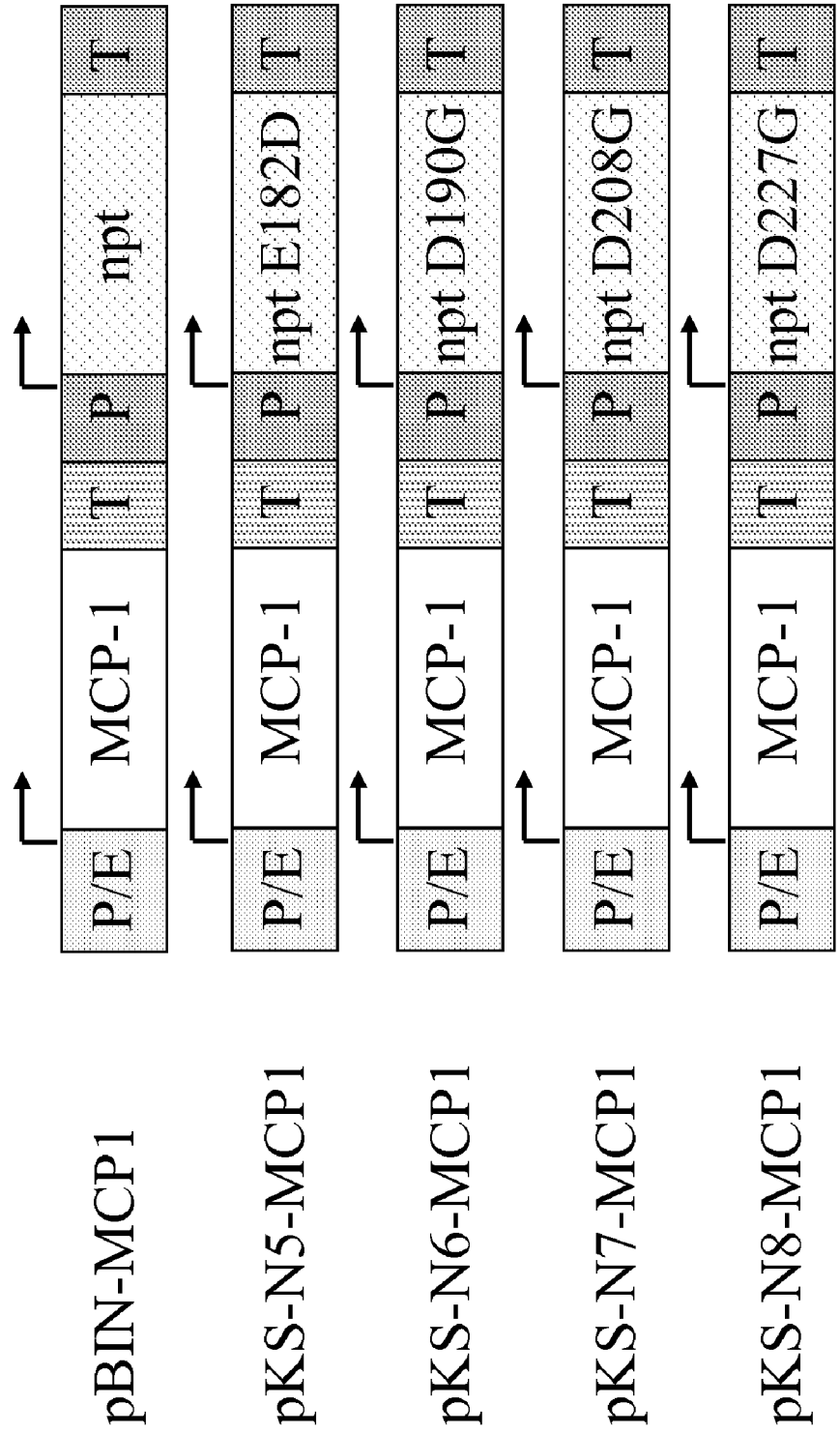
FIG. 2 shows a diagrammatic view of the eukaryotic expression vectors which code for a single-chain protein (FIG. 2A) or for a subunit of a monoclonal antibody (FIG. 2B) and are used to transfect CHO-DG44 cells. "P/E" is a combination of CMV enhancer and hamster ubiquitin/S27a promoter, "P" on its own is a promoter element and "T" is a termination signal for the transcription which is needed for the polyadenylation of the transcribed mRNA. The position and direction of transcription initiation within each transcription unit is indicated by an arrow. The amplifiable selectable marker dihydrofolate reductase is abbreviated to "dhfr" and the selectable marker neomycin phosphotransferase is abbreviated to "npt". The NPT mutants E182G (SEQ ID NO:3), E182D (SEQ ID NO:19), W91A (SEQ ID NO:5), D190G (SEQ ID NO:23), V198G (SEQ ID NO:7), D208G (SEQ ID NO:25), D227A (SEQ ID NO:9), D227V (SEQ ID NO:11), D227G (SEQ ID NO:21), D261G (SEQ ID NO:13), D261N (SEQ ID NO:15) and F240I (SEQ ID NO:17) contain a point mutation which results in a modified amino acid (given in 1-letter code) at the position indicated. The IRES element originating from the encephalomyocarditis virus acts as an internal ribosomal entry site within the bicistronic transcription unit and permits translation of the following green fluorescent protein "GFP". "MCP-1" codes for the Monocyte Chemoattractant Protein-1, whereas "HC" and "LC" code for the heavy and light chains, respectively, of a humanised monoclonal IgG2 antibody.

Human MCP-1 cDNA (Yoshimura, T. et al., *FEBS LETTERS* 1989, 244(2), 487-493) was cloned into the corresponding cutting sites of the vector pBIN as a 0.3 kb HindIII/EcoRI fragment, resulting in the vector pBIN-MCP1 (FIG. 2A).

Figure 2B:
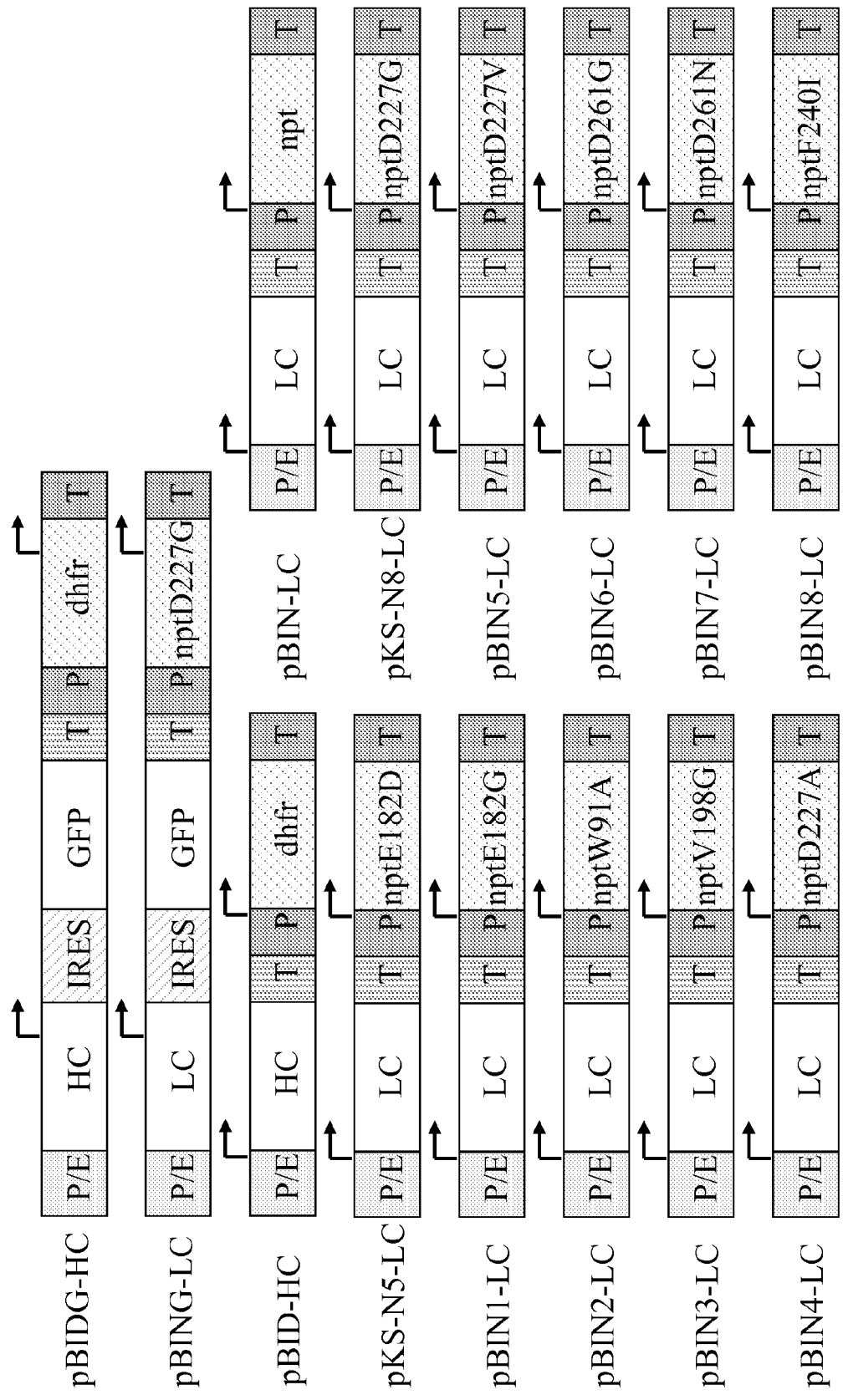

In order to express a monoclonal humanised IgG2 antibody the heavy chain was cloned as a 1.5 kb BamHI/HindIII fragment into the vector pBID or pBIDG digested with BamHI and HindIII, to obtain the vector pBID-HC or pBIDG-HC (FIG. 2B). The light chain on the other hand was cloned as a 0.7 kb BamHI/HindIII fragment into the corresponding cutting sites of the vector pBIN or pBING, producing the vector pBIN-LC or pBING-LC (FIG. 2B).

3. FACS

The flow-cytometric analyses and sorting were carried out with a Coulter Epics Altra device. The FACS is fitted with a helium-argon laser with an excitation wavelength of 488 nm. The fluorescence intensity is absorbed at a wavelength suited to the fluorescence protein and process by means of the attached software Coulter Expo32. The sorting is normally carried out at a rate of 8000-10000 events/second. The suspended cells can be centrifuged (5 min at 180×g) and adjusted to a cell concentration of 1-1.5×10$^7$/mL in HBSS. Then the cells can be sorted according to their fluorescence protein signal. The cells are taken up in test tubes already containing culture medium, then centrifuged and, depending on the number of cells sorted, seeded into suitable culture vessels or deposited directly in microtitre plates.

4. ELISA

The MCP-1 titres in supernatants of stably transfected CHO-DG44 cells were quantified by ELISA using the OptEIA Human MCP-1 Set kit in accordance with the manufacturer's instructions (BD Biosciences Pharmingen, Heidelberg, DE).

The IgG2 mAb in the supernatants from stably transfected CHO-DG44 cells was quantified by ELISA according to standard procedures (Ausubel, F. M. et al., Current Protocols in molecular biology. New York: Greene Publishing Associates and Wiley-Interscience. 1994, using on the one hand a goat anti human IgG Fc fragment (Dianova, Hamburg, DE) and on the other hand an AP-conjugated goat anti human kappa light chain antibody (Sigma). Purified IgG2 antibody was used as the standard.

Productivities (pg/cell/day) were calculated by the formula pg/((Ct−Co)t/ln(Ct−Co)), where Co and Ct are the cell count on seeding and harvest, respectively, and t is the cultivation time.

5. Dot Assay for Determining the NPT Enzyme Activity

In order to prepare a cell extract, 6×10$^6$ cells were washed twice with PBS and then resuspended in 600 μL of extraction buffer (0.135 M Tris-HCl pH 6.8, 20% glycerol, 4 mM dithiothreitol) according to a method of Duch et al. (Duch et al., Gene 1990, 95:285-288). After four cycles of freezing and thawing in a bath of dry ice or water the cell debris was removed by centrifuging and the supernatant was used for the subsequent enzyme assay. The protein concentration in the cell extracts was determined by a Bradford assay using the BIO-RAD protein assay (Bio-Rad Laboratories GmbH, Munich, DE), with BSA as the standard protein (Ausubel, F. M. et al., Current Protocols in molecular biology. New York: Greene Publishing Associates and Wiley-Interscience. 1994.

In order to determine the NPT enzyme activity a Dot Assay was carried out, based on the protocol of Platt et al. 1987. For this, 5 μg, 2.5 μg and 1.25 μg of protein were adjusted with extraction buffer to a final volume of 20 μL, topping up to a total protein content of 5 μg with cell extract from non-transfected CHO-DG44 cells. After the addition of 200 μL of assay buffer (67 mM Tris-HCl pH 7.1, 42 mM MgCl$_2$, 400 mM NH$_4$Cl) plus/minus 40 μg/mL G418 and plus/minus 5 μCi [γ-$^{33}$P]-ATP/mL (NEN) the extracts were incubated at 27° C. for 135 minutes. Then the extracts were filtered in a 96 well vacuum manifold (Schleicher and Schüll, Dassel, DE) through a sandwich of one layer of Whatman 3MM paper, P81 phosphocellulose membrane (Whatman Laboratory Division, Maidstone, Great Britain) and nitrocellulose membrane (Schleicher and Schüll). Proteins phosphorylated by protein kinases and non-phosphorylated proteins bind to the nitrocellulose, while phosphorylated G418 passes through the nitrocellulose and binds to the phosphocellulose. After washing three times with deionised H$_2$O the membranes were removed from the apparatus, washed again with H$_2$O and then air-dried. The radioactive signals were quantified using a Phospho Imager (Molecular Dynamics, Krefeld, DE).

Northern Blot Analysis

Total RNA was isolated from the cells with the TRIZOL reagent according to the manufacturer's instructions (Invitrogen GmbH, Karlsruhe, DE) and the separation of 30 μg RNA by gel electrophoresis and the transfer to a Hybond N+ nylon membrane (Amersham Biosciences, Freiburg, DE) were carried out according to the standard procedure for glyoxal/DMSO-denatured RNA (Ausubel, F. M. et al., Current Protocols in molecular biology. New York: Greene Publishing Associates and Wiley-Interscience. 1994). The probe used for the subsequent non-radioactive hybridisation with the GeneImages CDP-Star Detection Kit (Amersham Biosciences) was a PCR product which comprised the coding region of the NPT gene, FITC-dUTP-labelled according to the manufacturer's instructions with the GeneImages random prime labelling kit (Amersham Biosciences, Freiburg, DE).

6. Dot Blot Analysis

Genomic DNA was isolated from the cells using a DNA isolation kit according to the manufacturer's instructions (DNA Isolation Kit for Cells and Tissue; Roche Diagnostics GmbH, Mannheim, DE). Various amounts of DNA (10 μg, 5 μg, 2.5 μg, 1.25 μg, 0.63 μg and 0.32 μg) were filtered by the standard method (Ausubel, F. M. et al., Current Protocols in molecular biology. New York: Greene Publishing Associates and Wiley-Interscience. 1994) in an alkaline buffer using a 96 well vacuum manifold (Schleicher and Schüll, Dassel, DE) onto a Hybond N+ nylon membrane (Amersham Biosciences, Freiburg, DE). Untransfected CHO-DG44 cells were used as the negative control. The plasmid pBIN-LC was used as the standard (320 pg, 160 pg, 80 pg, 40 pg, 20 pg, 10 pg, 5 pg, 2.5 pg). The probe used for the subsequent non-radioactive hybridisation with the GeneImages CDP-Star Detection Kit (Amersham Biosciences) was a PCR product which comprised the coding region of the NPT gene, FITC-dUTP-labelled according to the manufacturer's instructions with the GeneImages random prime labelling kit (Amersham Biosciences, Freiburg, DE). The chemiluminescence signals were quantified using an ImageMaster VDS-CL (Amersham Biosciences). Then the copy number of the npt genes in the cells in question was determined using the standard series which had been obtained from the signal intensities of the titrated plasmid DNA. The number of plasmid molecules was calculated using Avogadro's constant and the DNA content of a CHO cell was taken to be about 5 pg.

EXAMPLE 1

Mutagenesis of the Neomycin-Phosphotransferase

Figure 3:
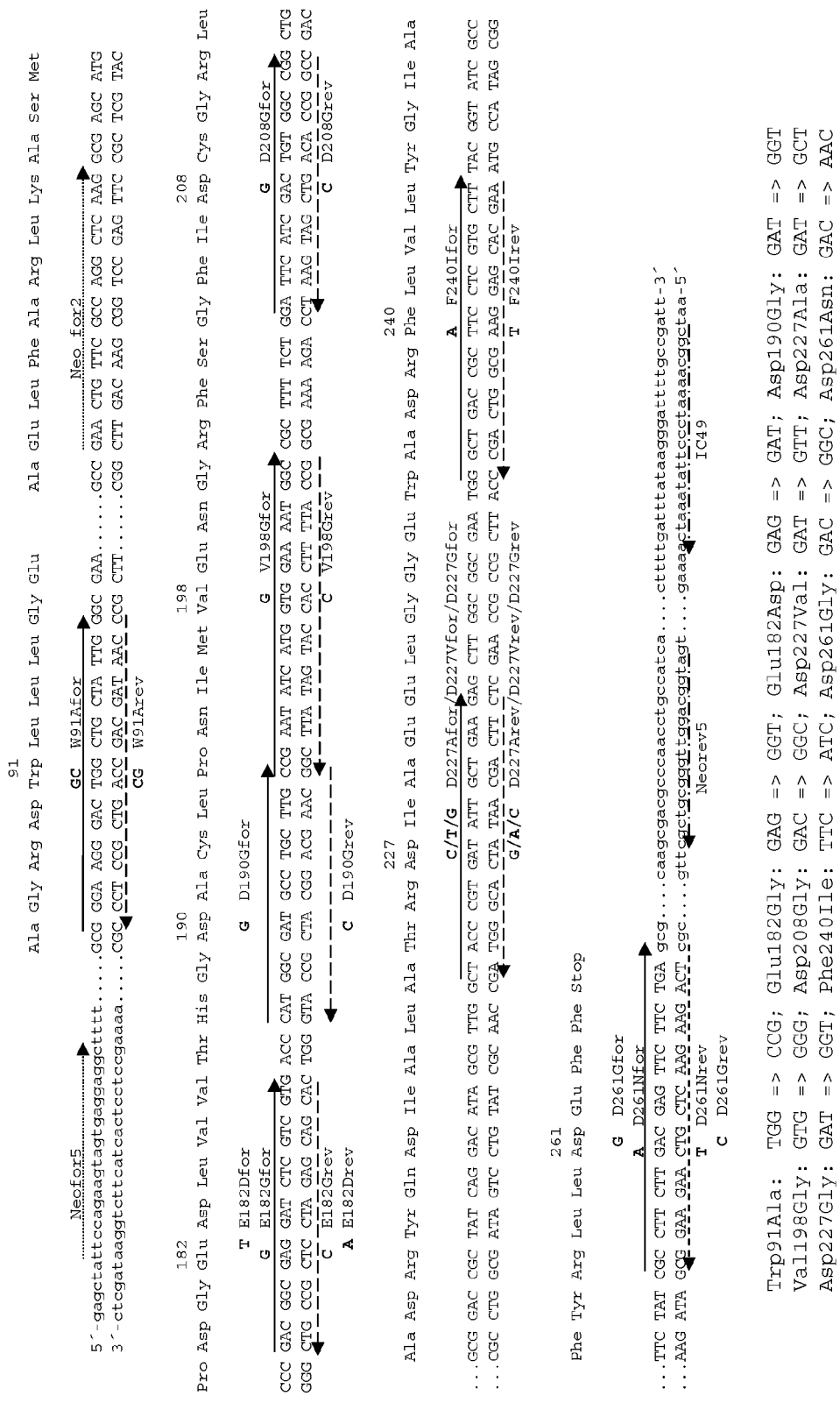
FIG. 3 shows the part of the sequence of the neomycin phosphotransferase (npt) gene in which the point mutations have been inserted by PCR with mutagenic primers. The capital letters indicate the nucleotide sequence of the npt coding region whereas the small letters indicate the flanking non-coding nucleotide sequences. The amino acid sequence predicted from the nucleotide sequence (3-letter code) is shown above the coding nucleotide sequence. Arrows indicate the direction, length and position of the primers used, the arrows with solid lines indicating the mutagenic forward primers, the broken lines indicating the mutagenic reverse primers, the dotted lines indicating the primers Neofor5 (SEQ ID NO:27) or Neofor2 (SEQ ID NO:29) located upstream of the npt gene or the mutation site, respectively, and the dot-dash line indicating the primers Neorev5 (SEQ ID NO:28) or IC49 (SEQ ID NO:30) located downstream of the npt gene or the mutation site, respectively. The nucleotides exchanged with respect to the wild-type sequence are emphasised above and below the arrows.

The base substitutions in the wild-type NPT-gene needed to prepare the NPT mutants Glu182Gly (SEQ ID NO:3), Trp91Ala (SEQ ID NO:5), Val198Gly (SEQ ID NO:7), Asp227Ala (SEQ ID NO:9), Asp227Val (SEQ ID NO:11), Asp261Gly (SEQ ID NO:13), Asp261Asn (SEQ ID NO:15) Phe240Ile (SEQ ID NO:17), Glu182Asp (SEQ ID NO:19), Asp227Gly (SEQ ID NO:21), Asp190Gly (SEQ ID NO:23) and Asp208Gly (SEQ ID NO:25) were carried out by PCR using mutagenic primers (FIG. 3). The vector pBIN (FIG. 1) or pBK-CMV (Stratagene, La Jolla, USA) was used as a template for the PCR mutagenesis. First, the 5' or 3' sections of the mutants were prepared in separate PCR operations. To prepare the mutants Glu182Gly, Glu182Asp, Trp91Ala, Asp190Gly, Val 98Gly, Asp208Gly and Asp227Gly, primer combinations were used for the amplification which consisted of Neofor5 (SEQ ID NO:27) and the relevant mutagenic reverse (rev) primer or Neorev5 (SEQ ID NO:28) and the relevant mutagenic forward (for) primer:

In the case of NPT mutant Glu182Gly (SEQ ID NO:3) of Neofor5 (SEQ ID NO:27) and E182Grev (SEQ ID NO:32) or of Neorev5 (SEQ ID NO:28) and E182 Gfor (SEQ ID NO:31);

in the case of the NPT mutant Glu182Asp (SEQ ID NO:19) of Neofor5 (SEQ ID NO:27) and E182Drev (SEQ ID NO:48) or of Neorev5 (SEQ ID NO:28) and E182Dfor (SEQ ID NO:47);

in the case of the NPT mutant Trp91Ala (SEQ ID NO:5) of Neofor5 (SEQ ID NO:27) and W91Arev (SEQ ID NO:34) or of Neorev5 (SEQ ID NO:28) and W91Afor (SEQ ID NO:33);

in the case of the NPT mutant Val198Gly (SEQ ID NO:7) of Neofor5 (SEQ ID NO:27) and V198Grev (SEQ ID NO:36) or of Neorev5 (SEQ ID NO:28) and V198 Gfor (SEQ ID NO:35)

in the case of the NPT mutant Asp190Gly (SEQ ID NO:23) of Neofor5 (SEQ ID NO:27) and D190Grev (SEQ ID NO:50) or of Neorev5 (SEQ ID NO:28) and D190 Gfor (SEQ ID NO:49);

in the case of the NPT mutant Asp208Gly (SEQ ID NO:25) of Neofor5 (SEQ ID NO:27) and D208Grev (SEQ ID NO:52) or of Neorev5 (SEQ ID NO:28) and D208 Gfor (SEQ ID NO:51);

in the case of the NPT mutant Asp227Gly (SEQ ID NO:21) of Neofor5 (SEQ ID NO:27) and D227Grev (SEQ ID NO:54) or of Neorev5 (SEQ ID NO:28) and D227 Gfor (SEQ ID NO:52).

In order to prepare the mutants Asp227Ala, Asp227Val, Asp261 Gly, Asp261Asn and Phe240Ile primer combinations were used for the amplification which consisted of Neofor2 (SEQ ID NO:29) and the relevant mutagenic reverse (rev) primer or of IC49 (SEQ ID NO:30) and the relevant mutagenic forward (for) primer:

In the case of NPT mutant Asp227Ala (SEQ ID NO:9) of Neofor2 (SEQ ID NO:29) and D227Arev (SEQ ID NO:38) or of IC49 (SEQ ID NO:30) and D227Afor (SEQ ID NO:37);

in the case of NPT mutant Asp227Val (SEQ ID NO:11) of Neofor2 (SEQ ID NO:29) and D227Vrev (SEQ ID NO:40) or of IC49 (SEQ ID NO:30) and D227Vfor (SEQ ID NO:39);

in the case of NPT mutant Asp261Gly (SEQ ID NO:13) of Neofor2 (SEQ ID NO:29) and D261Grev (SEQ ID NO:42) or of IC49 (SEQ ID NO:30) and D261 Gfor (SEQ ID NO:41);

in the case of NPT mutant Asp261Asn (SEQ ID NO:15) of Neofor2 (SEQ ID NO:29) and D261 Nrev (SEQ ID NO:44) or of IC49 (SEQ ID NO:30) and D261Nfor (SEQ ID NO:43);

in the case of NPT mutant Phe240Ile (SEQ ID NO:17) of Neofor2 (SEQ ID NO:29) and F240Irev (SEQ ID NO:46) or of IC49 (SEQ ID NO:30) and F240Ifor (SEQ ID NO:45).

Then the coding strand of the 5'section and the complementary strand of the 3'section of the mutants in question were combined by hybridisation in the overlapping region formed by the mutagenic primer sequences, the single strand regions were filled in and the entire product was amplified again in a PCR with the primers Neofor5 (SEQ ID NO:27) and Neorev5 (SEQ ID NO:28) or Neofor2 (SEQ ID NO:29) and IC49 (SEQ ID NO:30). These PCR products were digested with StuI/RsrII (Neofor5/Neorev5 PCR-products of the mutants Glu182Gly, Trp91Ala and Val198Gly), StuI/BstBI (Neofor5/Neorev5 PCR products of the mutants Glu182Asp, Asp190Gly, Asp208Gly and Asp227Gly) or DraIII/RsrII (Neofor2/IC49 PCR products of the mutants Asp227Ala, Asp227Val, Asp261Gly, Asp261Asn and Phe240Ile). Then in the vector pBIN-LC (FIG. 2B) or pBK-CMV (Stratagene, La Jolla, USA) part of the wild-type NPT sequence was eliminated by StuI/RsrII digestion, DraIII/RsrII digestion or StuI/BstBI digestion and replaced by the corresponding fragments of the PCR products. By sequence analysis of both the complementary and the coding strand the desired base substitutions in the various mutants were verified to ensure that the remaining DNA sequence corresponded to the wild-type NPT sequence. In this way the expression vectors pBIN1-LC, pBIN2-LC, pBIN3-LC, pBIN4-LC, pBIN5-LC, pBIN6-LC, pBIN7-LC and pBIN8-LC were generated, which contain the NPT mutants Glu182Gly, Trp91Ala, Val198Gly, Asp227Ala, Asp227Val, Asp261Gly, Asp261Asn or Phe240Ile (FIG. 2B).

The remaining NPT mutants were isolated as a 1640 bp Bsu36I fragment from the modified pBK-CMV, the fragment ends were filled in with Klenow-DNA polymerase and ligated with the 3750 bp Bsu36I/StuI fragment of the vector pBID, which was also treated with Klenow-DNA polymerase. In this way the expression vectors pKS-N5, pKS-N6, pKS-N7 and pKS-N8 were generated which contained the NPT mutants Glu182Asp, Asp190Gly, Asp208Gly and Asp227Gly, respectively. The human MCP-1 cDNA was then cloned into these expression vectors as a 0.3 kb HindIII/EcoRI fragment (FIG. 2A) or the light chain of the humanised IgG2 antibody was cloned into these expression vectors as a 0.7 kb HindIII/BamHI fragment (FIG. 2B). The mutations inserted in the neomycin phosphotransferase are on the one hand substitutions of more (Val 98Gly, Phe240Ile) or less (Trp91Ala, Glu182Gly, Glu182Asp, Asp227Ala, Asp227Val, Asp227Gly) conserved amino acids which flank conserved domains, such as e.g. the motifs 1, 2 and 3 (Shaw, K. J. et al., *Microbiological Reviews* 1993, 57(1), 138-163) (FIG. 4). On the other hand the mutations are located within the conserved motif 1 (Asp190Gly), 2 (Asp208Gly) or 3 (Asp261 Gly, Asp261Asn) and relate to a conserved amino acid.

EXAMPLE 2

Influence of the NPT Mutations on the Selection of Stably Transfected MCP-1 Expressing Cells MCP was used as an example of the expression of a single chained protein in CHO cells. For this, CHO-DG44 was transfected with pKS-N-5-MCP1, pKS-N-6-MCP1, pKS-N-7-MCP1, pKS-N-8-MCP1 or pBIN-MCP1 (FIG. 2A). Two double preparations were carried out. Two days after transfection the cells were seeded in a 96 well-plate (2000 cells/well) and selected with 400 µg/mL of G418 in HT-supplemented CHO-S-SFMII medium. In the case of the cells transfected with pBIN-MCP1 selection was also carried out in parallel with 800 µg/mL of G418. The cell populations obtained were successively transferred via 24 well plates into 6 well plates. Even during the selection phase differences could be detected between the various transfection mixtures. In contrast to the cell populations in which selection had been carried out with an NPT wild-type gene (SEQ ID NO:1), in those cell populations which had been transfected with a mutated NPT, fewer cells survived the initial selection with G418. These cell populations therefore could not be transferred into the 24 well plates until about four days later. And in the mixtures which has been transfected with pKS-N-6-MCP1 and pKS-N-7-MCP1 no stably transfected cells whatever could be selected at a concentration of 400 µg/mL of G418. Presumably, the enzyme function is so severely impaired in the NPT mutants with the mutations Asp190Gly and Asp208Gly that not enough G418 molecules can be inactivated to allow growth of the stably transfected cells. Admittedly, when the G418 concentration was reduced to 200 µg/mL, a few cells survived the first selection phase, but they were all severely impaired in their growth and vitality and expansion was not possible, apart from a few exceptions in the case of the mutant Asp208Gly.

From the cells transfected with the mutants Glu182Asp and Asp227Gly or with the NPT wild-type, 18 pools were cultivated (9 pools each of mixtures 1 and 2) over four passages in 6 well plates and the concentration of the MCP-1 produced was measured in the cell culture supernatant by ELISA. Cell pools in which the NPT mutants had been used as selectable markers showed on average 50%-57% (Glu182Asp mutant) or 57%-65% (Asp227Gly mutant) higher productivities than cell pools in which the selection had been carried out with the NPT wild-type at 400 or even 800 µg/mL of G418 (FIG. 5). Thus, by using NPT mutants as selectable markers the proportion of high producers in the transfected cell populations could actually be increased.

EXAMPLE 3

Influence of the NPT Mutations on the Selection of Stably Transfected mAb Expressing Cells In a co-transfection CHO-DG44 cells were transfected first with the plasmid combination pBIDG-HC/pBIN-LC (NPT wild-type), pBIDG-HC/pKS-N-5-LC (Glu182Asp NPT mutant) or pBIDG-HC/pKS-N-8-LC (Asp227Gly NPT mutant) (FIG. 2B). In the vector configurations used the two protein chains of a humanised IgG2 antibody are each expressed by their own vector which additionally codes for a DHFR or neomycin selectable marker in a separate transcription unit. The expression of the product genes is mediated by a CMV-Enhancer/Hamster Ubiquitin/S27a Promoter combination. However, comparable data may also be obtained, for example, using a CMV Enhancer/Promoter, an SV40 Enhancer/Hamster Ubiquitin/S27a Promoter or other promoter combinations.

In all, four series of transfections were carried out in each case using 6 pools per plasmid combination. By contrast to the cell populations in which selection was carried out with an NPT wild-type gene, in those cell populations which had been transfected with a mutated NPT, fewer cells survived the initial selection with G418. After two to three weeks' selection of the transfected cell pools in HT-free CHO-S-SFMII medium with the additional 400 µg/mL of G418, the antibody titre in the cell culture supernatants was determined by ELISA over several runs (6-8). By comparison with the use of an NPT wild-type gene as selectable marker, the cells which has been selected with the Glu182Asp mutant showed on average an increase in productivity and titre of 86% and 77%, respectively, and the cells selected with the Asp227Gly mutant even showed an increase in productivity and titre of 126% and 107%, respectively. Thus, by using an NPT mutant with reduced enzyme activity it was possible to selectively enrich cells having a basic productivity which was up to twice as high.

Figure 6A:
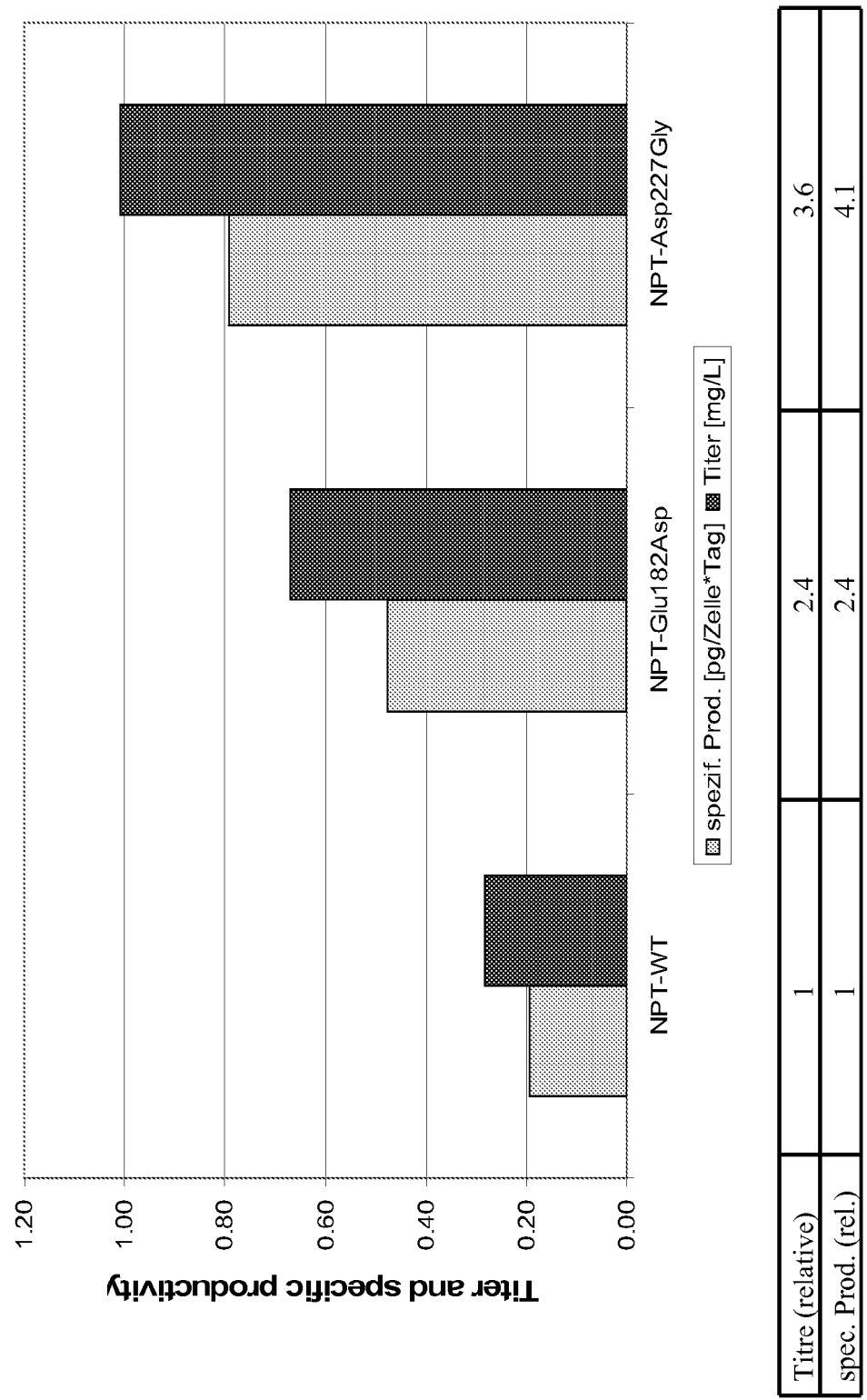
FIG. 6 shows the influence of the NPT mutations on the selection of stably transfected mAb expressing cells. CHO-DG44 cells were transfected with the plasmid combinations pBIDG-HC/pBIN-LC (NPT-wild-type), pBIDG-HC/pKS-N5-LC (NPT mutant Glu182Asp) or pBIDG-HC/pKS-N-8-LC (NPT mutant Asp227Gly) (FIG. 6A) or with the combinations pBIDG-HC/pBIN-LC (NPT-wild-type), pBIDG-HC/pBIN1-LC (NPT mutant Glu182Gly), pBIDG-HC/pBIN2-LC (NPT mutant Trp91Ala), pBIDG-HC/pBIN3-LC (NPT mutant Val198G), pBIDG-HC/pBIN4-LC (NPT mutant Asp227Ala), pBIDG-HC/pBIN5-LC (NPT mutant Asp227Val), pBIDG-HC/pBIN6-LC (NPT mutant Asp261Gly), pBIDG-HC/pBIN7-LC (NPT mutant Asp261Asn) or pBIDG-HC/pBIN8-LC (NPT mutant Phe240Ile) (FIG. 6B) which differ from one another only in the NPT gene (wild-type or mutant) used as a selectable marker. The concentration in the cell culture supernatant of the recombinant monoclonal IgG2 antibody produced was determined by ELISA and the specific productivity per cell and per day was calculated. In all, 5 to 9 pools were set up for each vector combination. The bars represent the averages of the specific productivity or of the titre of all the pools in the Test from 6 cultivation runs in 75 cm² flasks. To calculate the relative titres or the relative specific productivities the averages of the pools selected with the NPT wild-type gene were taken as 1.

In another transfection series the influence of different concentrations of G418 on selection was tested. 400 µg/mL, 500 µg/mL and 600 µg/mL of G418 were used for the selection of the transfected cell pools, 3 pools in each case. At the higher concentrations, significantly fewer cells survived the selection in the cell populations in which selection has been carried out with an NPT wild-type gene, the effect being greatest with the Asp227Gly mutant. The stably transfected cell populations obtained, however, showed no deterioration in growth and vitality. However, no significant difference could be detected between the productivities and titres achieved within a plasmid combination used for transfection. But, even here, the cells selected by the NPT mutants again had the highest productivities on average, led by the Asp227Gly mutant, the productivity of which was four times higher than that of the NPT wild-type, followed by the Glu182Asp mutant with a productivity 2.4 times higher (FIG. 6A).

Then in a co-transfection CHO-DG44 cells were transfected with the plasmid combination pBIDG-HC/pBIN-LC (NPT wild-type), pBIDG-HC/pBIN1-LC (Glu182Gly NPT mutant), pBIDG-HC/pBIN2-LC (Trp91Ala NPT mutant), pBIDG-HC/pBIN3-LC (Val198Gly NPT mutant), pBIDG-HC/pBIN4-LC (Asp227Ala), pBIDG-HC/pBIN5-LC (Asp227Val NPT mutant), pBIDG-HC/pBIN6-LC (Asp261Gly NPT mutant), pBIDG-HC/pBIN7-LC (Asp261Asn NPT mutant) or pBIDG-HC/pBIN8-LC (Phe240Ile NPT mutant) (FIG. 2B). In the vector configurations used, again the two protein chains of a monoclonal humanised IgG2 antibody were each expressed by their own vector, which additionally also codes for a DHFR or neomycin selectable marker in a separate transcription unit.

Figure 6B:
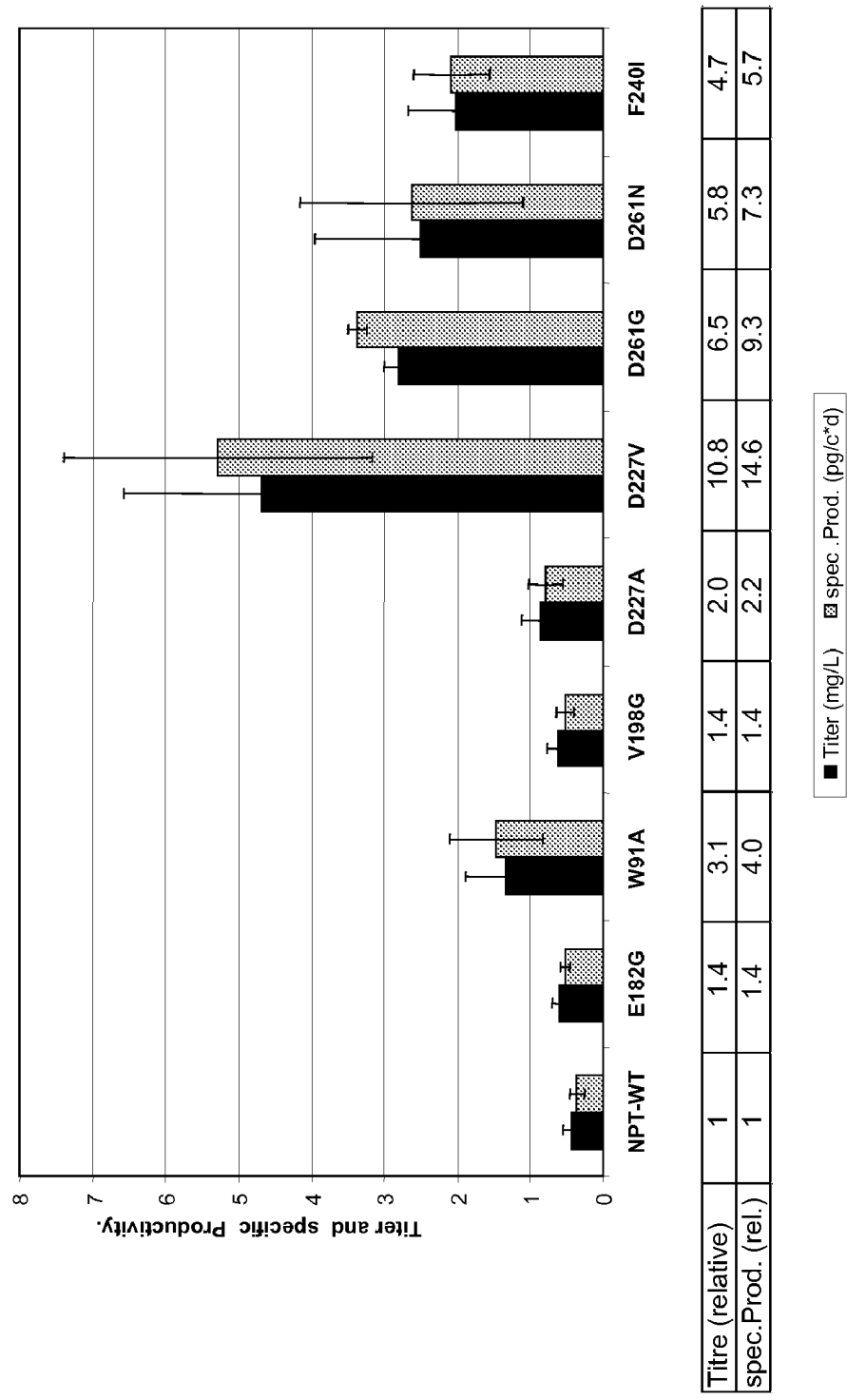

For each plasmid combination, 5 pools were transfected. In contrast to the cell populations in which selection was done with an NPT wild-type gene, fewer cells survived the initial selection with G418 in the cell populations which had been transfected with a mutated NPT. After a two- to three-week selection of the transfected cell pools in HT-free CHO-S-SFMII medium with the addition of 400 µg/mL of G418 the antibody titre in the cell culture supernatants was determined by ELISA over six runs. FIG. 6B shows the averages of the titres and productivities determined from the pools in the test. Compared with the use of an NPT wild-type gene as the selectable marker, all the cell pools which had been selected with an NPT mutant showed on average an increase in productivity and titre by a factor of 1.4-14.6 and 1.4-10.8, respectively (FIG. 6B). The best selective enrichment of cells with a higher basic productivity could thus be obtained with the NPT mutants Asp227Val and Asp261 Gly, with increases in average productivity by a factor of 14.6 and 9.3, respectively.

Figure 7:
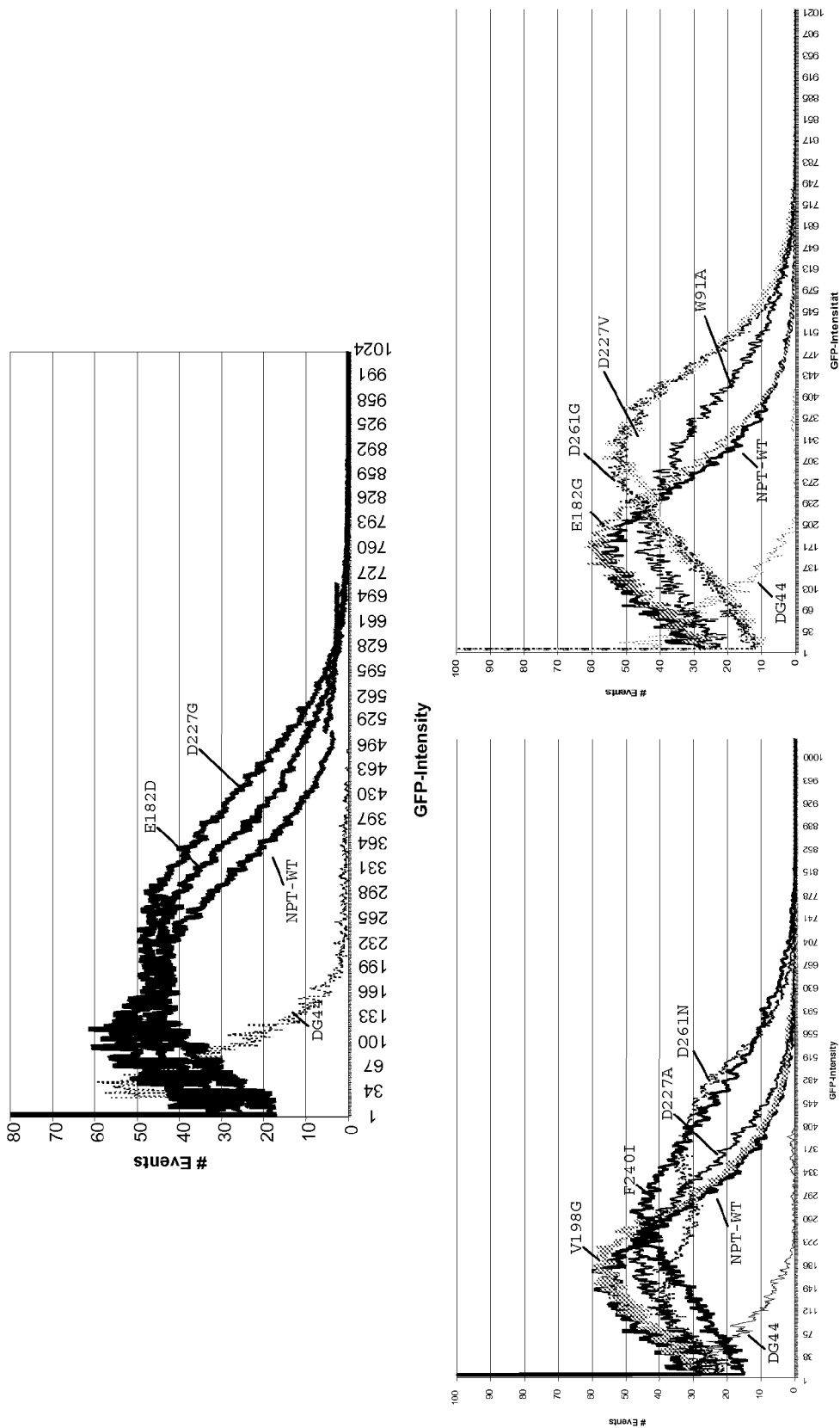
FIG. 7 shows the enrichment of cells with a higher GFP expression in transfected cell pools by using the NPT mutants according to the invention as selectable markers. For this, CHO-DG44 cells were transfected with the plasmid combinations pBIDG-HC/pBIN-LC (NPT-wild-type), pBIDG-HC/pKS-N5-LC (NPT mutant Glu182Asp), pBIDG-HC/pKS-N-8-LC (NPT mutant Asp227Gly), pBIDG-HC/pBIN1-LC (NPT mutant Glu182Gly), pBIDG-HC/pBIN1-LC (NPT mutant Glu182Gly), pBIDG-HC/pBIN2-LC (NPT mutant Trp91Ala), pBIDG-HC/pBIN3-LC (NPT mutant Val198G), pBIDG-HC/pBIN4-LC (NPT mutant Asp227Ala), pBIDG-HC/pBIN5-LC (NPT mutant Asp227Val), pBIDG-HC/pBIN6-LC (NPT mutant Asp261Gly), pBIDG-HC/pBIN7-LC (NPT mutant Asp261Asn) or pBIDG-HC/pBIN8-LC (NPT mutant Phe240e) (5 to 9 pools in each case), which differ from one another only in the NPT gene (wild-type or mutant) used as the selectable marker. Moreover, the pBIDG vectors also contained the GFP as marker gene. After 2 to 3 weeks' selection of the transfected cell pools in HT-free medium with the addition of G418, the GFP fluorescence was measured by FACS analysis. Every graph, with the exception of the non-transfected CHO-DG44 cells used as a negative control, represents the average GFP fluorescence from the pools which had been transfected with the same plasmid combination.

The vector pBIDG-HC contains another selectable marker, GFP. The GFP is transcriptionally linked to the heavy chain via an IRES element. The resulting correlation between the expression of the target protein and the selectable marker GFP therefore also makes it possible to rapidly evaluate the level and distribution of the expression levels in the transfected cell populations on the basis of the GFP fluorescence determined in FACS analyses. After two to three weeks' selection of the transfected cell pools in HT-free CHO-S-SFMII medium with the addition of G418 the GFP fluorescence was measured in a FACS analysis (FIG. 7). The GFP fluorescence signals in fact correlated with the titre data obtained for the monoclonal IgG2 antibody. Pools selected with the NPT mutants Asp227Val, Asp261Gly, Asp161Asn and Phe240Ile also had the higher proportion of cells with a high GFP fluorescence, followed by the cells selected with the NPT mutants Trp91 Ala, Asp227Ala, Asp227Gly, Gly182Asp, Glu182Gly and Val198Gly.

Figure 8:
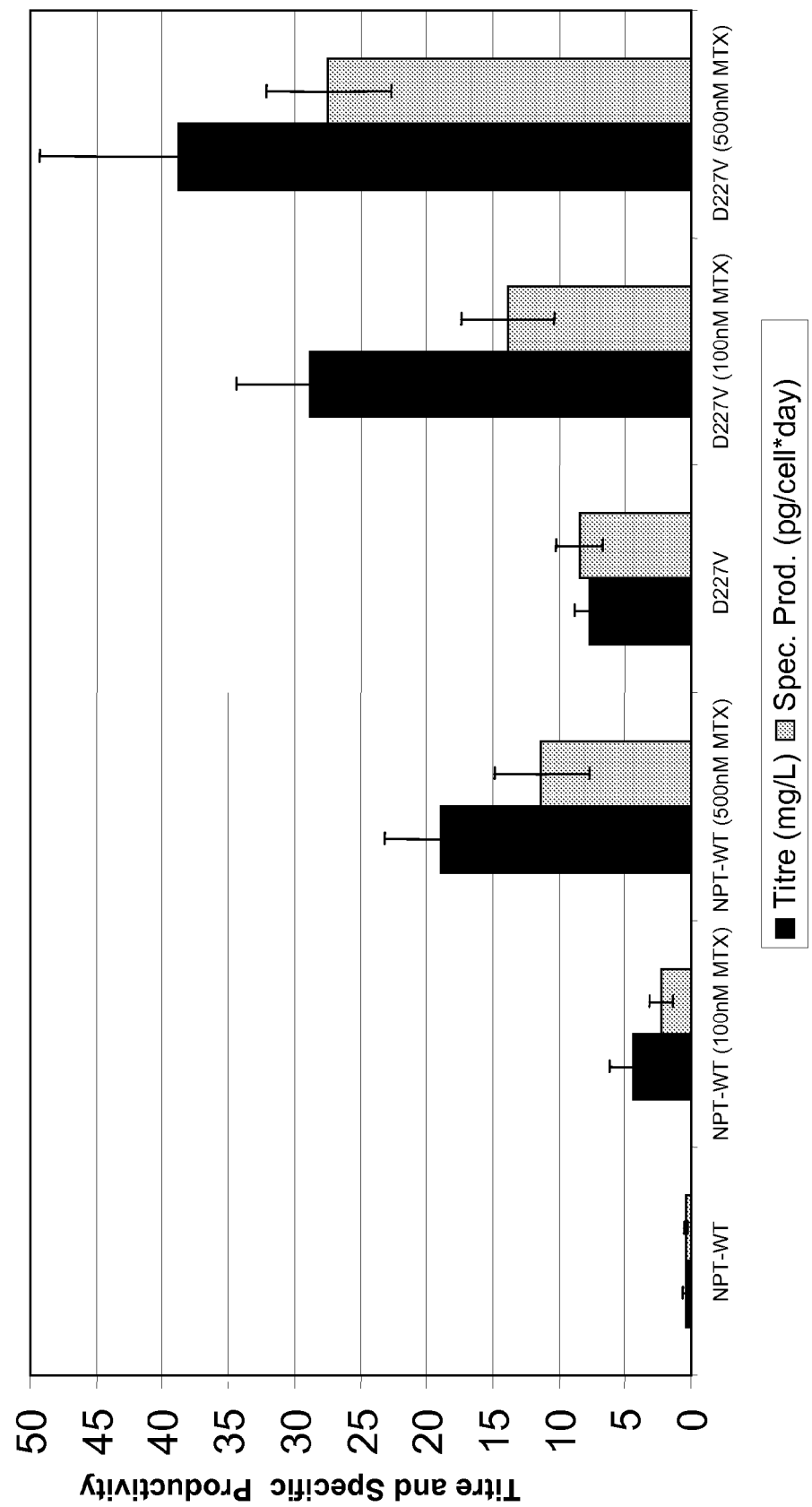
FIG. 8 shows the increase in the mAb productivity achieved by dhfr-mediated gene amplification taking as its example a cell pool which was obtained from the transfection of CHO-DG44 with the vector combination pBIDG-HC/pBIN-LC (NPT-wild-type) or pBIDG-HC/pBIN5-LC (NPT mutant D227V). After the first selection in hypoxanthine/thymidine-free CHO—S—SFMII medium in the presence of G418 a dhfr-mediated gene amplification was carried out by the addition of 100 nM and then 500 nM of MTX to the culture medium. The concentration of the mAb in the cell culture supernatant of the pools was determined by ELISA and the specific productivity per cell and per day (pg/cell/day) was calculated. Each data point represents the average of six cultivation runs in 75 cm² flasks.

By adding the selection agent methotrexate (MTX) to the culture medium it was possible to increase the productivity of the cells still further by inducing a dhfr-mediated gene amplification. Thus, for example, after a simple gene amplification step with 100 nM MTX, the specific productivity in the cells pools obtained by a co-transfection with the plasmid combinations pBIDG-HC/pBIN5-LC (NPT mutant Asp227Val), pBIDG-HC/pBIN6-LC (NPT mutant Asp261Gly), pBIDG-HC/pBIN7-LC (NPT mutant Asp261Asn) and pBIDG-HC/pBIN8-LC (NPT mutant Phe240Ile) could be increased by a factor of 2 to 4 and, depending on the pool, productivities of between 4 and 14 pg/cell/day could be achieved. FIG. 8 shows, by way of example, on a cell pool obtained by the co-transfection of pBIDG-HC/pBIN5-LC (NPT mutant Asp227Val), the increases in productivity to 27 pg/cell/day achieved by the addition of MTX (100 nM MTX followed by 500 nM MTX).

EXAMPLE 4

Determining and Comparing the NPT Enzyme Activity

Figure 9A:
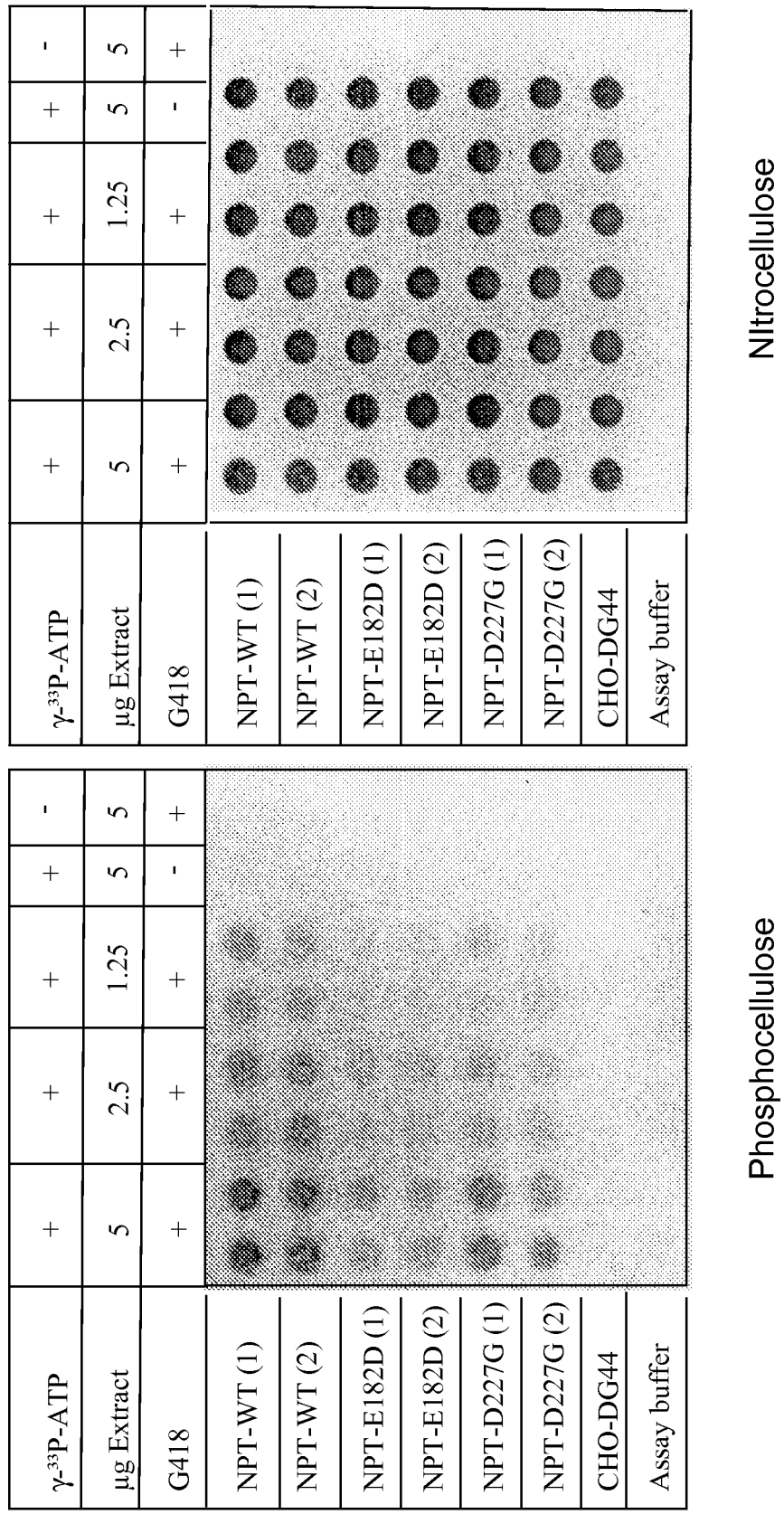
FIG. 9 shows the enzyme activity of the NPT mutants according to the invention compared with the NPT wild-type, in a dot assay. For this, cell extracts were prepared from two different cell pools (pool 1 and 2) expressing mAb, which had been transfected and selected either with the NPT wild-type gene (SEQ ID NO:1) or with the NPT mutants E182G (SEQ ID NO:3), E182D (SEQ ID NO:19), W91A (SEQ ID NO:5), V198G (SEQ ID NO:7), D227A (SEQ ID NO:9), D227V (SEQ ID NO:11), D227G (SEQ ID NO:21), D261G (SEQ ID NO:13), D261N (SEQ ID NO:15) and F2401 (SEQ ID NO:17) Glu182Asp or Asp227Gly. Non-transfected CHO-DG44 cells were used as negative control. G418 was used as the substrate in the phosphorylation assay. The extracts were filtered through a sandwich of P81 phosphocellulose and nitrocellulose membrane in a 96 well vacuum manifold. Proteins phosphorylated by protein kinases and also non-phosphorylated proteins bind to the nitrocellulose, whereas phosphorylated and non-phosphorylated G418 passes through the nitrocellulose and binds to the phosphocellulose (FIG. 9A). The radioactive signals were detected and quantified using a phosphoimager. The signals which had been obtained with 5 μg of extract were used to calculate the percentage enzyme activity. The percentage enzyme activities denote the average of the NPT mutants from 2 cell pools expressing mAb, the enzyme activity of wild-type NPT being taken as 100% (FIG. 9B).

In order to compare the enzyme activity of the NPT mutants with that of the NPT wild-type a dot assay was carried out to determine the NPT activity in cell extracts, based on the procedure of Platt et al. (Platt et al., Anal. Biochem. 1987, 162:529-535) and shown by way of example in FIG. 9A for the NPT mutants Glu182Asp and Asp227Gly. Cell extracts were prepared from two different mAb-expressing cell pools which had been transfected and selected either with the NPT wild-type gene (SEQ ID NO:1) or with the NPT mutants Glu182Gly (SEQ ID NO:3), Glu182Asp (SEQ ID NO:19), Trp91Ala (SEQ ID NO:5), Asp190Gly (SEQ ID NO:23), Val198Gly (SEQ ID NO:7), Asp208Gly (SEQ ID NO:25), Asp227Ala (SEQ ID NO:9), Asp227Val (SEQ ID NO:11), Asp227Gly (SEQ ID NO:21), Asp261Gly (SEQ ID NO:13), Asp261Asn (SEQ ID NO:15) or Phe240Ile (SEQ ID NO:17). Cell extracts from untransfected CHO-DG44 cells were used as the negative control.

The enzyme activities of the NPT mutants were significantly reduced, compared with the NPT wild-type. On average the NPT mutants had only between 1.5% and 62% of the wild-type enzyme activity, while the NPT mutants Asp261Gly and Asp261Asn with 3.1% and 1.5% had the lowest residual activity and the NPT mutants Val198Gly and Trp91Ala with 61.9% and 53.2% has the highest residual activity (FIG. 9B). The signals obtained on the phosphocellulose were specific to the phosphorylation of G418 caused by the NPT enzyme activity. Without the addition of the NPT substrate G418 to the assay buffer no activity could be detected on the phosphocellulose. The signals obtained on the nitrocellulose membrane, which resulted from the proteins phosphorylated by protein kinases within the cell extract, were used as an internal control for identical amounts of sample applied.

Figure 10:
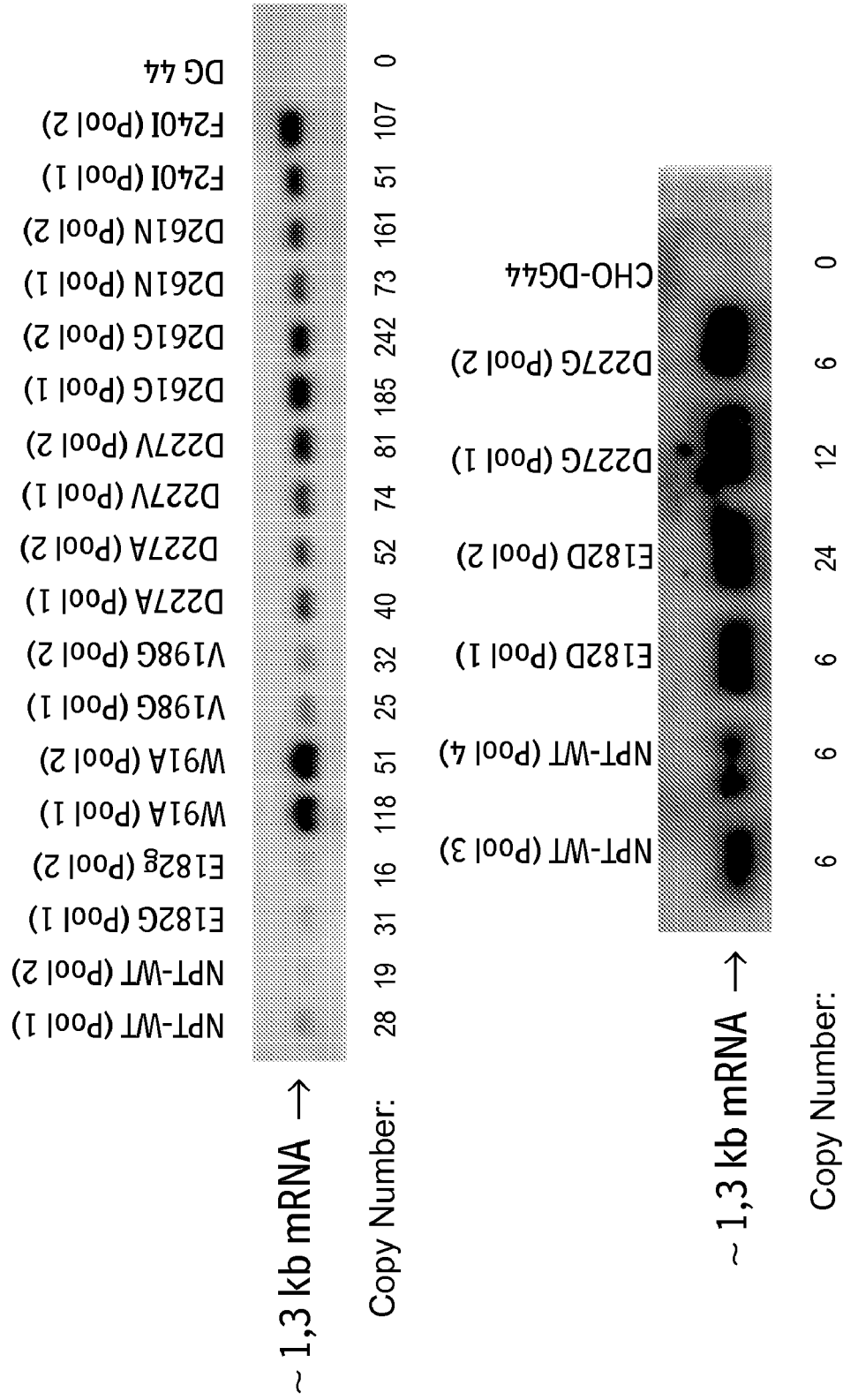
FIG. 10 shows the Northern Blot analysis of NPT expression and the number of NPT gene copies in the transfected cell pools. For this, total RNA was prepared from two different cell pools expressing mAb which were transfected and selected either with the NPT wild-type gene (SEQ ID NO: 1) or with the NPT mutants E182G (SEQ ID NO:3), E182D (SEQ ID NO:19), W91A (SEQ ID NO:5), V198G (SEQ ID NO:7), D227A (SEQ ID NO:9), D227V (SEQ ID NO:11), D227G (SEQ ID NO:21), D261G (SEQ ID NO:13), D261N (SEQ ID NO:15) and F2401 (SEQ ID NO:17). Untransfected CHO-DG44 cells were used as the negative control. Thirty micrograms of RNA was hybridised with a FITC-dUTP-labelled PCR product which comprised the coding region of the NPT gene. In all the transfected cells a specific singular NPT transcript of about 1.3 kb was detected. In order to determine the npt gene copy number, in a dot blot analysis, genomic DNA was isolated from the above-mentioned cell pools expressing mAb.

The reduced enzyme activity of the NPT mutants compared with the NPT wild-type could not be ascribed to reduced gene expression. On the contrary, Northern Blot analyses on total RNA showed that cell pools which had been transfected with the NPT wild-type and exhibited a high NPT enzyme activity expressed less RNA than cell pools transfected with NPT mutants (FIG. 10). The only exception were cells which had been transfected with the NPT mutant Glu182Gly and expressed comparable amounts of NPT-mRNA. In dot blot analyses carried out on genomic DNA from these transfected cell populations it was shown that the higher expression of the NPT mutants was obtained by gene dose effects and/or by integration of the exogenous DNA into more transcription-active genomic regions (FIG. 10). For example, in the cells selected with the NPT mutant Trp91Ala, the gene dose effect is predominant in pool 1 while in pool 2 the integration effect dominates. In this way, transfected cells in which markers with a reduced enzyme activity have been used for the selection are able to synthesise enough marker protein to compensate for the reduced resistance to the selective agent under identical selection pressure.

EXAMPLE 5

Isolation of Cells with High Expression of an mAb by GFP-Based FACS Sorting

In a co-transfection CHO-DG44 cells were transfected with the plasmid combination pBID-HC and pBING-LC, coding for a monoclonal humanised IgG2 antibody (FIG. 2B). In the vector configurations used the two protein chains of the antibody are each expressed by their own vector which additionally also codes for a DHFR or modified neomycin phosphotransferase selectable marker (Asp227Gly mutant; SEQ ID NO:21) in a separate transcription unit. In addition, the vector pBING-LC contains another selectable marker, GFP. As a result of the transcriptional linking of the expression of GFP and the light chain by means of an IRES element, on co-transfection of CHO-DG44 with the vectors pBID-HC/pBING-LC it was possible within a short time to isolate cells with high expression of the monoclonal antibody, purely by selecting the cells with a high GFP content by sequential FACS sorting. In all, 8 separate cell pools were transfected from which after a first two to three weeks selection in HT-free CHO-S-SFMII medium with the addition of 400 μg/mL of G418, stably transfected cell populations were obtained. The titres and productivities of all 8 pools were determined by ELISA overall several runs (7-8). On average the titres were about 1.4 mg/L and the productivities were about 1.3 pg/cell per day. For the subsequent sequential FACS-based sorting the pools 5 and 8 were selected, pool 5 having the highest productivity and pool 8 having a productivity which corresponded to the average of all the pools. In each step, the 5% of cells with the highest GFP fluorescence was sorted out by FACS and further cultivated in the pool. This sorting was carried out up to six times in all, with a cultivation period of about two weeks between each sort. Astonishingly, there was found to be a good correlation between mAb productivity and GFP fluorescence (FIG. 13), although the two protein chains were each expressed by their own vector and during GFP-based FACS sorting, it was only possible to select for the expression of the light chain, as a result of its transcriptional coupling to GFP. The productivities were able to be increased to 9.5 pg/cell/day by FACS-based sorting alone (FIG. 11). Comparable data were also obtained when the Hamster Promoter was functionally linked to the SV40-Enhancer instead of the CMV-Enhancer. By a single subsequent MTX amplification step, starting from pools 5 and 8 of the first sorting step, by adding 100 nM MTX to the selection medium, it was possible to increase the productivity of the pools to an average of more than 20 pg/cell/day (FIG. 12). The high expression levels of the fluorescent protein had no negative effects whatever on cell growth and vitality. During gene amplification the growth properties of the cells are also seriously negatively influenced by the addition of MTX, particularly when it is added in higher concentrations. However, the pre-sorted cell pools showed considerably more robust characteristics in response to the quiet high initial dose of 100 nM MTX. They withstood the selection phase much better, i.e. after only 2 weeks cell populations were obtained with high vitality and a good growth rate.

In addition, the development time for selecting high producing cells was reduced to about 6 weeks, compared with a conventional stepwise gene amplification strategy which generally comprises 4 amplification stages with increasing additions of MTX. This was achieved by the combined use of an enrichment of transfected cells with increased expression of the genes of interest, achieved by using a modified NPT-selectable marker with reduced enzyme activity, followed by a GFP-based FACS sorting with a subsequent gene amplification step.

Various patent applications and publications are cited herein, the disclosures of which are incorporated by reference in their entireties.

What is claimed is:

1. A modified polynucleotide comprising a nucleotide sequence encoding a polypeptide having neomycin phosphotransferase activity, wherein:
   i) said nucleotide sequence is at least 90% identical to the nucleotide sequence of SEQ ID NO:1;
   ii) said polypeptide has 1% to 80% of the neomycin phosphotransferase activity of the polypeptide of SEQ ID NO:2; and
   iii) said polypeptide comprises a different amino acid at position 91, position 198 or position 240 when compared to the polypeptide of SEQ ID NO:2.

2. The polynucleotide of claim 1, wherein said neomycin phosphotransferase activity is determined in a dot assay.

3. The polynucleotide of claim 1, wherein said nucleotide sequence is at least 95% identical to the nucleotide sequence of SEQ ID NO:1.

4. The polynucleotide of claim 1, wherein said nucleotide sequence is at least 97% identical to the nucleotide sequence of SEQ ID NO:1.

5. The polynucleotide of claim 1, wherein said polypeptide has 1% to 60% of the neomycin phosphotransferase activity of the polypeptide of SEQ ID NO:2.

6. The polynucleotide of claim 1, wherein said polypeptide has 1% to 30% of the neomycin phosphotransferase activity of the polypeptide of SEQ ID NO:2.

7. The polynucleotide of claim 1, wherein said polypeptide has 1.5% to 26% of the neomycin phosphotransferase activity of the polypeptide of SEQ ID NO:2.

8. The polynucleotide of claim 1, wherein said polypeptide comprises an alanine at position 91 when compared to the polypeptide of SEQ ID NO:2.

9. The polynucleotide of claim 1, wherein said polypeptide comprises a glycine at position 198 when compared to the polypeptide of SEQ ID NO:2.

10. The polynucleotide of claim 1, wherein said polypeptide comprises an isoleucine at position 240 when compared to the polypeptide of SEQ ID NO:2.

11. A eukaryotic expression vector comprising the polynucleotide according to claim 1.

12. An isolated mammalian cell comprising the polynucleotide according to claim 1.

13. A method of enriching a mammalian cell, comprising:
   (i) transfecting a pool of mammalian cells with a gene for a modified neomycin-phosphotransferase according to claim 1;
   (ii) cultivating the mammalian cells under conditions which allow expression of the modified neomycin-phosphotransferase gene; and
   (iii) cultivating the mammalian cells in the presence of at least one selecting agent which acts selectively on the growth of mammalian cells, and gives preference to the growth of the cells which express the modified neomycin-phosphotransferase gene.

14. A modified polynucleotide encoding a polypeptide comprising the amino acid sequence according to SEQ ID NO:6.

15. The polynucleotide according to claim 14, wherein said polynucleotide comprises the nucleotide sequence according to SEQ ID NO:5.

16. A eukaryotic expression vector comprising the polynucleotide according to claim 14.

17. A eukaryotic expression vector comprising the polynucleotide according to claim 15.

18. An isolated mammalian cell comprising the polynucleotide according to claim 14.

19. An isolated mammalian cell comprising the polynucleotide according to claim 15.

20. A modified polynucleotide encoding a polypeptide comprising the amino acid sequence according to SEQ ID NO:8.

21. The polynucleotide according to claim 20, wherein said polynucleotide comprises the nucleotide sequence according to SEQ ID NO:7.

22. A eukaryotic expression vector comprising the polynucleotide according to claim 20.

23. A eukaryotic expression vector comprising the polynucleotide according to claim 21.

24. An isolated mammalian cell comprising the polynucleotide according to claim 20.

25. An isolated mammalian cell comprising the polynucleotide according to claim 21.

26. A modified polynucleotide encoding a polypeptide comprising the amino acid sequence according to SEQ ID NO:18.

27. The polynucleotide according to claim 26, wherein said polynucleotide comprises the nucleotide sequence according to SEQ ID NO:17.

28. A eukaryotic expression vector comprising the polynucleotide according to claim 26.

29. A eukaryotic expression vector comprising the polynucleotide according to claim 27.

30. An isolated mammalian cell comprising the polynucleotide according to claim 26.

31. An isolated mammalian cell comprising the polynucleotide according to claim 27.

* * * * *